US011617969B2

(12) United States Patent
Abbott et al.

(10) Patent No.: US 11,617,969 B2
(45) Date of Patent: Apr. 4, 2023

(54) ACTIVATED RELEASE OF TARGET MATERIAL TRAPPED IN ANISOTROPIC FLUIDS

(71) Applicant: Wisconsin Alumni Research Foundation, Madison, WI (US)

(72) Inventors: Nicholas Abbott, Madison, WI (US);
Youngki Kim, Madison, WI (US);
Xiaoguang Wang, Madison, WI (US);
Emre Bukusoglu, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 807 days.

(21) Appl. No.: 16/309,656

(22) PCT Filed: Jun. 14, 2017

(86) PCT No.: PCT/US2017/037414
§ 371 (c)(1),
(2) Date: Dec. 13, 2018

(87) PCT Pub. No.: WO2017/218635
PCT Pub. Date: Dec. 21, 2017

(65) Prior Publication Data
US 2019/0329155 A1    Oct. 31, 2019

Related U.S. Application Data

(60) Provisional application No. 62/349,986, filed on Jun. 14, 2016.

(51) Int. Cl.
*B01D 17/00*    (2006.01)
*B01D 17/02*    (2006.01)
(Continued)

(52) U.S. Cl.
CPC .......... *B01D 17/005* (2013.01); *A61K 9/0009* (2013.01); *A61K 9/1075* (2013.01);
(Continued)

(58) Field of Classification Search
CPC .......... B01D 17/12; B01D 17/02; A61K 9/00; A61K 9/107; C09K 19/02
See application file for complete search history.

(56) References Cited

U.S. PATENT DOCUMENTS

2009/0269323 A1* 10/2009 Luk ................... C12N 11/04
424/94.3
2014/0079679 A1*  3/2014 Perricone ............... A61K 9/107
424/94.1

OTHER PUBLICATIONS

Chuealee et al. (Proceedings of the 2nd IEEE International Conference on Nano/Micro Engineered and Molecular systems, Jan. 16-19, 2007, 1098-1103). (Year: 2007).*

(Continued)

*Primary Examiner* — Walter D. Griffin
*Assistant Examiner* — Cameron J Allen
(74) *Attorney, Agent, or Firm* — Bell & Manning, LLC

(57) ABSTRACT

Systems and methods for the controlled release of a guest composition that is sequestered within a host composition made up of an anisotropic fluid are disclosed. The guest composition is immiscible in the host composition, thus forming an interface between the compositions upon which elastic repulsion forces act to prevent the release of the guest composition from the host composition. The disclosed systems and methods work by changing the elastic repulsion forces and/or introducing one or more counter forces such that the elastic repulsion forces are no longer sufficient to prevent release of the guest composition. Exemplary methods include mechanically changing the host material (e.g., changing its temperature) or inducing a chemical (e.g., electrostatic) attraction sufficient to overcome the elastic
(Continued)

repulsion forces. The disclosed systems and methods can be used for a variety of applications requiring "on-demand" delivery of a chemical composition.

20 Claims, 26 Drawing Sheets

(51) Int. Cl.
    *C09K 19/02*     (2006.01)
    *A61K 9/00*     (2006.01)
    *A61K 9/107*     (2006.01)
    *B01D 17/12*     (2006.01)

(52) U.S. Cl.
    CPC ............ *B01D 17/02* (2013.01); *B01D 17/12* (2013.01); *C09K 19/02* (2013.01)

(56) References Cited

OTHER PUBLICATIONS

Fong, W.K. et al.: "Stimuli responsive liquid crystals provide 'on-demand' drug delivery in vitro and in vivo", Journal of Controlled Release, vol. 135, No. 3, May 5, 2009, pp. 218-226.

Guo, C. et al.: "Lyotropic liquid crystal systems in drug delivery", Drug Discovery Today, vol. 15, No. 23-24, Dec. 1, 2010, pp. 1032-1040.

Bychkova, A.V. et al.: "Magnetic and transport properties of magneto-anisotropic nanocomposites for controlled drug delivery", Nanotechnologies in Russia, vol. 10, No. 3-4, May 3, 2015, pp. 325-335.

Negrini, Renata et al.: "pH-responsive lyotropic liquid crystals for controlled drug delivery", Langmuir, vol. 27, May 3, 2011, pp. 5296-5303.

Murdan, S. (Ed), Hanes, Justin et al.: "Electro-responsive drug delivery from hydrogels", Journal of Controlled Release, vol. 92, No. 1-2, Sep. 19, 2003, pp. 1-17.

\* cited by examiner

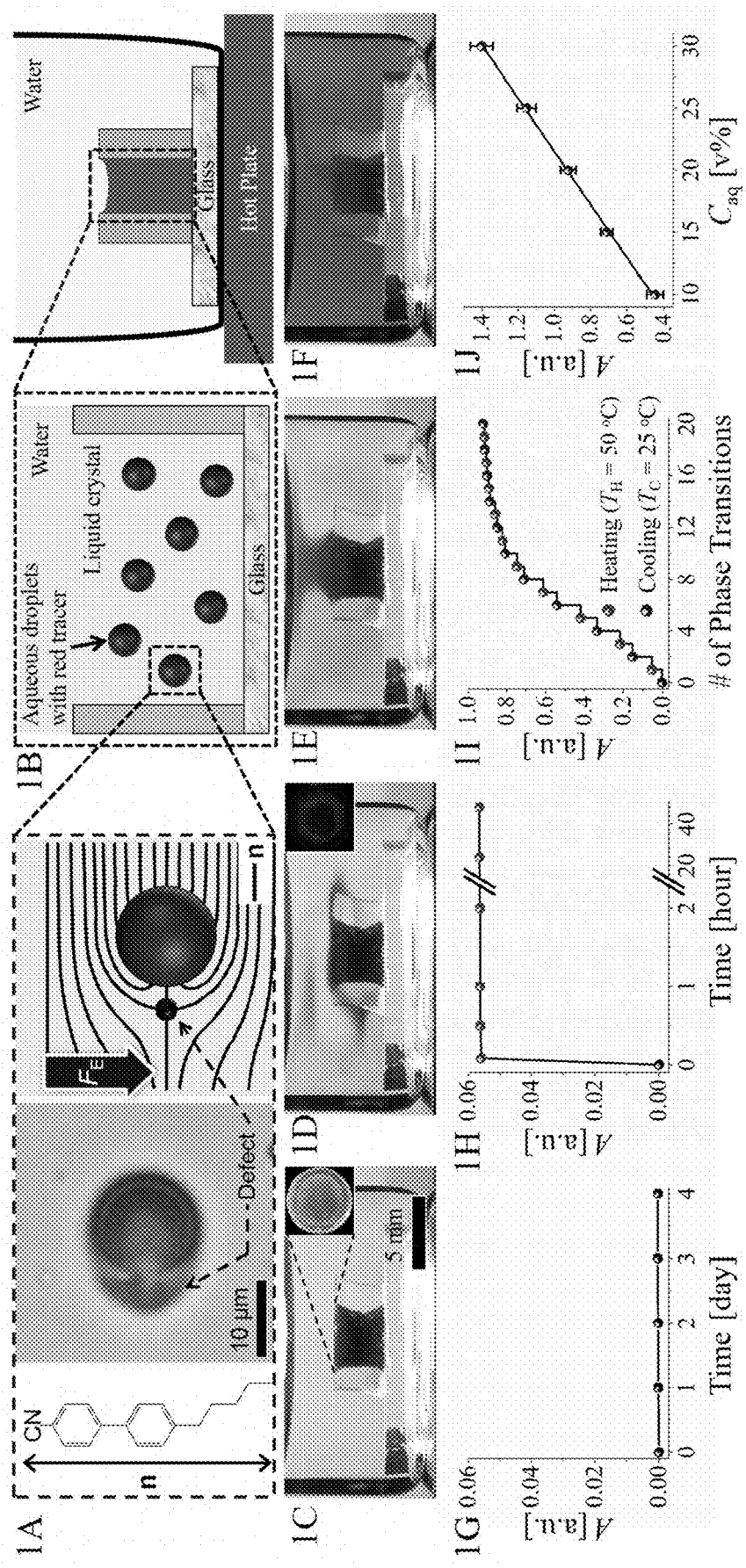
FIGURES 1A, 1B, 1C, 1D, 1E, 1F, 1G, 1H, 1I, and 1J

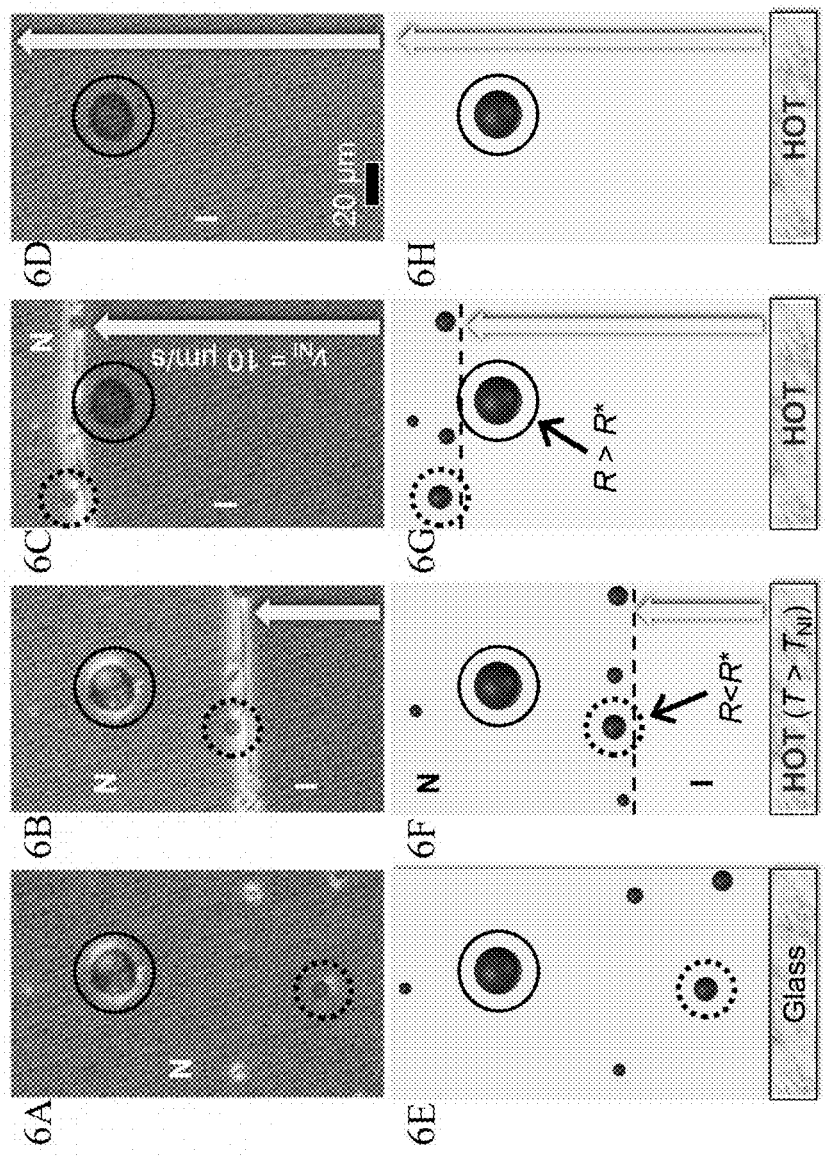
FIGURES 6A, 6B, 6C, 6D, 6E, 6F, 6G, and 6H

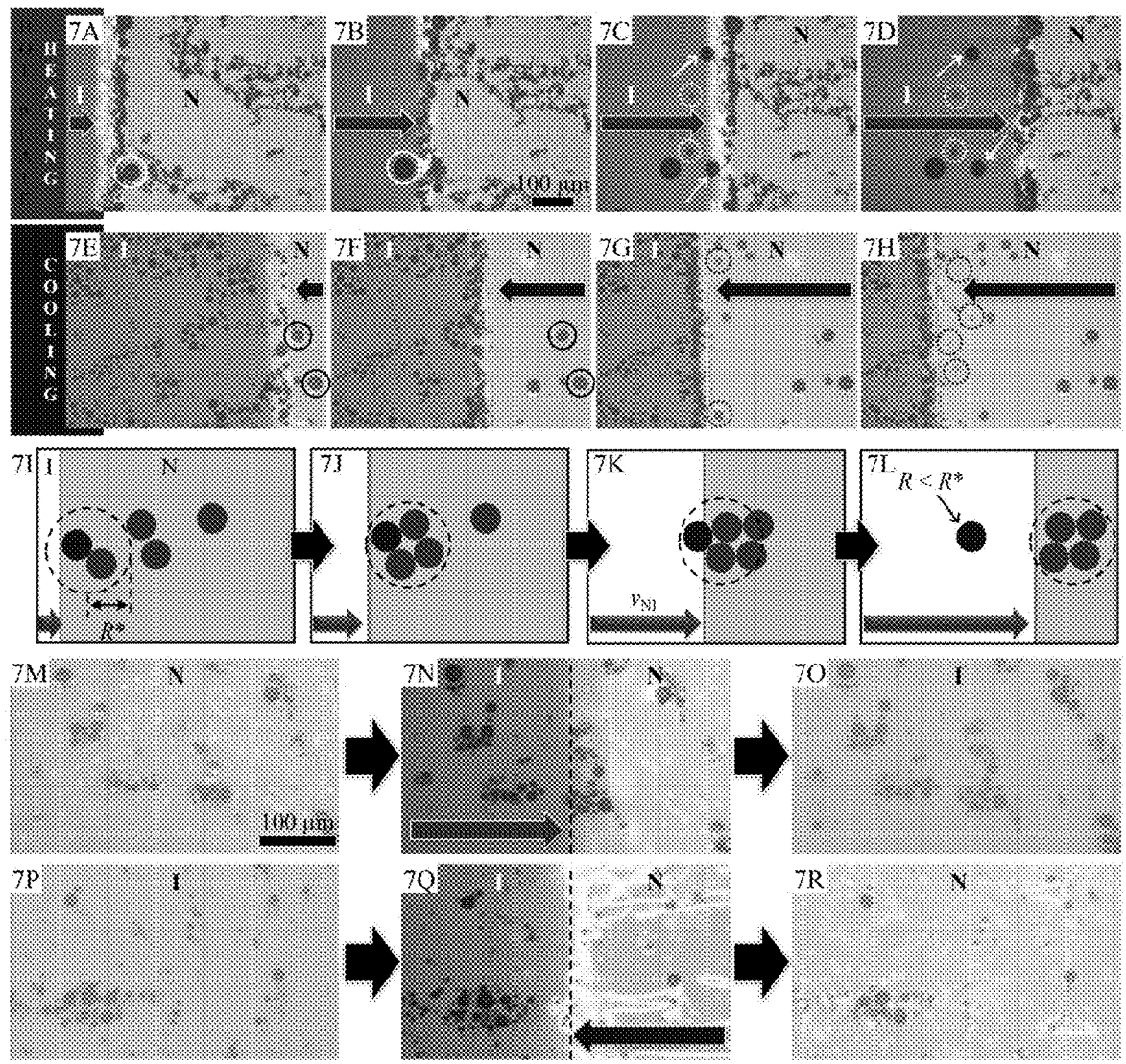
FIGURES 7A, 7B, 7C, 7D, 7E, 7F, 7G, 7H, 7I, 7J, 7K, 7L, 7M, 7N, 7O, 7P, 7Q, and 7R 12J, 12K, 12L, 12M, 12N, and 12O

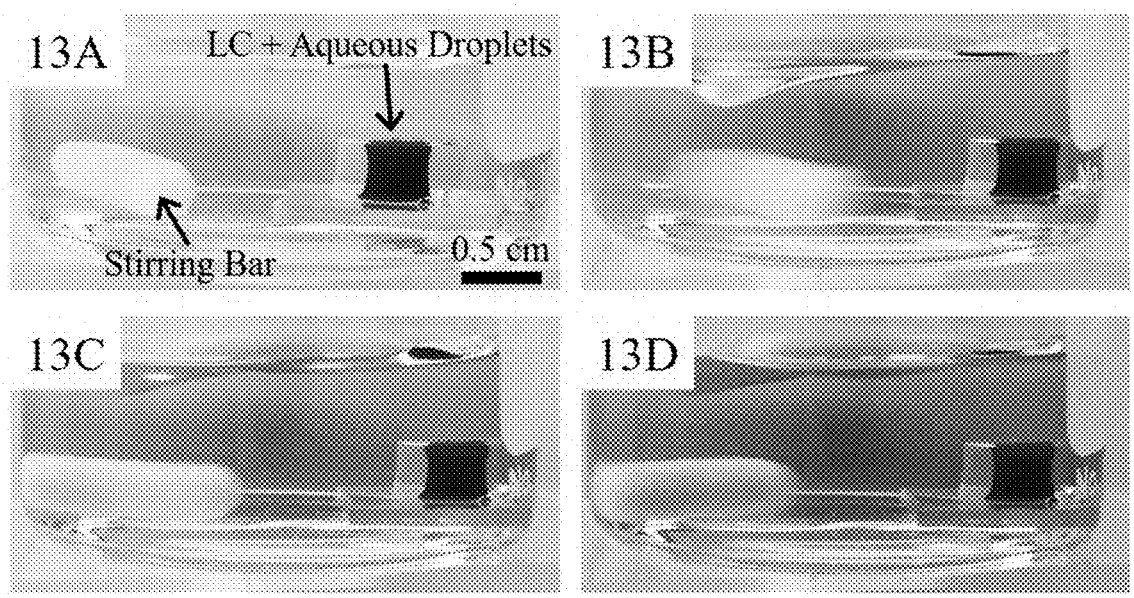
FIGURES 13A, 13B, 13C, and 13D

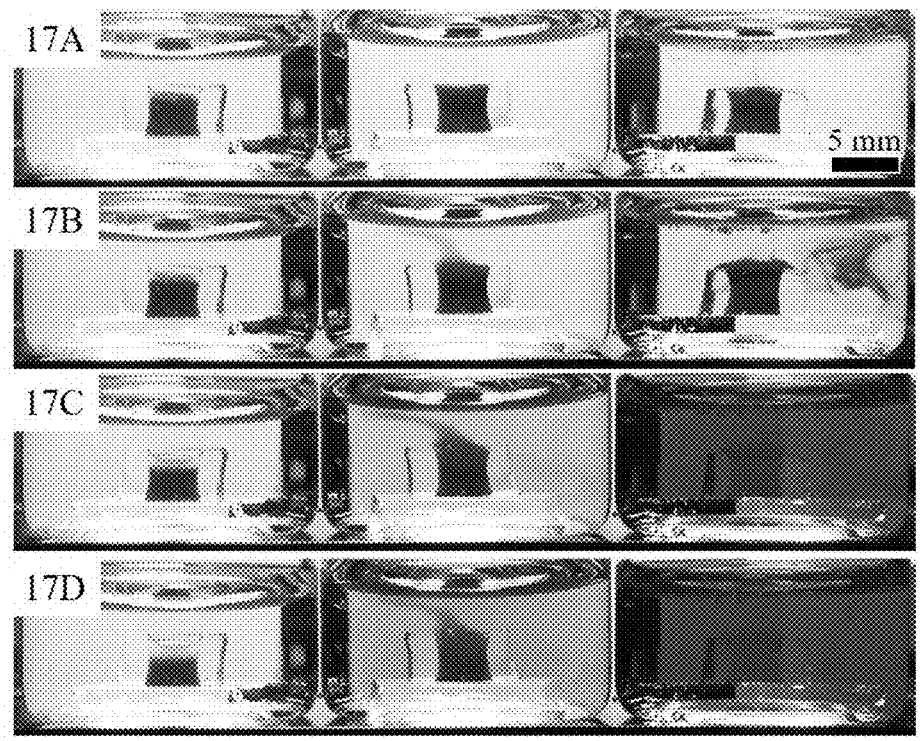
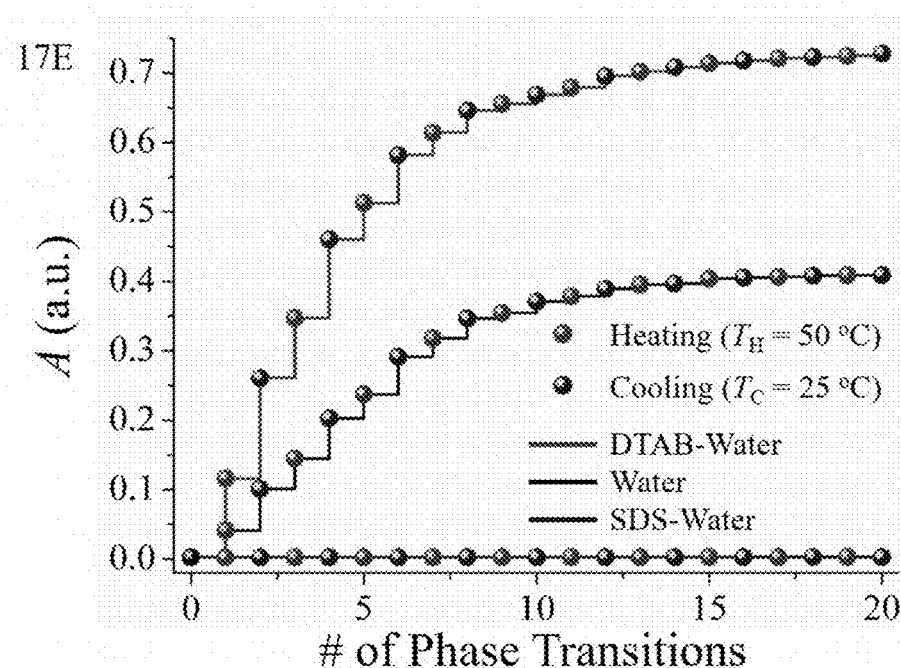
FIGURES 17A, 17B, 17C, 17D and 17E

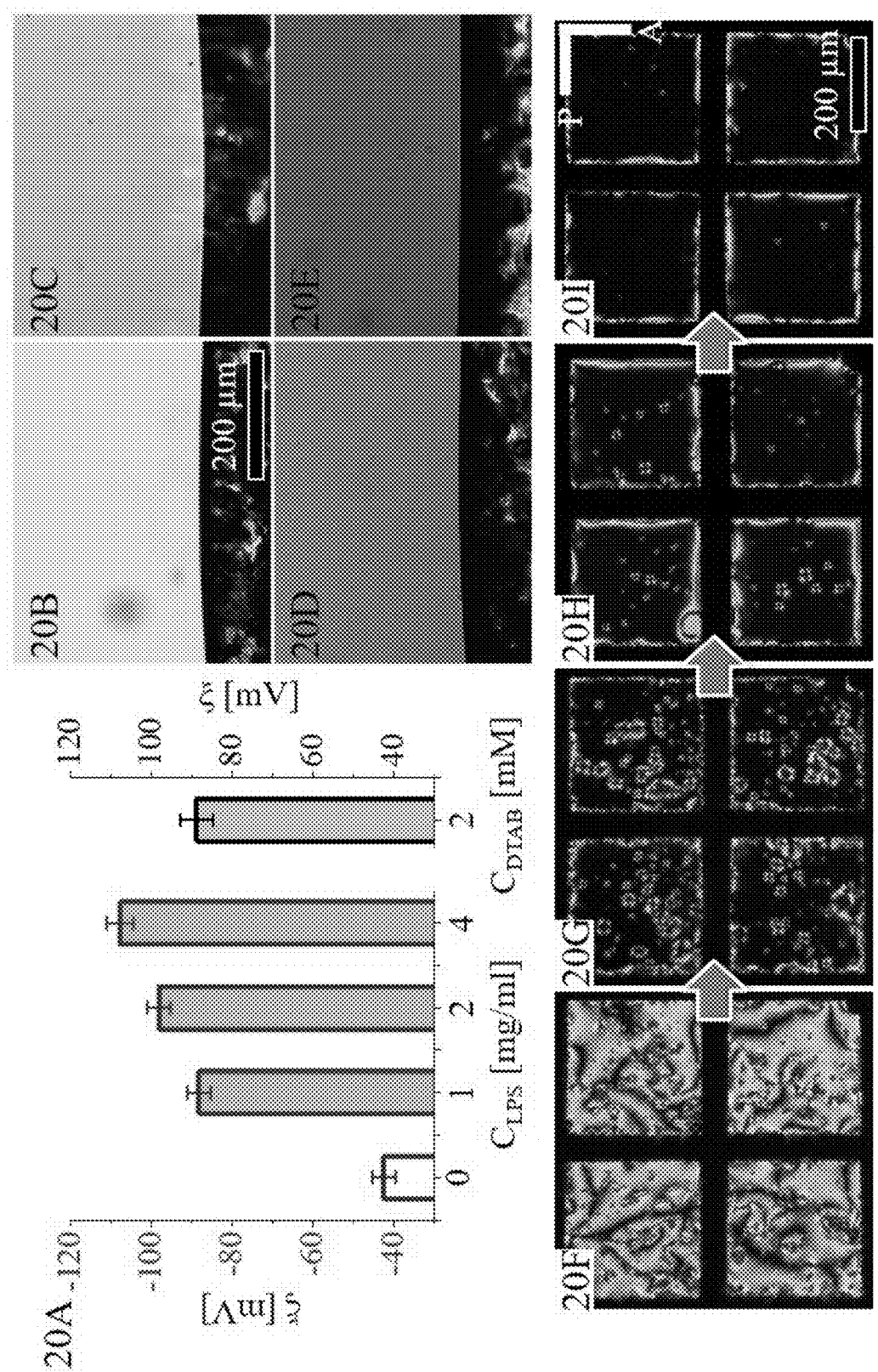
FIGURE 20A, 20B, 20C, 20D, 20E, 20F, 20G, 20H, and 20I

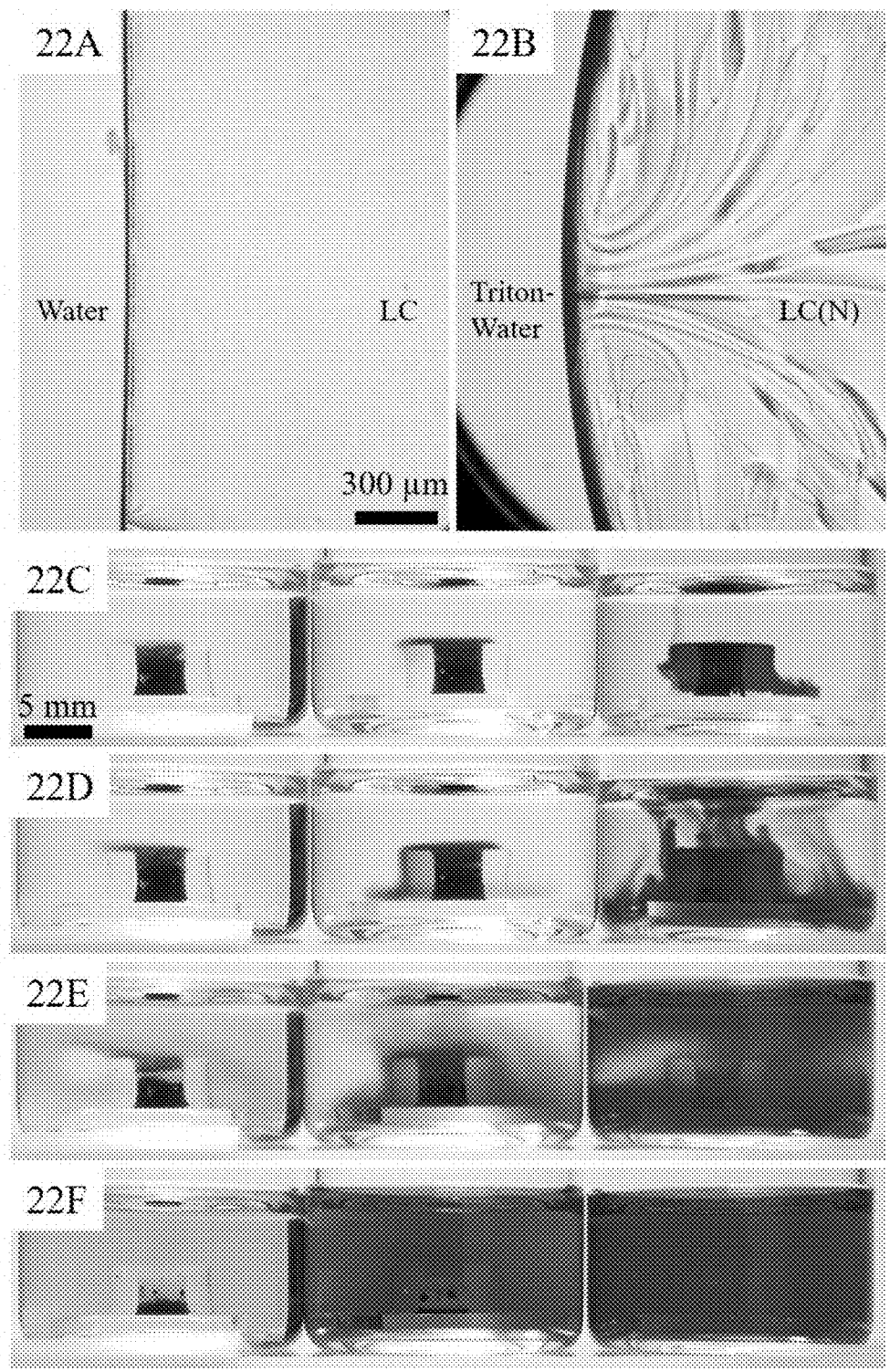
FIGURES 22A, 22B, 22C, 22D, 22E, and 22F

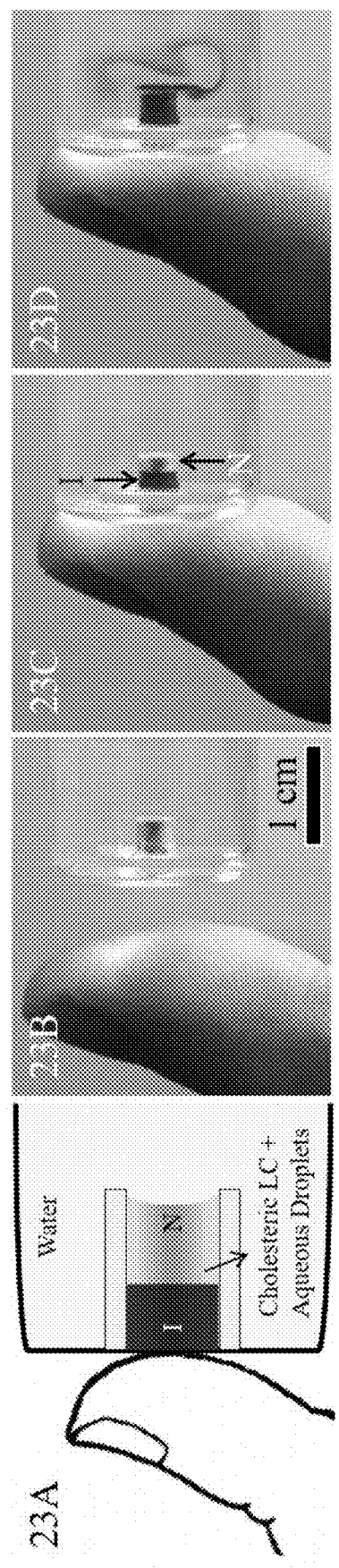
FIGURE 23A, 23B, 23C, and 23D

ACTIVATED RELEASE OF TARGET MATERIAL TRAPPED IN ANISOTROPIC FLUIDS

CROSS-REFERENCE TO RELATED APPLICATION

This application is a U.S. national phase entry of International Application No. PCT/US2017/037414 filed on Jun. 14, 2017, which claims the benefit of U.S. provisional Application No. 62/349,896 filed on Jun. 14, 2016. Each of these applications is incorporated by reference herein in its entirety.

STATEMENT REGARDING FEDERALLY SPONSORED RESEARCH OR DEVELOPMENT

This invention was made with government support under DMR1121288 awarded by the National Science Foundation and W911NF-15-1-0568 awarded by the ARMY/ARO. The government has certain rights in the invention.

FIELD

This disclosure relates generally to the controlled release of compositions sequestered within a fluid. In particular, the disclosure is directed to systems and methods for reducing and/or overcoming the elastic repulsion forces that prevent the release of guest compositions that are trapped within one or more anisotropic fluids, thus facilitating the release of such compositions from the fluids into the surrounding environment.

BACKGROUND

Technologies for controlled or on-demand release of one or more chemicals or compositions of interest from their place of storage have a wide range of potential applications, such as facilitating drug delivery, micro-cargo transport, development of responsive materials or smart packaging, development of antimicrobial surfaces, or use in microfluidics. Accordingly, various systems and methods have been developed for the controlled release of compositions of interest [1-18].

However, many previously proposed technologies for controlled release require performing complex procedures and/or using complex instrumentation, such as active delivery devices incorporating micrometer-scale chips, pumps, valves, and/or flow channels [19-24]. Thus, there is a need for new controlled release technologies that do not require the use of complex instrumentation, such as pumps, or complicated synthetic procedures.

Anisotropic fluids, such as liquid crystals (LCs), can trap and levitate immiscible guest compositions, such as drug-containing water droplets and solid microparticles, within their bulk. In the absence of external forces, the guest compositions (e.g., drug-containing water droplets) can remain sequestered within the LC bulk for extended periods of time, without any loss of the guest composition to the surrounding environment (e.g., an adjacent solution or solid substrate in contact with the LC bulk). The guest compositions remain sequestered within the LC bulk, because of elastic forces (i.e., elastic repulsion) between the guest composition droplets and each LC interface. Under normal storage conditions, these elastic repulsion forces are greater than any forces present tending to favor the release of the guest compositions from the LC bulk to the surrounding environment.

BRIEF SUMMARY

We have developed systems and methods for manipulating and/or overcoming the elastic repulsion forces that normally prevent immiscible guest compositions sequestered within an anisotropic fluid from being released into the surrounding environment. Here, we demonstrate that when the elastic repulsion forces are manipulated such that they are no longer sufficient to prevent release, and/or counter forces greater than the elastic repulsion forces are introduced that favor release of the guest compositions, the guest compositions are released from the anisotropic fluid. Because manipulating the elastic repulsion forces as needed and/or inducing the appropriate counter forces can be spatially and/or temporally controlled, the disclosed systems and methods can be used for on-demand or controlled release of immiscible guest materials that are sequestered within an anisotropic fluid.

Manipulation of elastic repulsion forces can occur by changing the molecular orientation or composition of the anisotropic fluid or by changing the surrounding environment (e.g., by changing the temperature). Exemplary counter forces that may be used to overcome the elastic repulsion forces preventing release include, e.g., elastic forces generated with an internal interface, interfacial tension force, buoyant forces, magnetic forces, osmotic forces, hydrodynamic forces, Marangoni stresses, interfacial shear stresses, optical forces, electrical forces and electrostatic attractions induced by the presence of charged substances (molecules, droplets or solid particles) within or in contact with the guest compositions and/or the surrounding environment.

Accordingly, in a first aspect, the disclosure encompasses a system for the controlled release of a guest composition sequestered within a host composition. First, the system includes a guest composition sequestered within a host composition made up of an anisotropic fluid. The guest composition is immiscible (or not soluble, if a solid or gas) in the host composition, thus forming an interface with the host composition upon which elastic repulsion forces act to prevent the release of the guest composition from the host composition. The interface can be deformable or rigid. Second, the system includes a device or composition for changing the elastic repulsion forces and/or introducing one or more counter forces such that the elastic repulsion forces are no longer sufficient to prevent the release of the guest composition from the host composition.

In some embodiments, the host composition is capable of undergoing an optically detectable change when the elastic repulsion forces are changed and/or one or more counter forces are introduced.

In some embodiments, the device or composition for changing the elastic repulsion forces and/or introducing one or more counter forces is a device capable of changing the temperature of at least part of the system. In some embodiments, the change of temperature leads to the propagation of an isotropic-nematic interface across the host composition. In some such embodiments, the device is a heating device, a cooling device, or a light source. In some such embodiments, the heating device or light source is positioned to differentially heat one portion of the host composition relative to another portion of the host composition, or the cooling device is positioned to differentially cool one portion of the host composition relative to another portion of the host composition. Exemplary light sources that could be used include, without limitation, an ultraviolet light source. In some embodiments where the device is a light source, the system may also include a light-absorbent dye. In some embodiments, the heating is achieved by the passage of electrical current through a resistor (Ohmic heating), in other embodiments, dissipative processes associated with the application of (AC or DC) electrical or magnetic fields can lead to heating, or hydrodynamic viscous dissipation can lead to heating. The scope of the disclosure is not limited by the means of achieving differential heating.

In some embodiments, the host composition includes a nematic-isotropic (N-I) phase transition. In some such embodiments, the N-I phase transition interface is propagated within the host composition.

In some embodiments, the device or composition for changing the elastic repulsion forces is a device capable of elevating the temperature of the system which lead to the decrease of the elastic repulsion forces to allow the release of the guest compositions from the host composition. In such embodiments, it is not necessary to have a gradient in heating. Either uniform or non-uniform heating can work. In some such embodiments, the device is a heating device or a light source. In some such embodiments, the heating device or light source is positioned to heat the host composition. Exemplary light sources that could be used include, without limitation, an ultraviolet light source. In some embodiments where the device is a light source, the system may also include a light-absorbent dye or other light-sensitive compound, such as a compound that changes conformation upon exposure to light. Non-limiting examples include azobenzene, a spiropyran, or cinnamic acid.

In some embodiments, the device or composition for introducing one or more counter forces is a guest composition having a different density than the host composition. In some such embodiments, the guest composition may have a lower density than the host composition.

In some embodiments, the device or composition for changing the elastic repulsion forces and/or introducing one or more counter forces is a device capable of inducing a shear stress at the interface of host composition.

In some embodiments, the device or composition for changing the elastic repulsion forces and/or introducing one or more counter forces is a magnetic or electric field source. In some such embodiments, the system includes one or more assistive particles capable of phasing parallel (or perpendicular) to a magnetic or electric field.

In some embodiments, the device or composition for changing the elastic repulsion forces and/or introducing one or more counter forces is a composition that includes one or more charged substances or molecules. In some embodiments, the composition containing one or more charged substances or molecules is positioned to be delivered to the environment outside of and adjacent to the host composition. In some such embodiments, the environment outside of and adjacent to the host composition comprises a recipient composition adjacent to and in contact with the host composition that is immiscible with the host composition, and the elastic repulsion forces in the host composition prevent the release of the guest composition into the recipient composition.

In some embodiments, the guest composition is charged, or the composition that includes one or more charged substances or molecules in contact with or within the guest composition. In some such embodiments, the guest composition or charged substances or molecules in contact with or within the guest composition are negatively or positively charged, and a separate composition that includes substances or molecules having a charge opposite the charge of the guest composition or charged substances or molecules in contact with or within the guest composition is positioned to be delivered to the environment outside of and adjacent to the host composition.

In some embodiments, the one or more charged substances or molecules include one or more amphiphiles one or more charged polymers, or a combination thereof. In some such embodiments, the one or more amphiphiles may include a negatively charged surfactant, a positively charged surfactant, or both.

In some embodiments, the device or composition for changing the elastic repulsion forces and/or introducing one or more counter forces is a composition that includes one or more ionic and/or non-ionic amphiphiles or one or more charged and/or non-charged polymers. In some embodiments, the composition containing one or more amphiphiles or one or more polymers is positioned to be delivered to the environment outside of and adjacent to the host composition. In some such embodiments, the environment outside of and adjacent to the host composition comprises a recipient composition adjacent to and in contact with the host composition that is immiscible with the host composition, and the elastic repulsion forces in the host composition prevent the release of the guest composition into the recipient composition prior to the addition of the amphiphile or polymer. The addition of the amphiphile or polymer leads to hydrodynamic force, electrostatic force, osmotic force, or a combination thereof that overcome the elastic repulsion forces, leading to the release of the guest composition.

In some embodiments, the composition for changing the elastic repulsion forces and/or introducing one or more counter forces such that the elastic repulsion forces are no longer sufficient to prevent the release of the guest composition from the host composition further comprises one or more solutes that are miscible in the host composition. In some such embodiments, the one or more solutes are isotropic solutes. Non-limiting examples include alcohols, ketones, aldehydes, fatty acids, aromatics, cyclic alkanes, or branched alkanes.

In some embodiments, the one or more solutes that are miscible in the host composition include a light-sensitive compound capable changing its conformation upon exposure to light. Non-limiting examples include azobenzene, spiropyran, and cinnamic acid.

In some embodiments, the composition for changing the elastic repulsion forces and/or introducing one or more counter forces is a composition that is capable of changing the pH of the environment adjacent to the host composition.

In some embodiments, the anisotropic fluid is a liquid crystal. In some such embodiments, the liquid crystal is in two different phases. In some embodiments, the liquid crystal is a nematic liquid crystal. In some embodiments, the liquid crystal is a chiral nematic (cholesteric) liquid crystal. In some embodiments, the liquid crystal is a thermotropic or lyotropic liquid crystal. In some embodiments, at least part of the liquid crystal is in the nematic (N) phase, and at least part of the liquid crystal is in the isotropic (I) phase.

In some embodiments, the composition for changing the elastic repulsion forces and/or introducing one or more counter forces such that the elastic repulsion forces are no longer sufficient to prevent the release of the guest composition from the host composition comprises one or more motile bacteria.

In some embodiments, the host composition does not comprise a lyotropic liquid crystal.

In some embodiments, the system includes two or more non-contiguous host compositions.

In some embodiments, the host composition has two or more different guest compositions sequestered within it.

In some embodiments, the density of the guest composition is different than the density of the host composition. In some such embodiments, the density of the guest composition is less than the density of the host composition.

In some embodiments, the guest composition includes a drug, a cleaning composition, an antiseptic agent, a bioactive agent, an aggregate of molecules, a chemoattractant, an antibiotic, an antibiofilm agent, a fragrance, a flavor, a cosmetic agent, an organism, a nanoparticle or microparticle, a liquid, a gel, a gas, a solid, or a composition capable of at least partially destroying, dissolving, or otherwise rendering an electronic or mechanical device unworkable.

In a second aspect, the disclosure encompasses a system for the controlled release of a guest composition sequestered within a host composition, the system that includes (a) a host composition made up of an anisotropic fluid; (b) a guest composition that is immiscible in the host composition that is at least partially sequestered within the host composition, forming an interface between the guest and host compositions upon which elastic repulsion forces act; and (c) one or more force-altering factors that are actively altering the elastic repulsion forces and/or introducing one or more counter forces to facilitate the controlled release of the guest composition from the host composition.

In some embodiments, the host composition undergoes an optically detectable change when the elastic repulsion forces are changed and/or one or more counter forces are introduced.

In some embodiments, the force-altering factors may include one or more of (i) a temperature differential from one portion of the host composition to another portion of the host composition; (ii) the host composition comprising two different phases delineated by a phase boundary; (iii) the guest composition having a different density than the host composition; (iv) the host composition being at an elevated temperature; (v) a shear stress at the interface of host composition; the shear stress could be caused by an imposed fluid flow, but the scope of the invention is not limited by the number of ways in which the shear stress can be imposed as many ways are known to those skilled in the art; (vi) one or more assistive particles capable of phasing parallel or perpendicular to a magnetic or electric field; (vii) one or more charged substances or molecules; (viii) one or more amphiphiles; (ix) one or more polymers; (x) one or more pH-changing agents; (xi) a light-absorbent dye or other light-sensitive compound; (xii) a solute that is miscible in and incorporated into the host composition; or (xiii) one or more motile bacteria.

In some embodiments, the force-altering factors present include the temperature differential or elevated temperature noted above, where either the host composition includes two different phases, or the guest composition has a different density than the host composition.

In some embodiments, the guest compositions have a lower density than the host composition.

In some embodiments, the force-altering factors present include one or more charged substances or molecules. In some such embodiments, the one or more charged substances or molecules are in contact with or within the guest composition. In some such embodiments, the system further includes one or more charged substances or molecules in the environment outside of and adjacent to the host composition that have an opposite charge to the charge of the one or more charged substances or molecules in contact with or within the guest composition. In some such embodiments, the environment outside of and adjacent to the host composition is a recipient composition that is immiscible (or insoluble) with the host composition.

In some embodiments, the charged substances or molecules present may include one or more amphiphiles. In some such embodiments, the one or more amphiphiles may include a positively charged surfactant, a negatively charged surfactant, or both.

In some embodiments, the charged substances or molecules present may include one or more charged polymers. In some such embodiments, the charged polymers are positioned to be delivered to or within the environment outside of and adjacent to the host composition.

In some embodiments, the one or more force-altering factors include one or more pH-changing agents. In some such embodiments, the pH-changing agents are positioned to be delivered to or within the environment outside of and adjacent to the host composition.

In some embodiments, the one or more force-altering factors include a light-sensitive compound that is incorporated into the host composition. The light-sensitive compound is capable of changing its conformation upon exposure to light. Non-limiting examples include azobenzene, spiropyran, and cinnamic acid.

In some embodiments, the one or more force-altering factors include a solute that is miscible in and incorporated into the host composition. In some such embodiments, the solute is an isotropic solute. Non-limiting examples include alcohols, ketones, aldehydes, fatty acids, aromatics, cyclic alkanes, and branched alkanes.

In some embodiments, the host composition is in the form of a droplet or a thin film.

In some embodiments, the anisotropic fluid is a liquid crystal. In some such embodiments, the one or more force-altering factors may include the liquid crystal being in two different phases.

In some embodiments, the liquid crystal is a nematic liquid crystal. In some embodiments, the liquid crystal is a chiral nematic (cholesteric) liquid crystal. In some embodiments, the liquid crystal is a thermotropic liquid crystal or lyotropic liquid crystal.

In some embodiments, at least part of the liquid crystal is in the N phase, while at least part of the liquid crystal may be in the I phase.

In some embodiments, the host composition does not include a lyotropic liquid crystal.

In some embodiments, the system includes two or more non-contiguous host compositions.

In some embodiments, the host composition has two or more different guest compositions at least partially sequestered within it.

In some embodiments, the guest composition may include a drug, a cleaning composition, an antiseptic agent, a bioactive agent, an aggregate of molecules, a fragrance, an organism, or a composition capable of at least partially destroying, dissolving, or otherwise rendering an electronic or mechanical device unworkable.

In a third aspect, the disclosure encompasses a method for controlled release of a guest composition of interest sequestered within a host composition made up of an anisotropic fluid. The guest composition is immiscible or insoluble in the host composition, thus forming an interface with the host composition upon which elastic repulsion forces act to prevent the release of the guest composition from the host composition. The method includes the step of changing the elastic repulsion forces and/or introducing one or more counter forces such that the elastic repulsion forces are no longer sufficient to prevent the release of the guest composition from the host composition. As a result of performing the method, at least a portion of the guest composition is released from the host composition into the surrounding environment.

In some embodiments, the host composition undergoes an optically detectable change as the elastic repulsion forces are changed or the one or more counter forces are introduced. In some such embodiments, the optically detectable change occurs contemporaneously with the release of the guest composition.

In some embodiments, the step of changing the elastic repulsion forces and/or introducing one or more counter forces includes changing the temperature of at least part of the host composition. In some such embodiments, changing the temperature of at least part of the host composition includes establishing a temperature differential from one portion of the host composition to another portion of the host composition. In some embodiments, a phase transition interface is propagated within the anisotropic fluid. In some embodiments, an elevated temperature is established for the host composition.

In some embodiments, the temperature is changed using a heating device, a cooling device, or a light source. Exemplary light sources that could be used include an ultraviolet light source. In some embodiments, wherein the temperature is changed using a light source, and the host composition, the guest composition, or both include a light-absorbent dye.

In some embodiments, the step of changing the elastic repulsion forces includes elevating the temperature of the host composition. In some embodiments, the temperature is changed using a heating device or a light source. Exemplary light sources that could be used include an ultraviolet light source. In some embodiments, wherein the temperature is changed using a light source, and the host composition, the guest composition, or both include a light-absorbent dye.

In some embodiments, the step of changing the elastic repulsion forces and/or introducing one or more counter forces includes introduction of shear flow in the environment outside of or adjacent to the host composition.

In some embodiments, the step of changing the elastic repulsion forces includes applying a magnetic or electric field to the host composition. In some such embodiments, the host composition includes one or more assistive particles capable of phasing parallel or perpendicular to a magnetic or electric field.

In some embodiments, the step of changing the elastic repulsion forces and/or introducing one or more counter forces includes changing the charge of the guest composition, and/or adding one or more charged substances or molecules to the guest composition, to the host composition, or to the environment outside of and adjacent to the host composition. In some such embodiments, the environment outside of and adjacent to the host composition is a recipient composition adjacent to and in contact with the host composition that is immiscible or insoluble with the host composition.

In some embodiments, the guest composition is negatively or positively charged, or one or more negatively charged substances or molecules or one or more positively charged substances or molecules are in contact with or within the guest composition, and the step of changing the elastic repulsion forces and/or introducing one or more counter forces includes adding one or more substances or molecules having a charge opposite to the charge of the guest composition or charged substances or molecules in contact with or within the guest composition to the environment outside of and adjacent to the host composition.

In some embodiments, the charged substances or molecules used may include one or more amphiphiles, one or more charged polymers, or one or more pH-changing agents. In some such embodiments, the one or more amphiphiles may include a negatively charged surfactant, a positively charged surfactant, or both.

In some embodiments, one or more solutes miscible in the host composition are added to the host composition or to the environment outside of and adjacent to the host composition. In some such embodiments, the solutes are isotropic. Non-limiting examples include alcohols, aldehydes, ketones, fatty acids, aromatics, cyclic alkanes, or branched alkanes.

In some embodiments, the step of changing the elastic repulsion forces and/or introducing one or more counter forces includes contacting one or more motile bacteria with the host composition, the guest composition, or the environment outside of or adjacent to the host composition.

In some embodiments, the host composition further includes a light-sensitive compound that is capable of changing conformation when exposed to light. In some such embodiments, the method includes the step of exposing the host composition to light, whereby the conformation of the light-sensitive compound is changed. Non-limiting examples of light-sensitive compounds that could be used include azobenzene, a spiropyran, or cinnamic acid. In some embodiments, the change in conformation is reversible. In other embodiments, the change in conformation is irreversible.

In some embodiments, the step of changing the elastic repulsion forces and/or introducing one or more counter includes changing the pH of the host composition or surrounding environment.

In some embodiments, the anisotropic fluid is a liquid crystal. In some such embodiments, the liquid crystal is in two different phases. In some embodiments, the liquid crystal used is a nematic liquid crystal. In some such embodiments, at least part of the nematic liquid crystal is in the N phase, and at least part of the nematic liquid crystal is in the I phase. In some such embodiments, the N-I phase transition is propagated within the host composition. In some embodiments, the nematic liquid crystal is s chiral nematic (cholesteric) liquid crystal.

In some embodiments, the host composition is not made up of a lyotropic liquid crystal.

In some embodiments, the method is applied to two or more non-contiguous host compositions having guest compositions sequestered within them.

In some embodiments, the method is applied to a host composition having two or more different guest compositions sequestered within it.

In some embodiments, the density of the guest composition is different than the density of the host composition. In some such embodiments, the density of the guest composition is less than the density of the host composition.

In some embodiments, the guest composition includes a drug, a cleaning composition, an antiseptic agent, a bioactive agent, an aggregate of molecules, a fragrance, an organism, or a composition capable of at least partially destroying, dissolving, or otherwise rendering an electronic or mechanical device unworkable.

Other objects, features and advantages of the present invention will become apparent after review of the specification, claims and drawings.

BRIEF DESCRIPTION OF THE DRAWINGS

FIGS. 1A, 1B, 1C, 1D, 1E, 1F, 1G, 1H, 1I, and 1J show repeated ejection of pulses of dispersed guest droplets from a nematic LC triggered by the N-I phase transitions. FIG. 1A shows the molecular structure of the representative liquid crystal, 5CB (left), along with micrograph of aqueous guest droplet in 5CB (right) with a reconstructed director profile (middle). Each droplet is of a homeotropic surface anchoring due to the doped surfactant, sodium dodecyl sulfate (SDS), and thus is accompanied with a point defect. FIG. 1B is a schematic diagram of the exemplary system for the controlled release activated by the N-I phase transitions. FIGS. 1C-1F are sequential photographs of the system in the initial N phase (1C) and after N-to-I 1D), I-to-N (1E), and (I-to-N) (1F) phase transitions; the heating $T_H$ and cooling $T_C$ temperatures were 50° C. and 25° C., respectively. The concentrations of aqueous droplets ($C_{aq}$) dispersed in 5CB and SDS ($C_{SDS}$) doped in the droplets are 20 v % and 9 mM, respectively. FIGS. 1C and 1D also include an inset with micrographs of the miniwell showing the optical responses accompanied with the release of the microdroplets. FIGS. 1G and 1H show the absorbance A of the water bath measured at a wavelength corresponding to peak tracer absorbance ($\lambda_{Red}$=510 nm), as a function of time before phase transitions at temperature T=25° C. (1G) and after a N-to-I phase transition (after heating to T=50° C., 1H). FIGS. 1I and 1J show A with respect to the number of phase transitions (1I) and $C_{aq}$ after 20 phase transitions (1J). Absorbance spectra of FIGS. 1G and 1I are shown in FIGS. 2A and 2B.

FIG. 2A shows absorbance spectra of the water bath at T=25° C. (without phase transitions) 0, 24, 48, 72, and 96 hours after the mini-well was submerged into the bath. FIG. 2B shows absorbance spectra of the water bath with respect to the number of phase transitions with $T_H$=50° C. and $T_C$=25° C.; the release of microdroplets were activated upon both heating and cooling.

FIGS. 3A-G are sequential photographs for the release of tracer ($C_{aq}$=20 v %, $C_{SDS}$=9 mM) triggered by N-I phase transitions using Joule heater; 30 V for heating ($T_H$=60° C.) and 0 V for cooling (to room temperature). Heating of the sample from below was achieved by passage of current through an indium thin oxide electrode coated on glass. The motion of the N-I interface was upward-directed for both heating and cooling.

FIG. 4A shows propagation of the N-I interface from the LC-glass interface (bottom) to the LC-water interface (top) upon heating from T=25° C. to $T_H$=50° C. (N-to-I phase transition). Upon heating, the interface moves upward regardless of $T_H$ and microdroplets were ejected (FIGS. 1D and 1H). FIG. 4B shows upward propagation of the N-I interface upon cooling from 50° C. to $T_C$=25° C. (I-to-N phase transition) and release of microdroplets (FIGS. 1E and 1I). FIG. 4C shows downward propagation of the N-I interface upon cooling from 50° C. to $T_C$=35° C. and the absence of release of tracers. A and absorbance spectra of FIG. 4C are shown in FIGS. 5A and 5B. Red and blue arrows indicate the propagation direction of the interface.

FIGS. 5A and 5B show A (5A) and the corresponding absorbance spectra (5B) with respect to the number of phase transitions upon $T_H$=50° C. and $T_C$=35° C.; $C_{aq}$=10 v % ($C_{SDS}$=9 mM). The absorbance measurements show that microdroplets containing tracer were ejected during the upward motion (heating) but not downward motion (cooling) of the N-I interface.

FIGS. 6A, 6B, 6C, 6D, 6E, 6F, 6G, and 6H show the transport of the guest droplets in a size-dependent manner by elastic repulsion forces associated with a moving N-I interface. FIGS. 6A-6H are sequential micrographs (6A-6D) and corresponding illustrations (6E-6H) of the transport of small microdroplets (dotted circles; R<R*) but not large droplets (solid circles; R>R*) by a moving N-I interface (yellow arrows) upon heating; $C_{aq}$=0.5 v %, $C_{SDS}$=9 mM, and $v_{NI}$=10 μm/s.

FIGS. 7A, 7B, 7C, 7D, 7E, 7F, 7G, 7H, 7I, 7J, 7K, 7L, 7M, 7N, 7O, 7P, 7Q, and 7R show behaviors of clusters of microdroplets during passage of the N-I interface and evidence that droplets with R>R* are not transported by the N-I interface. FIGS. 7A-7H are sequential micrographs showing behaviors of clusters of microdroplets during passage of a N-I interface during either a N-to-I (heating, 7A-7D) or I-to-N (cooling, 7E-7H) phase transition. $v_{NI}$=10 μm/s for heating, 35 μm/s for cooling, and R*~10 μm for both cases. Red and blue arrows indicate the direction of motion of the N-I interface. Solid and dotted circles indicate droplets with R>R* (=10 μm) and R<R*, respectively. White arrows indicate the droplets that coalesced while being transported by the moving N-I interface. Note that droplets with R<R* are left behind the N-I interface in 7C because they are shed from clusters, as illustrated in 7I-7L. FIGS. 7I-7L are illustrations of a droplet cluster being transported by a moving N-I interface. FIG. 7I shows that single droplets or droplet clusters with R<R* are transported by a moving N-I interface. FIG. 7J shows that as the moving interface collects more droplets, the clusters of droplets formed at the interface increase in size. FIG. 7K shows that when the effective radius of droplet cluster exceeds R*, the interface no longer transports the cluster. FIG. 7L shows that as some of droplets from the cluster are left behind the N-I interface, the cluster becomes smaller than R* and thus is transport again by the interface. FIG. 7M-7R show the evidence that droplets with R>R* are not transported by the N-I interface moving at high speed ($v_{NI}$=100 μm/s) during N-to-I (7M-7O) and I-to-N phase transitions (7P-7R). The left and right columns, respectively, show optical micrographs before and after passage of the N-I interface, and the middle column shows micrographs during passage of the N-I interface. The positions of microdroplets before and after the passage of the N-I interface are unchanged, revealing that R>R* for the rapidly moving interface.

FIGS. 8A and 8F show the microdroplets that were dispersed initially in the LC bulk. FIGS. 8B and 8G show that when the bottom of the micro-well was heated to $T_H$=50° C. (>$T_{NI}$), the N-to-I phase transition first occurs at the LC-glass interfaces (denoted by * in 8B) and the N-I interface propagates upward toward the LC-water interface. FIGS. 8C and 8H show that droplets that were out of focus (red dotted circles in 8A) moved into focus revealing that the moving interface transported the droplets toward the LC-water interface. FIGS. 8D and 8I show that as the N-I interface reaches the LC-water interface, the droplets disappeared, consistent with the fusion of droplets with the overlying aqueous phase. FIGS. 8E and 8J show that after the release, the reduced number of droplets remains.

FIG. 10A is an illustration of the inverted mini-well for the release of microdroplets ($C_{aq}$=10 v %, $C_{SDS}$=9 mM) from an isotropic phase of 5CB. FIGS. 10B-10G are sequential photographs of the mini-wells filled with 5CB containing the guest droplets with $\rho_{5CB}<\rho_{aq}$ (10B-10D) and $\rho_{5CB}=\rho_{aq}$ (10E-10G) at 0 (10B, 10E), 1 (10C, 10F), and 24 hours (10D, 10G) after the baths were heated to T=45° C. (>$T_{NI}$).

FIGS. 11A-11D are sequential photographs for the continuous release of microdroplets at 0 (11A), 15 (11B), 60 (11C), and 120 minutes (11D) after the bath was heated to $T_H$=59° C. (<$T_{NI}$); $C_{aq}$=30 v %, $C_{SDS}$=2 mM, and $\rho_{E7}>\rho_{aq}$. FIG. 11E is time-dependent A at representative temperatures T=40° C., 50° C., and 59° C. FIG. 11F is an illustration of forces acting on an aqueous droplet in E7. FIG. 11G show total forces $F^T$ acting on the droplet as a function of R at h=0 at the representative temperatures. Positive force implies that the droplets can penetrate the LC-water interface, thereby being released into the water bath.

FIGS. 12A, 12B, 12C, 12D, 12E, 12D, 12E, 12F, 12G, 12H, 12I, 12J, 12K, 12L, 12M, 12N, and 12O shows the influence of the size and clustering of microdroplets on continuous release from LC triggered by an elevated temperature. FIGS. 12A-12F show sequential micrographs of microdroplets with R=9.5 μm (12A-12C) or 27 μm (12D-12F) in E7 at 25° C. (12A, 12D), 50° C. (12B, 12E), and 59° C. (12C, 12F); $\rho_{E7}>\rho_{aq}$ and $C_{aq}$=1 V % ($C_{SDS}$=2 mM). The droplet was elastically trapped in the nematic LC bulk at 25° C. As the temperature increased to 50° C. (R>34 μm for release), the droplets moved upwards and into focus but were not dispensed into the overlying water; the focal plane was near overlying water-LC interface. At 59° C. (R>23 μm for release), we observed the larger droplet (R=27 μm) to escape into the aqueous phase while the smaller droplet (R=9.5 μm) remained elastically trapped in the nematic bulk. This observation is in good agreement with our theoretical prediction (FIG. 11G). FIGS. 12G-12I show sequential micrographs of the clustering of microdroplets dispersed in a LC at 0 (12G), 30 (12H), and 180 minutes (12I); $C_{aq}$=2 v % ($C_{SDS}$=9 mM). FIGS. 12J-12O show the illustration (12J) and sequential micrographs (12K-12O) from mini-wells filled with E7 containing microdroplets having different sizes, at 0 (12K), 7 (12L), 10 (12M), 12 (12N), and 15 minutes (12O) after the baths were heated to $T_H$=59° C. ($T_{NI}$); $\rho_{E7}>\rho_{aq}$ ($F_B>0$) and $C_{aq}$ 20 v % ($C_{SDS}$=9 mM). The mini-well containing the microdroplets having the larger size (left bath) exhibited a higher release due to the facile formation of droplet clusters with the radius above which $F^T>0$, consistent with the theoretical model in FIG. 11G.

FIGS. 13A, 13B, 13C, and 13D illustrate the release of microdroplets triggered by a shear flow in a surrounding environment. FIGS. 13A-13D are time sequential photographs of the release of microdroplets ($C_{aq}$=20 v %, $C_{SDS}$=9 mM) at 0 (13A), 10 (13B), 20 (13C), and 30 minutes (13D) after a shear flow was generated in surrounding aqueous phases by stirring magnetic bar.

FIGS. 14A-14D are sequential photographs of a solute-triggered N-to-I phase transitions of 5CB at T=25° C. ($T_{NI}^{5CB}$=35° C.) at 0 (14A), 1 (14B), 2 (14C), and 3 hours (14D) after propanol was added to the water bath. As the propanol diffused into the 5CB, a N-to-I transition occurred first at the LC-water interface and propagated into the LC bulk. FIGS. 14E-14H show an illustration (14E) and sequential photographs (14F-14H) of the system at 0 (14F), 5 (14G), and 30 minutes (14H) after the wells were submerged into the baths. Although $F_B$ ($\rho_{LC}<\rho_{aq}$) promotes the release of tracers, no release was observed in the left bath due to a strong elastic sequestration. In the right bath, however, the red tracers were continuously released as the elastic barrier is removed by the solute-induced N-to-I phase transition. $C_{Propanol}$=16 v % and $C_{aq}$=10 v % ($C_{SDS}$=9 mM)

FIG. 15A shows the illustration of forces acting on the aqueous microdroplet. FIGS. 15B-15D are time sequential photographs of the continuous ejection of microdroplets ($C_{aq}$=20 v %) from a mini-well filled with a nematic LC at 0 (15B), 0.5 (15C), and 10 hours (15D) in the water baths with $C_{DTAB}$=2 (left bath), 5 (middle bath), and 10 mM (right bath). FIG. 15E shows A for tracer released from mini-wells in the baths with water, SDS-water, and DTAB-water. FIG. 15F shows zeta potential ξ at LC-aqueous interfaces without amphiphiles (white bar) and with SDS (grey bar) or DTAB (green bars).

FIGS. 16A-16H are sequential micrographs (top view, 16A-16D) and corresponding illustrations (side view, 16E-16H) for the isothermal release from a micro-well before (16A, 16E) and after the addition of DTAB at 0 (16B, 16F), 30 (16C, 16G), and 60 minutes (16D, 16H). The release is accompanied by an optical response of the LC from a bright to a dark appearance. FIGS. 16I-16K show the isothermal release from a LC emulsion before (16I) and after the addition of DTAB at 50 (16J) and 80 seconds (16K). Insets in 16I and 16J are optical micrographs (crossed polarizers) of the LC droplet showing the optical response.

FIGS. 17A, 17B, 17C, 17D and 17E illustrate the role of the electrostatic interaction in the release of microdroplets from a nematic LCs. FIGS. 17A-17D are time sequential photographs for the ejection of microdroplets ($C_{aq}$=20 v % and $C_{SDS}$=9 mM) triggered by the N-I phase transitions in the baths with SDS-water ($C_{SDS}$=2 mM, left bath), pure water (middle bath), and DTAB-water ($C_{DTAB}$=2 mM, right bath) before phase transitions (17A) and after 2 (17B), 6 (17C), and 10 phase transitions (17D); $T_H$=50° C. and $T_C$=25° C. FIG. 17E show corresponding A as a function of the number of phase transitions.

FIGS. 18A-18C are the schematic diagram (18A) and photographs (18B and 18C) for the release of green tracer ($C_{aq}$=20 v %, $C_{DTAB}$=9 mM) from Well 1 accompanies addition of SDS and triggering of phase transitions ($1^{st}$ to $4^{th}$ phase transition). FIGS. 18B and 18C are the photographs after 2 and 4 phase transitions, respectively. FIGS. 18D-18F are the schematic diagram (18D) and photographs (18E and 18F) for the release of red tracer ($C_{aq}$=20 v %, $C_{SDS}$=9 mM) from Well 2 accompanies addition of DTAB and triggering of phase transitions ($5^{th}$ to $8^{th}$ phase transition). FIGS. 18E and 18F are the photographs after 6 and 8 phase transitions. FIG. 18G show corresponding A as a function of the number of phase transitions.

FIG. 19A is an illustration of the system for the polymer-triggered release. FIG. 19B is a molecular structure of exemplary polymer, Polydiallyldimethylammonium chloride (PDADMAC). FIGS. 19C and 19D are sequential photographs of the release of microdroplets from a mini-well at 0 (19C) and 4 hours (19DC) after the addition of PDADMAC into the bath; $C_{aq}$=30 v % ($C_{SDS}$=2 mM). FIG. 19E shows the corresponding time-dependent A with respect to $C_{Polymer}$.

FIGS. 20A, 20B, 20C, 20D, 20E, 20F, 20G, 20H, and 20I demonstrate the triggering of release of microdroplets based on interfacial charge interactions of biological molecules. Aqueous microdroplets dispersed in the LC contained DTAB ($C_{DTAB}$=2 mM) and the charge of the interface between the LC and the bulk aqueous phase was manipulated by addition of lipopolysaccharides (LPS), from *Escherichia coli*, to the bulk aqueous phase: FIG. 20A is a measured Zeta potential ν at LC-aqueous interface without (white bar) and with LPS (green bars) or DTAB (grey bar). FIGS. 20B-20I are sequential micrographs of the ejection of microdroplets containing anti-bacterial agent (DTAB) from LC as a function of $C_{LPS}$ at 0 (20B), 1 (20C), 2 (20D), 4 mg/ml (20E) and before (20F) and after the addition of LPS into the bulk aqueous phase at 0 (20G), 15 (20H), 30 minutes (20I); $C_{aq}$=10 v %. P and A indicate orientations of the polarizer and analyzer, respectively.

FIG. 21A are illustration of inverted mini-wells in baths of water (pH 7, left bath) and alkaline water (pH 13, right bath) at T=45° C. (>$T_{NI}$); $C_{aq}$=10 v % ($C_{SDS}$=9 mM) in 5CB. FIGS. 21B and 21C are sequential micrographs of the mini-wells at 0 (21B) and 60 minutes (21C) after a N-to-I phase transition. Since $\rho_{LC}$<$\rho_{aq}$ ($F_B$<0), tracers were continuously released from an isotropic phase of 5CB ($F_E$=0) in the pure water (left bath). In the alkaline water (right bath), however, the release was suppressed because of the introduction of repulsive charge interactions between the LC interface in alkaline water (negatively charged) and SDS-containing aqueous droplets (negatively charged).

FIGS. 22A, 22B, 22C, 22D, 22E, and 22F illustrate the release of microdroplets triggered by Marangoni convection flow in a LC. FIGS. 22A and 22B are micrographs of 5CB contacting with pure water (22A) and Triton-water solution ($C_{Triton}$=10 mM, 22B). When a LC is in contact with pure water, no material flow was observed while a strong convection flow was induced in the LC contacting with the triton-water solution. FIGS. 22C-22F are time sequential photographs of the convection flow-triggered release of microdroplets ($C_{aq}$=20 v %, $C_{SDS}$=9 mM) at 1 (22C), 5 (22D), 30 (22E), and 150 minutes (22F) after the mini-wells were submerged in the water baths with $C_{Triton}$=5 (left bath), 10 (middle bath), and 100 mM (right bath).

FIGS. 23A, 23B, 23C, and 23D illustrate the release of microdroplets triggered by a physiological temperature. FIGS. 23A-23D are schematic illustration (23A) and sequential photographs (23B-23D) for release of microdroplets ($C_{aq}$=10 v %, $C_{SDS}$=2 mM) from cholesteric LC triggered by the touch of a finger causing a N-to-I phase transition.

FIGS. 24A-24F are polarizing—(24A, 24D) and fluorescence-micrographs (24B, 24E), and schematic illustrations (24C, 24F) of cross-section of a LC film (40 μm in thickness) at 25° C. in the initial N phase (24A-24C) and after 6 phase transitions (24D-24F); $T_H$=50° C. and $T_C$=25° C. The LC film (5CB) containing solid microparticles of FITC-dextran (1-2 v %). FIG. 24G is a fluorescence micrograph of the overlying water phase before phase transitions. No fluorescent signal is detected implying that the microparticles were trapped in a LC layer. FIG. 24H is the same after 6 phase transitions. After phase transitions, the overlying aqueous phase showed a strong fluorescent signal, implying the ejection of microparticles. Inset graph shows a fluorescent intensity $I_F$ as a function of the number of phase transitions.

FIG. 25A is a schematic diagram for the selective release. Well 1 (in the left bath) and Well 2 (in the right bath) were filled with 5CB ($T_{NI}^1$=35° C.) and the mixture of 5CB+E7 (7:3, $T_{NI}^2$=42.5° C.) containing aqueous droplets ($C_{aq}$=20 v %, $C_{SDS}$=9 mM), respectively; $\rho_{LC}$<$\rho_{aq}$. FIGS. 25B-25F are the sequential photographs for the selective release of microdroplets with Well 1 and Well 2. FIG. 25B shows that at 25° C., there is no release of microdroplets from both Well 1 and Well 2. FIGS. 25C and 25D show the release of microdroplets from the Well 1 after the baths were heated from 25° C. to $T_H$=40° C. (25C) and were subsequently cooled f $T_C$=25° C. (25D). The release was not activated from Well 2 because $T_H$ (=40° C.)<$T_{NI}^1$ (=35° C.). FIGS. 25E and 25F show the release of microdroplets from both Well 1 and Well 2 after the baths were heated from 25° C. to $T_H$=45° C. (25E) and were subsequently cooled to $T_C$=25° C. (25F); $T_H$ (=45° C.)>$T_{NI}^1$ (=35° C.)>$T_{NI}^2$(=42.5° C.).

FIGS. 26A-26D are illustration (26A) and sequential photographs (26B-26D) for release of microdroplets containing anti-bacterial agent (DTAB) and red tracer, as triggered interfacial shear forces of motile bacteria ($10^7$-$10^8$ cells/ml); 0 (26B), 6 (26C), and 600 seconds (26D). FIGS. 26E-26J are sequential micrographs for no microdroplets were ejected from the LC in the absence of bacteria (26E-26G) or in the presence of weakly motile bacteria (26H-26J); 0 (26E, 26H), 15 (26F, 26J), and 30 minutes (26G, 26J). FIG. 26K show changes in optical responses at a LC interface with (blue line) and without bacteria (red). Insets are optical micrographs (crossed polarizers) at the LC interfaces with (blue dotted box in 26D) and without bacteria (red dotted box in 26G).

DETAILED DESCRIPTION

I. In General

Figures 2A, 2B:
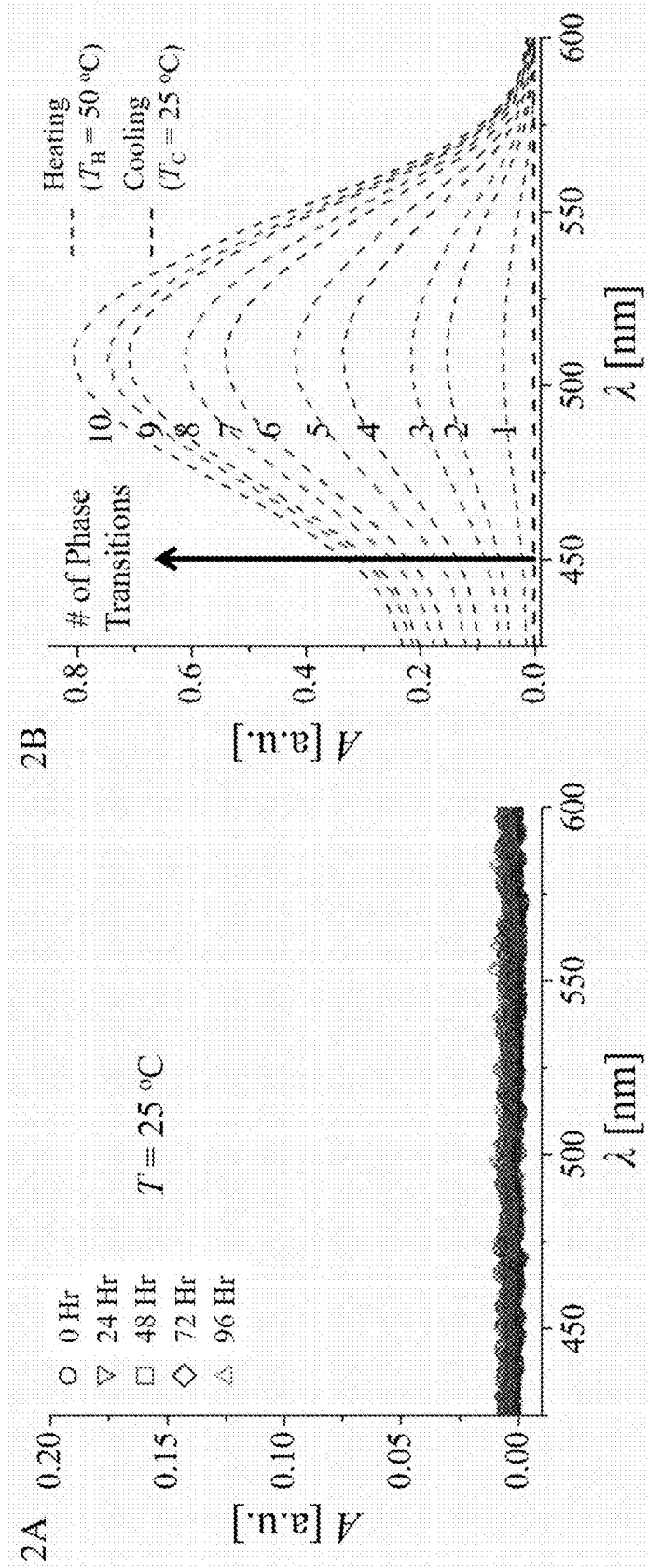
FIGS. 2A and 2B show the absorbance spectra for FIGS. 1G and 1I, respectively.

Before the present materials and methods are described, it is understood that this disclosure is not limited to the particular methodology, protocols, materials, and reagents described, as these may vary. It is also to be understood that the terminology used herein is for the purpose of describing particular embodiments only, and is not intended to limit the scope of the present disclosure.

As used herein and in the appended claims, the singular forms "a", "an", and "the" include the plural forms unless the context clearly dictates otherwise. As well, the terms "a" (or "an"), "one or more" and "at least one" can be used interchangeably, and the terms "comprising," "including," and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, exemplary methods and materials are now described.

All publications and patents specifically mentioned herein are incorporated by reference for all purposes including describing and disclosing the chemicals, instruments, statistical analysis and methodologies which are reported in the publications which might be used in connection with the disclosed systems and methods. All references cited in this specification are to be taken as indicative of the level of skill in the art.

As used herein, "liquid crystal" means an organic composition in an intermediate or mesomorphic state between solid and liquid. Suitable liquid crystals for use in the disclosed systems and methods include, but are not limited to, thermotropic, polymeric, lyotropic, chromonic, active, smectic, nematic, twist-bend nematic, ferroelectric, blue phase, and cholesteric liquid crystals.

As used herein, "lyotropic liquid crystal" are liquid crystals having a long-ranged orientational order that is induced by the addition of a solvent. Typically, lyotropic liquid crystals are made up of amphiphiles, such as fatty acid salts, phospholipids or other lipid-based substances.

As used herein, "anisotropic fluid" means a fluid having one or more properties that are directionally dependent, i.e., dependent on the angle from which the property is observed. Although the classic example of an anisotropic fluid is a liquid crystal, anisotropic fluids are not limited to liquid crystals.

II. The Disclosed Systems and Methods

Immiscible or insoluble guest compositions sequestered within an anisotropic fluid host composition can be held within the host composition for long periods of time, without being released into the surrounding environment. Such sequestration is maintained by elastic repulsion forces acting at the interface of the host and guest compositions.

We disclose herein systems and methods for manipulating and/or overcoming the elastic repulsion forces that normally prevent release of sequestered guest compositions to the surrounding environment. In the disclosed systems and methods, the elastic repulsion forces are manipulated such that they are no longer sufficient to prevent release, and/or counter forces greater than the elastic repulsion forces are introduced that favor release of the guest materials. As a result of these triggering actions, the guest materials are released from the anisotropic fluid host composition into the surrounding environment.

Because manipulating the elastic repulsion forces as needed and/or inducing the appropriate counter forces can be spatially and/or temporally controlled, the disclosed systems and methods can be used for on-demand or controlled release of any immiscible or insoluble guest composition that is sequestered within an anisotropic fluid host composition. Such systems and methods have numerous potential applications, including, without limitation, controlled delivery of pharmaceuticals and other bioactive compositions, cleaning compositions, antiseptic compositions, fragrances, dyes, compositions containing one or more organisms, or corrosive compositions designed to dissolve, erode or damage materials on contact.

A. Host Compositions

The host composition is primarily made up of one or more anisotropic fluids, although it may also contain other substances. However, the composition as a whole must act as an anisotropic fluid, in that it must exhibit differences, when measured along different axes, in one or more physical or mechanical properties (e.g., absorbance, refractive index, conductivity, shear strength, viscosity, etc.). Although liquid crystals are perhaps the most widely-recognized class of anisotropic fluids, anisotropic fluids that can be used are not limited to liquid crystals.

In addition to non-liquid crystal anisotropic fluids, various liquid crystals may be employed in the host compositions, including, without limitation, lyotropic and thermotropic liquid crystals. Polymeric liquid crystals are also suitable for use as host compositions. Numerous phases of liquid crystal suitable for use in the host compositions include, but are not limited to, nematic, twist-bend nematic, ferroelectric, smectic (e.g., smectic A, smectic C, and smectic C*), blue phases, and cholesteric phases. Specific examples of suitable liquid crystals include, but are not limited to, 4-cyano-4'-pentylbiphenyl (5CB), 7CB, and 8CB, E7 and TL205. A large listing of suitable liquid crystals is presented in "Handbook of Liquid Crystal Research" by Peter J. Collings and Jay S. Patel, Oxford University Press, 1997, ISBN 0-19-508442-X, which is incorporated by reference herein.

In certain embodiments, the host composition may include two or more different anisotropic fluids, and/or two or more different phases of a given fluid. In a non-limiting example, the host composition may include both the nematic phase and the isotropic phase of a fluid. These two phases (and a phase boundary at the interface between the phases) may be established when part of the fluid is at a temperature that is above (or below) the nematic-isotropic phase transition temperature, while another part of the fluid is at a temperature that is below (or above) the phase transition temperature.

In certain embodiments, the systems and methods may include two or more separate host compositions. They may each have the same make-up, or they may be made up of completely different anisotropic fluids, allowing the selective delivery of guest compositions from one or more of the host compositions using triggering event that are specific to the host compositions sequestering the guest composition of interest.

In certain embodiments, the host composition includes one or more solutes that are soluble in or miscible in the anisotropic fluid or fluids contained within the host composition. These soluble solutes may themselves be isotropic or anisotropic in nature. In such embodiments, the presence of a miscible solute can change the elastic repulsion forces, and thus can be used to facilitate the controlled release of the guest compositions sequestered within the host composition. Solutes that could be used for this purpose include, without limitation, one or more isotropic solutes, such as alcohols, fatty acids, ketones, ethers, aldehydes, ketones, aromatics, cyclic alkanes, or branched alkanes. As a non-limiting example, Example 4 illustrates that as a propanol solvent is diffused into a host composition (5CB), an N-to-I phase transition is induced to reduce the repulsive elastic force, thus facilitating the release of the guest composition.

In some embodiments, one or more of the soluble solutes included in the host composition may have two or more isomeric forms that have different effects on the ordering and/or or elastic repulsion forces contained within the host composition. Thus, the conversion from one isomeric form to the other, which may be reversible or irreversible, can be used to facilitate controlled release of the guest composition from the host composition.

In some such embodiments, the soluble solute may be a light-sensitive compound that reversibly or irreversibly isomerizes upon exposure to light. Non-limiting examples include (a) azobenzene, which reversibly isomerizes from the lower energy trans form to the higher energy cis form upon exposure to ultraviolet light; (b) spiropyrans, which reversibly isomerize upon exposure to ultraviolet light to the open-ringed merocyanine form; and (c) cinnamic acid, which irreversibly isomerizes form the trans form to the cis form upon exposure to light.

Other chemistries for aligning anisotropic fluids such as those that make up the host compositions are known in the art, and can be used to change elastic repulsion forces and/or anisotropic fluid ordering within the host composition in way that would facilitate controlled release of the guest composition. Such chemistries can be readily combined to create a "sentient" host composition capable of responding to environmental stimuli in a way that can be used to temporally and/or spatially control the release of the sequestered guest composition.

The specific geometry of the host composition is not limited, and may include, without limitation, droplets, thin films, or larger bulk shapes.

B. Guest Compositions

The guest compositions used must be immiscible or insoluble in the host compositions in which they are sequestered, but are otherwise not limited. Guest compositions may be solids, liquids, or gases, and may contain a single substance or a mixture of many substances. Furthermore, there may be multiple guest compositions (having the same or different makeup) within a single host composition, or spread among multiple host compositions, as noted above.

Exemplary guest compositions may include, without limitation, solids, gases, aqueous or other dyes, substances of synthetic or biological origin, pharmaceuticals and other bioactive substances, cleaning compositions, antiseptic substances, antimicrobial agents, local anesthetics, agents that facilitate wound healing, fragrances, compositions containing one or more organisms (e.g., lipopolysaccharide (LPS)-containing organisms), or corrosive compositions designed to dissolve, erode or damage materials on contact.

C. Exemplary Release Triggers

In the disclosed systems and methods, controlled or on-demand release of the guest compositions sequestered within the host compositions is accomplished using one or more triggers that (a) manipulate the elastic repulsion forces preventing release of the guest composition such that they are no longer sufficient to prevent release of the guest composition, or (b) introduce counter forces sufficient to overcome the elastic repulsion forces preventing release of the guest composition, or (c) some combination of the two.

A variety of triggers can be used to accomplish this, each of which can be tuned to precisely deliver a specific amount of guest composition to the surrounding environment at a specific time. Furthermore, the different triggers can be combined with the use of different host compositions and guest compositions, as described above, to create systems to selectively or differentially release different compositions, different quantities of the compositions, at different release rates, at different places, and/or at different times. Possible triggers for controlled release include both physical stimuli and chemical stimuli.

1. Physical Stimuli

Physical stimuli can trigger release in a number of different ways. For example, N-I phase transition induced by changing the temperature of at least part of the host composition cause the propagation of N-I interface which can transport the guest composition across the host composition to the recipient composition adjacent to and in contact with the host composition. In addition, elevating the temperature of the host composition lower the strength of the elastic repulsion forces sequestering the guest composition within the host composition and thus would facilitate release of the guest composition. Mechanical shear at LC interfaces can also lower the elastic barriers or provide counter forces to the guest composition to override the elastic repulsions and thus trigger the ejection of guest compositions from the host composition to the recipient composition. The mechanical stresses can be generated in a variety of ways, including shear flow in the recipient composition, motion of motile bacteria, the motion of an eye lid, contact with a human finger, and shear forces imparted by the feet of insects. In the non-limiting examples below, we illustrate this in more detail.

In Example 1, we demonstrate how changing the temperature of a nematic liquid crystal host composition past the phase transition temperature where the phase of the liquid crystal changes from the nematic phase to the isotropic phase (or vice versa) can promote one or more moving phase boundaries that can physically sweep one or more sequestered guest composition into the surrounding environment, thus overcoming the elastic repulsion forces preventing release. The extent of the thermal gradient established can be manipulated to control the movement of the phase boundary, and thus to control the rate of release.

In Example 2, we demonstrate that elevating temperature of a nematic liquid crystal host composition can be used to trigger release, even in the absence of moving phase boundaries and phase transitions. Specifically, the guest composition used in Example 2 had a lower density than the surrounding nematic liquid crystal host composition, and as a result, a buoyant force was established that acted to counter the elastic repulsion forces that initially prevented release of the guest composition. As the nematic liquid crystal was heated, the elastic repulsion forces were reduced, until the buoyant force was sufficient to overcome the elastic repulsion forces, thus triggering release of the guest composition. Again, the densities and temperature gradients that are established can be manipulated to control the rate of release.

The temperature of the host composition may be changed in variety of ways that would be readily apparent to one skilled in the art. Conventional heating and cooling devices, including without limitation, heaters of various types using electrical resistance and cooling devices incorporating various refrigerants, may be used.

Other methods known in the art may also be used to change the temperature of part or all of the host composition. In certain embodiments, the compositions may be exposed to ultraviolet light. Various other optical methods, such as incorporating light-absorbing dyes into the compositions and exposing the compositions to light, could be used. When exposed to light, the light-absorbing dyes undergo reversible photoisomerization which lead to a phase transition. When the newly-formed isomer reverts back to its original form, heat is released.

In Example 3, we demonstrate that shear flow introduced in a surrounding environment can trigger the release of guest compositions from a host composition in the absence of temperature changes.

Mechanical stimuli triggers are not limited to changing the temperature of the compositions used and introducing shear stresses at the interface of host compositions. As an alternative example, a magnetic (or electric) field may be applied to the host composition. In such an embodiment, the host and/or guest compositions may incorporate one or more diamagnetic (or dielectric) assistive particles capable parallel or perpendicular to the magnetic (or electric) field. As the assistive particles move in response to the applied magnetic (or electric) field, they provide a counter force capable of overcoming the elastic repulsion forces preventing the release of the guest composition. The strength and direction of the magnetic (or electric) field and the nature and concentration of the assistive particles present can be manipulated to control the rate of release.

2. Chemical Stimuli

Chemical stimuli can also trigger release in a number of different ways. For example, the addition of an isotropic solute (propanol) into the host composition can induce a N-to-I phase transition of host composition, thus facilitating the release of guest composition by eliminating the elastic repulsion forces. In addition, if the guest composition is coated with positively or negatively charged substances, the introduction of substances of opposite charge into the surrounding environment can induce an electrostatic attraction sufficient to overcome the elastic repulsion forces preventing the release of the guest composition. Charged substances that could be used to trigger release include, without limitation, a variety of charged amphiphiles/surfactants and/or polymers known in the art. Changing the pH of the surrounding environment also changes the charge distribution in a way that can trigger release. We also found that the introduction of amphiphiles (e.g., surfactants) into the recipient environment can cause convective flows in the host composition that can provide the strong hydrodynamic force for the guest composition to overcome the elastic repulsion force. In the non-limiting examples below, we illustrate this in more detail.

In Example 4, we demonstrate that the addition of an isotropic solute (propanol) into the host composition can facilitate guest composition release, by inducing an N-to-I phase transition.

In Example 5, we demonstrate that the electrostatic attraction force between the guest composition and the surrounding environment with oppositely charged surfactants can be used to trigger release, even in the absence of moving phase boundaries, phase transitions, or elevation of temperature. The electrostatic attraction force was established that acted to counter the elastic repulsion forces that initially prevented release of the guest composition. Addition of oppositely charged surfactants into the guest composition and the surrounding environment activates the release of the guest composition from the host composition, while the addition of same charged surfactants deactivates the release.

In Example 6, we used charged polymers and biological molecules to induce an electrostatic force sufficient to counter the elastic repulsion forces that initially prevented release of the guest composition.

In Example 7, we demonstrate that changing the pH of the surrounding environment can effectively be used change the balance of electrostatic forces, thus triggering release.

In Example 8, we demonstrate that the hydrodynamic forces arising from the amphiphile induced convection flow can be used to trigger release, even in the absence of moving macroscopic phase boundaries, phase transitions, elevation of temperature. We found that strong convective flows in the host composition can be induced when the host composition is in contact with the recipient environment containing amphiphiles. The induced flow can provide hydrodynamic forces sufficient for the guest composition to overcome the elastic repulsion forces and thus activate the release.

3. Presence of Motile Bacteria

The design of materials that release antimicrobial agents represents an important challenge for health applications, food safety, etc. A common approach is to use a material the releases the agent. However, in existing materials designs, the agent is constantly leached, independent of whether or not bacteria are present. In Example 10 below, we demonstrate a material that only releases microcargo in the presence of motile (living) bacterial cells. This preserves the active agent for use only when bacteria are present. It minimizes unwanted release of agents, potentially causing toxicity to other cells types. The LC can also optically report the arrival and killing of the bacteria.

As with other triggers, other advantages of the system are that it does not require complex fabrication processes typical of microelectromechanical systems. The approach can be applied to diverse geometries (e.g., wells, films, and emulsion droplets) and sized (micrometer to millimeter).

D. Combined Triggers

Each of the disclosed triggers or specific examples of each can be combined into a single system or method. For example, two or more different stimuli can be used in the same system, or two or more different chemical stimuli (e.g., specific surfactants, charged polymers, etc.) may be used with the same or different guest and/or host compositions.

E. Optical Response Generated Simultaneously with Release Trigger

There are very few materials known in the art that are capable of providing both optical sensing and controlled release of a sequestered guest composition. In the disclosed compositions and methods, the trigger that facilitates the controlled or on-demand release of the guest compositions sequestered within the host composition may also generate an optical response within the host composition. Non-limiting examples of this phenomenon can be seen in FIGS. 1C-to-1D, 16A-to-16B, 16I-to-16J, 20F-to 20G, and 26K, and are described in more detail in Example 1, Example 5, Example 6 and Example 10.

F. Applications for the Disclosed Systems and Methods

The disclosed methods and systems are advantageously simple, in that they do not require any complex devices or procedures. Instead, the disclosed methods depend on the manipulation of elastic repulsion forces and/or inducing the appropriate counter forces to overcome the elastic repulsion forces using simple triggers, such as the use of charged additives or temperature changes that can be induced in numerous simple ways known in the art. The guest compositions of interest may be safely preserved within the anisotropic fluid host composition without release, until release is desired. The timing and amount of release can be readily controlled by adjusting simple trigger cues (e.g., the number of heating and cooling for phase transitions, the rate of temperature change, target temperature, or concentration of charged additives). Furthermore, the disclosed methods and systems can be readily scaled up or down.

Accordingly, the disclosed systems and methods would have a variety of applications, including, without limitation, in the fields of drug delivery, responsive materials development, packaging, antimicrobial surface development, micro-cargo transportation, microfluidics, and optofluidics.

In non-limiting examples, the disclosed systems and methods may be used to release antimicrobials or local anesthetics on-demand, may be incorporated into bandages that release wound healing or other agents on-demand, or may be used to release biotoxic agents, such as LPS-containing organisms. The disclosed systems and methods may be used to release fragrances, perfumes or deodorants as needed. The disclosed systems and methods may be used to release cleaning fluids as needed, or to release on-demand one or more substances capable of dissolving electric circuits or otherwise destroying or rendering unusable an electric or mechanical device. For example, if a military or proprietary drone incorporating the disclosed system were to crash or become disabled, the disclosed system could be used to release a substance that could destroy the drone before it was found by other parties. Other applications would be readily apparent to the skilled artisan reviewing this disclosure.

The following examples are offered for illustrative purposes only, and are not intended to limit the scope of the disclosed systems and methods in any way. Indeed, various modifications in addition to those shown and described herein will become apparent to those skilled in the art from the foregoing description and the following examples and fall within the scope of the appended claims.

III. Examples

Introduction to the Examples

Over the past few decades, considerable endeavor has been devoted to developing systems for controlled release of single or multiple chemical substances on demand. Such systems have a number of promising potential applications, such as for controlled and/or on-demand drug delivery. Accordingly, a number and variety of controlled release systems have been proposed. Many of these use polymers having particular physical or chemical characteristics such as biodegradability [1-5], or responsiveness to magnetic field [6, 7], electric field [8], light [9, 10], pH [11, 12] or temperature [13]. As the stable and various types of emulsions became available (e.g., lipid-, surfactant-, and biopolymer-based), they have been also widely utilized to contains and deliver the target materials [14-18]. In addition, recent advances in the field of microfabrication have created a new class of controlled-release systems. Their small size potential for integration with micro-electronics (e.g., micrometer-scale chips, pumps, valves and flow channels) could make controlled-release microchips [19-24].

In these examples, we disclose novel and simple systems for the controlled release of desired materials on the basis of anisotropic fluids. Nematic liquid crystals (LCs), a representative example of an anisotropic fluid, are composed of molecules exhibiting the preferred orientation, the so-called director n [25] When the droplets of immiscible (or insoluble) guest material are introduced in the nematic host, n around the droplets is determined by the balance of the elastic cost KR of the bulk deformations and the surface anchoring energy $WR^2$, where K is the Frank elastic constant, W is the anchoring coefficient, and R is the radius of the guest materials [26-28]. For typical thermotropic LCs, $K \sim 10^{-12}$ [29] and $W \sim 10^{-6}$ J/m$^2$ [28], thus K/W~1 µm and the associated elastic energy is ~$2400k_BT$ (See Example 11), where $k_B$ is the Boltzmann constant and T is the temperature. When $WR^2 > KR$ (i.e., R>K/W), the droplets distort surrounding n, thereby generating not only the topological defects but also the repulsive forces (so-called elastic repulsion force $F_E$) against nematic interfaces [30-32]. In the absence of external forces, therefore, the guest materials of R>K/W can be sequestered within the bulk LC, thus preventing their release to contacting, immiscible surrounding environment (gases, liquids or solids), FIGS. 1A and 1B. Contrarily, the guest materials in isotropic fluids (e.g., water emulsions in oil) will be discharged into the surrounding environment because of no repulsive forces between the guest materials and the interfaces of isotropic fluid.

In these examples, we demonstrate that the elastic repulsion that normally prevents release of guest materials from the LC host can be leveraged to design LC-based systems that trigger the release of dispersed materials in response to a range of simple cues, such as (i) thermally- or optically-induced phase transitions between nematic (N) and isotropic (I) phases; (ii) physical or chemical stimuli that influence the elasticity of the LCs; (iii) addition of ionic or non-ionic amphiphiles, charged polymers, or pH changes that lead to changes in electrostatic attraction, convection flow resulting in hydrodynamic force, or both; and (iv) the addition of a solute to the LC host. Furthermore, we derived a model to elucidate the underlying physical mechanisms of transport and release that agrees well with the results of the disclosed experiments. In comparison to other strategies for controlled release, the merits of these LC-based systems and methods include superior simplicity, in that they require no complex instrumentations (e.g. micro-pump or valves) or chemical modifications, diverse geometries (e.g., wells, films, and emulsion droplets) and sizes (micrometer to millimeter), and the adaptability of the LC-based systems, in that they can be applied to a wide range of materials in any phase states. These attributes are important in potential applications in a variety of fields, including drug delivery, micro-cargo transportation, and micro- and opto-fluidics.

Example 1: Controlled Release Activated by Nematic-Isotropic Phase Transitions, which May Also be Accompanied by an Optical Response In this example, we demonstrate a first trigger that can be used to activate the release of guest droplets from nematic LCs: the propagation of N-I interface during the N-I phase transitions under the temperature gradient across the LC layer. In addition, we demonstrate that an optical response may be induced by the release trigger within the LC.

When a LC interface is heated (or cooled) above (or below) the N-I phase transition temperature ($T_{NI}$), a phase transition occurs first at the heated (or cooled) surface and subsequently the resulting N-I interface propagates to the other side of the LC. Due to repulsive forces between the guest materials and the N-I interface, such as elastic repulsion [30-32] and forces arising from the change of elastic

[33] and interfacial energies [34-39], the propagating N-I interface is expected to transport the guest droplets dispersed in LCs. We sought to utilize this transporting ability to release the droplets into immiscible aqueous phases or solid substrates contacting the LC.

In order to experimentally verify this idea, a demonstration system having a simple geometry was prepared, as depicted in FIG. 1B. We dispersed aqueous microdroplets (0.5≤R≤3 µm) containing a water-soluble red dye (tracer) and the surfactant sodium dodecyl sulfate (SDS) in nematic 4'-pentyl-4-biphenylcarbonitrile (5CB), and then filled a mini-well (3.5 mm in depth) with the dispersion (FIG. 1B). Subsequently, the mini-well was submerged into a water bath (see Example 11 for sample preparation).

The SDS adsorbed at the aqueous-LC interface of the droplets and aligned n perpendicular to the droplet interface (a so-called homeotropic alignment) [40]. Accordingly, each aqueous microdroplet was surrounded by a region of strained LC that included a point topological defect, so-called a hyperbolic hedgehog [26, 30, 41], FIG. 1A. The LC adopted a parallel orientation at the interface to an overlying aqueous phase, leading to a bright optical appearance of the system (see inset in FIG. 1C). Consistent with the effects of elastic repulsion of the guest microdroplets away from the macroscopic LC to the bulk aqueous phase, at T=25° C. (before phase transitions) the aqueous environment contacting the LC remained free of red tracer even for four days (FIGS. 1C and 1G). The sequestration of microdroplets in a nematic LC was observed to occur independent of the relative density of the microdroplets ($\rho_{aq}$) and LC ($\rho_{LC}$) because $F_E$ is much larger than buoyant forces ($F_B$) at room temperature; for R=3 µm and 5CB, $F_E/F_B$>8000 (See Example 11).

We found that heating of 5CB to $T_H$>35° C. from below (via contact with a warm body) led to an optically observable N-to-I phase transition (insets in FIGS. 1C and 1D) and also triggered release of red tracer into the overlying aqueous environment (FIG. 1D).

The optically observable phase transition is an example of another aspect of the disclosed compositions and methods. Specifically, the release trigger can be "sensed" by the LC host composition in an optically observable manner. Thus, an optical signal may be used to signal the contemporaneous release of the sequestered guest composition from the LC host composition.

FIGS. 1C-1F shows the photographs of mini-wells in "SIDE VIEW" as a function of phase transitions. Insets in FIGS. 1C and 1D are micrographs (TOP VIEW) of the mini-wells between crossed polarizer.

Since nematic liquid crystal has a birefringence (i.e., retardance is not 0), it shows a bright texture between crossed-polarizer (Inset in FIG. 1C). After nematic-to-isotropic phase transition, however, the bright texture becomes dark (Inset in FIG. 1D) because isotropic phase does not have a birefringence (i.e., retardance is 0).

This data demonstrates that, in response to N-I phase transitions, our system can exhibit not only the release of microdroplets from liquid crystals, but also optical responses that are contemporaneous with the release.

The release occurred independent of the relative magnitudes of $\rho_{aq}$ and $\rho_{LC}$, including for conditions under which the microdroplets sediment downward and away from the interface to the overlying aqueous environment ($\rho_{aq}$>$\rho_{LC}$). Surprisingly, however, the release was transient, coinciding with the period of time during which the phase transition took place (FIG. 1H).

Figures 3A, 3B, 3C, 3D, 3E, 3F, 3G:
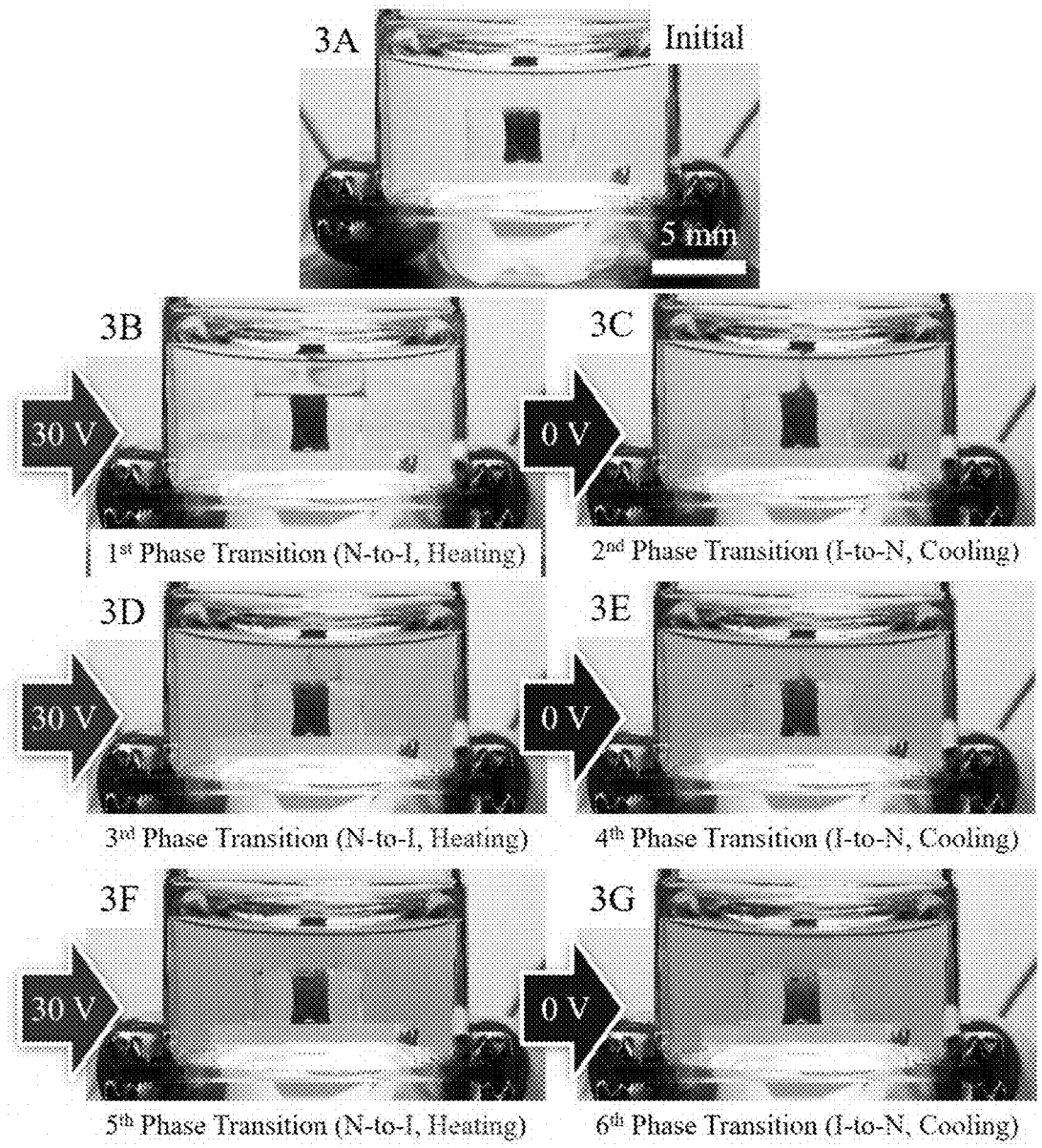
FIGS. 3A, 3B, 3C, 3D, 3E, 3F and 3G illustrate the thermally-triggered release of microdroplets with resistive heating (Joule heating).

A second pulse of tracer was released when the system was cooled back to $T_C$=25° C. to reform the birefringent N phase (FIG. 1E). We subsequently repeated cycles of heating and cooling and observed that, along with each optical response, a well-defined pulse of red tracer was ejected into the overlying aqueous phase (FIG. 1I). After 20 cycles, the amount of tracer dispensed into the aqueous environment was linearly proportional to the concentration of aqueous droplets $C_{aq}$ initially in the LC (FIGS. 1F and 1J) and corresponds to around 40% of aqueous droplets initially dispersed in 5CB. Thermal release was also conveniently initiated by Ohmic heating of a thin electrically resistive film supporting the LC (FIG. 3).

Figures 4A, 4B, 4C:
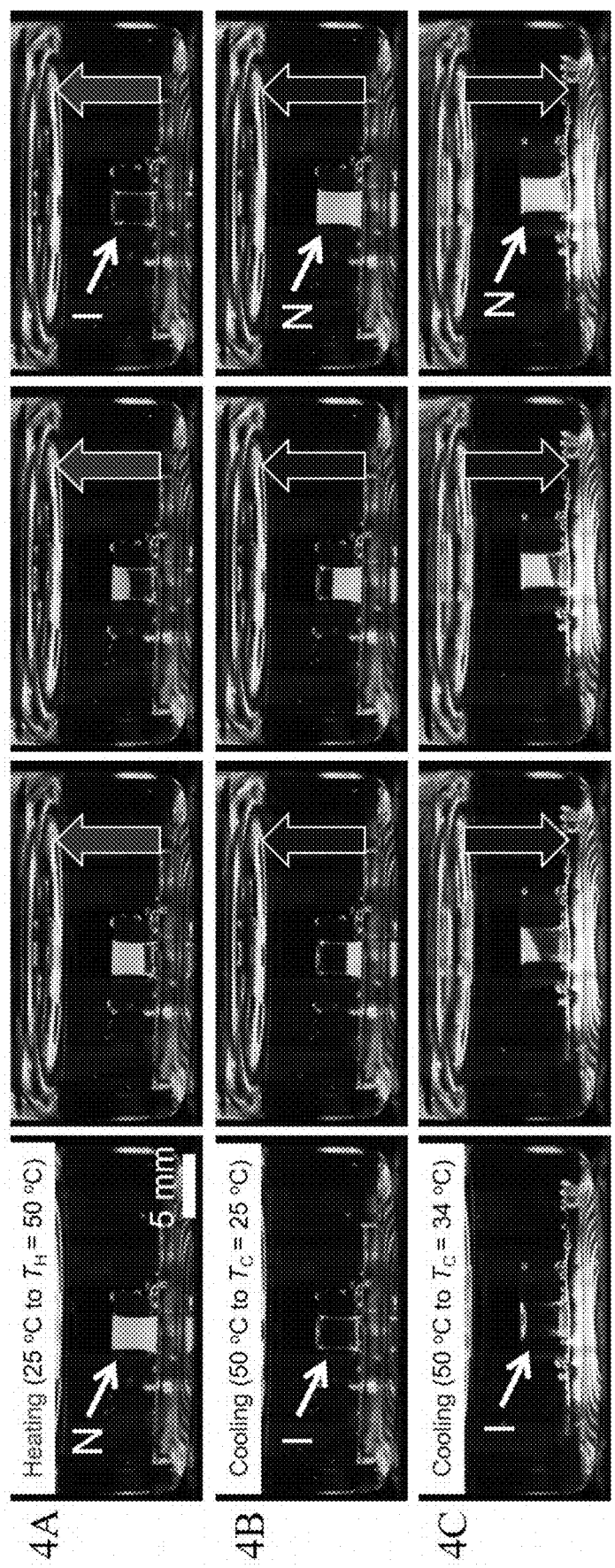
FIGS. 4A, 4B and 4C show the dependence of the propagation direction of the N-I interface on the heating $T_H$ and cooling temperatures $T_C$.
Figures 5A, 5B:
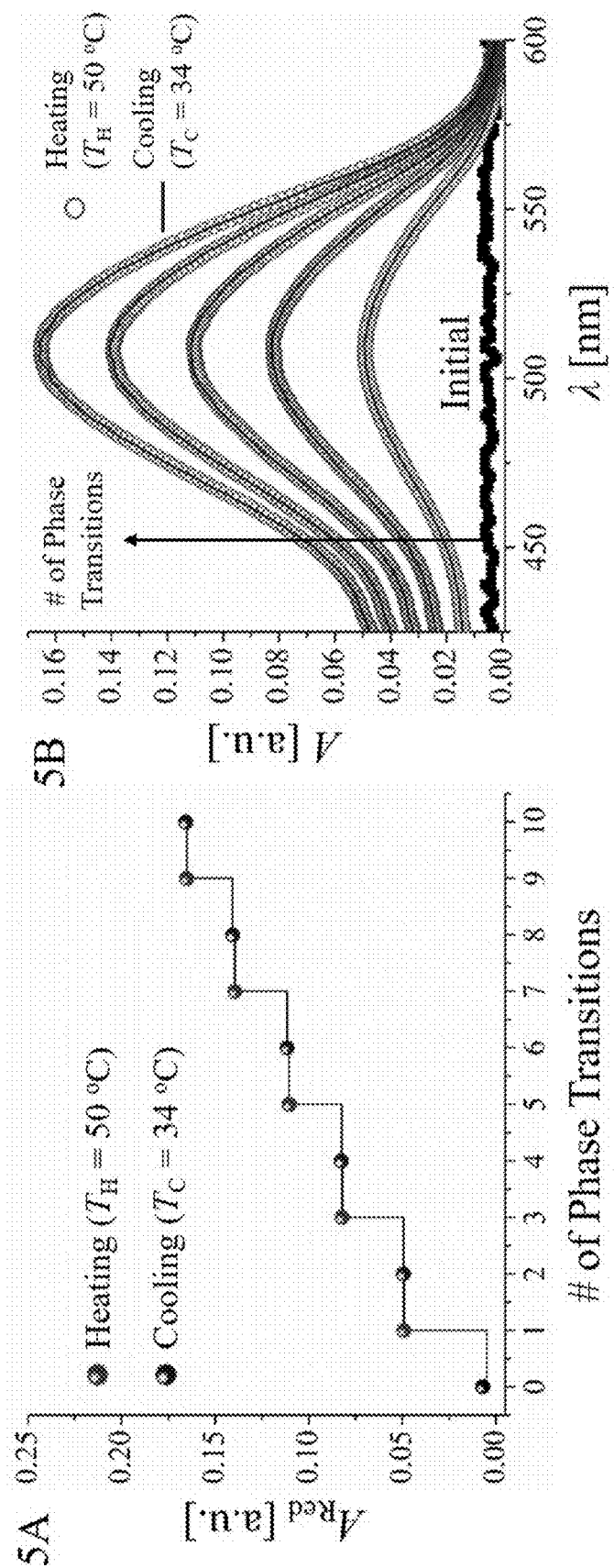
FIGS. 5A and 5B show the deactivation of the release of microdroplets upon cooling with $T_C$=35° C.

We determined subsequently that the pulsatile release of the microdroplets and red tracer accompanied the upward motion of the N-I interface toward the overlying aqueous environment (FIG. 4). Upon heating from T=25° C. to $T_H$>$T_{NI}^{5CB}$ (N-to-I phase transition), the N-I interface moved upward (toward LC-aqueous interface, FIG. 4A) regardless of $T_H$ and microdroplets were ejected (FIGS. 1D and 1H). Upon cooling from T=50° C. to $T_C$=25° C. (I-to-N phase transition), it also showed the upward-directed motion of the interface (FIG. 4B) and ejection of microdroplets (FIGS. 1E and 1I). Upon cooling from T=50° C. to $T_C$=34° C. (I-to-N phase transition), however, it showed the downward-directed motion of the N-I interface (FIG. 4C) and the absence of release of tracers (FIG. 5). The critical dependence of the release on the propagation direction of N-I interface supports the idea that the droplets are transported by the N-I interface.

To provide insights into the role of the motion of N-I interface in the transport of microdroplets, the droplets were observed microscopically during the passage of N-I interfaces. In this experiment, we deliberately used droplets with a wide range of radii (0.5≤R≤30 µm). Microscopic observations revealed that elastic interactions between the aqueous microdroplets and the moving N-I interface pushed the microdroplets ahead of the interface in a manner that was dependent on the size of the microdroplets.

For example, upon heating (N-to-I phase transition), a N-I interface ($v_{NI}$) moving at 10 µm/s pushed microdroplets with R<10 µm ahead of the N-I interface into the aqueous environment whereas larger microdroplets (R>10 m) were left behind the moving N-I interface (FIGS. 6A-6H and 7A-7D).

Upon cooling (I-to-N phase transition), similar behavior was observed. However, the microdroplets with R<10 µm could be transported even at the faster motion of N-I interface, $v_{NI}$=35 µm/s (FIGS. 7E-7H). Upon both heating and cooling, the fraction of microdroplets released into the environment from the LC was controlled by $v_{NI}$, as the velocity set the radius of the largest microdroplets (or clusters) to be pushed ahead of the N-I interface (R*) by elastic forces; R* decreased with increase in $v_{NI}$. Under the sufficiently high velocity ($v_{NI}$=100 µm/s), the interface could not transport any droplets upon both heating and cooling (FIGS. 7M-7R).

Beside R* dependence on $v_{NI}$, we make two key observations regarding the observations above. First, we observed single droplets or droplet clusters with R<R* to be transported initially by the N-I interface (denoted by dotted circles in FIGS. 7C, 7D, 7G, and 7H). As the moving interface formed bigger clusters with R>R* by collecting additional droplets, however, we observed some droplets from the cluster to be left behind the interface as illustrated in FIGS. 7I-7L. West et al. [34, 39] observed similar behaviors with solid particles and attributed it to an increase in effective radius of the particles due to aggregation. Importantly, this observation provides insight into why only a fraction of the microdroplets was released at each phase transition (FIG. 1I). Second, we observed droplets to occasionally coalesce, especially upon heating (denoted by white arrows in FIGS. 7C and 7D). Consequently, large droplets formed through this mechanism, and these large droplets were observed to remain behind the moving N-I interface. This latter observation provides insight into why the amount of tracer released after 20 cycles corresponded to approximately 40% of tracer loaded initially into the 5CB (FIG. 1I). Overall these results indicate that the fraction of guest droplets released can be manipulated by tuning the clustering size and coalescence of droplets.

Additionally, in order to microscopically verify the release process of droplets into a overlying aqueous phase, we explored the transport of microdroplets ahead of moving N-I interface dispersed in a thin LC layer submerged in a water bath.

Figures 8A, 8B, 8C, 8D, 8E, 8F, 8G, 8H, 8I, 8J, 8K, 8L, 8M, 8N:
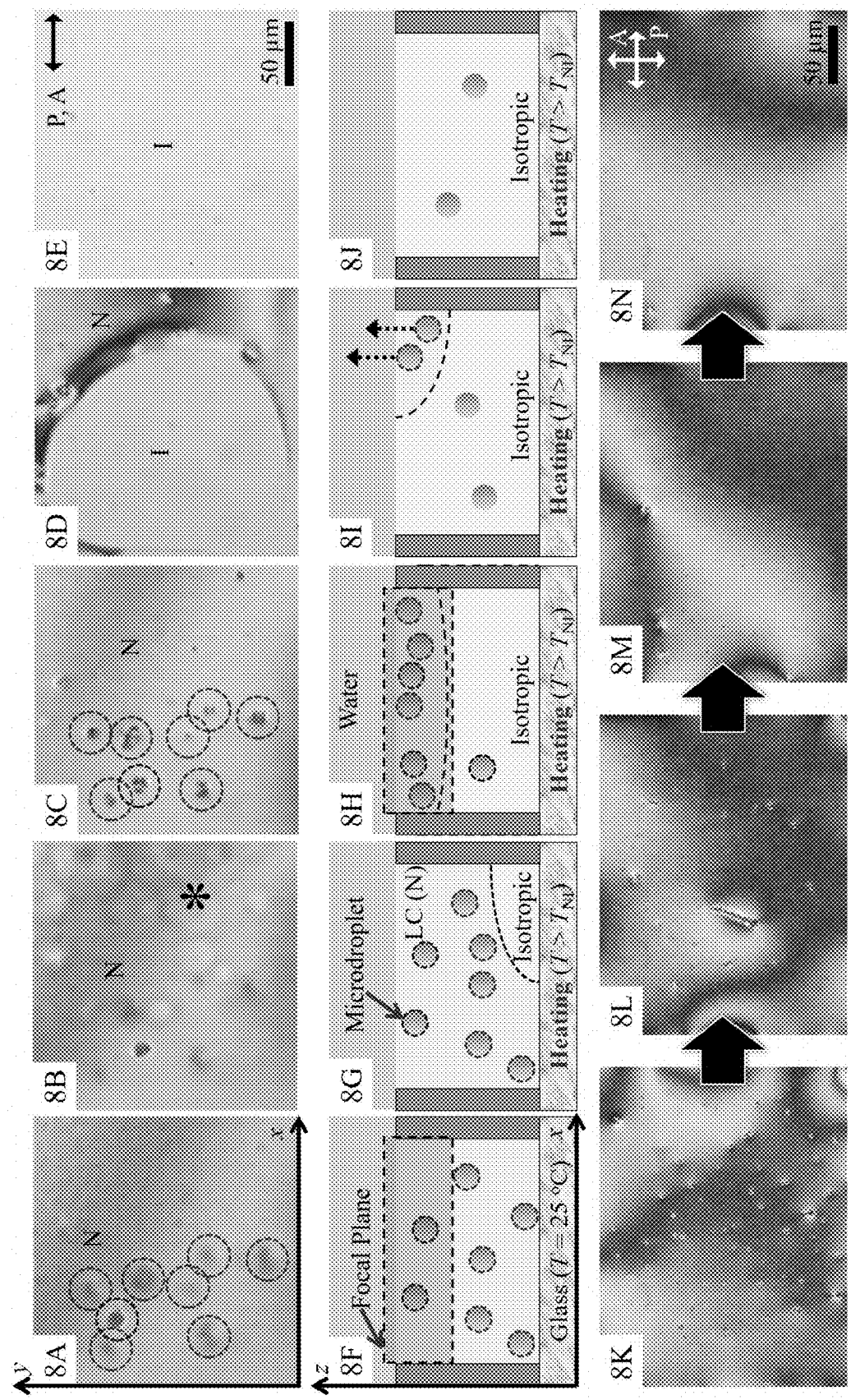
FIGS. 8A, 8B, 8C, 8D, 8E, 8F, 8G, 8H, 8I and 8J are sequential micrographs (top view, 8A-8E) and corresponding illustrations (side view, 8F-8J) of microdroplets transported by a moving N-I interface upon heating ($T_H$=50° C.) in a micro-well. The focal plane was near the LC-water interface (red boxes in 8F and 8H).
FIGS. 8K, 8L, 8M and 8N are micrographs showing the decrease in the population of microdroplets in a LC at T=25° C. (8K) before phase transitions and after 2 (8L), 4 (8M), and 6 phase transitions (8N). P and A indicate the orientations of the polarizer and analyzer, respectively. $T_H$=50° C., $T_C$=25° C., $C_{aq}$=2.5 v %, $C_{SDS}$=9 mM and $v_{NI}$=8 μm/s.

FIGS. 8A-8E and 8F-8J show, respectively, the sequential micrographs (top view) and corresponding illustrations (side view) of microdroplets transported by a moving N-I interface toward LC-water interface upon heating in a microwell. Before phase transitions (FIGS. 8A and 8F), the droplets were trapped in the bulk LC without release. When the glass substrate was heated to $T_H=50°$ C., the N-to-I phase transition (denoted by * in FIG. 8B) first occurred at the LC-glass interfaces, and the N-I interface started to propagate toward the LC-water interface with $v_{NI}=8$ µm/s (FIGS. 8B and 8G). As the interface propagated upward, the droplets that were previously out of focus (red dotted circles in FIG. 8A) moved into focus, implying that the droplets were delivered near the LC-water interface (FIGS. 8C and 8H). As the interface reached the LC-water interface, the droplets disappeared as they were released into the overlying aqueous phase (FIGS. 8D and 8I). In this condition ($v_{NI}=8$ µm/s), we observed that the interface transported the droplets or (clusters) with R<12 µm. After the phase transition, we observed some droplets remained in a LC (FIGS. 8E and 8J). However, their population could be reduced by repeating the phase transitions (FIGS. 8K-8N), consistent with the pulsatile release of microdroplets (FIG. 1I).

Figures 9A, 9B, 9C, 9D:
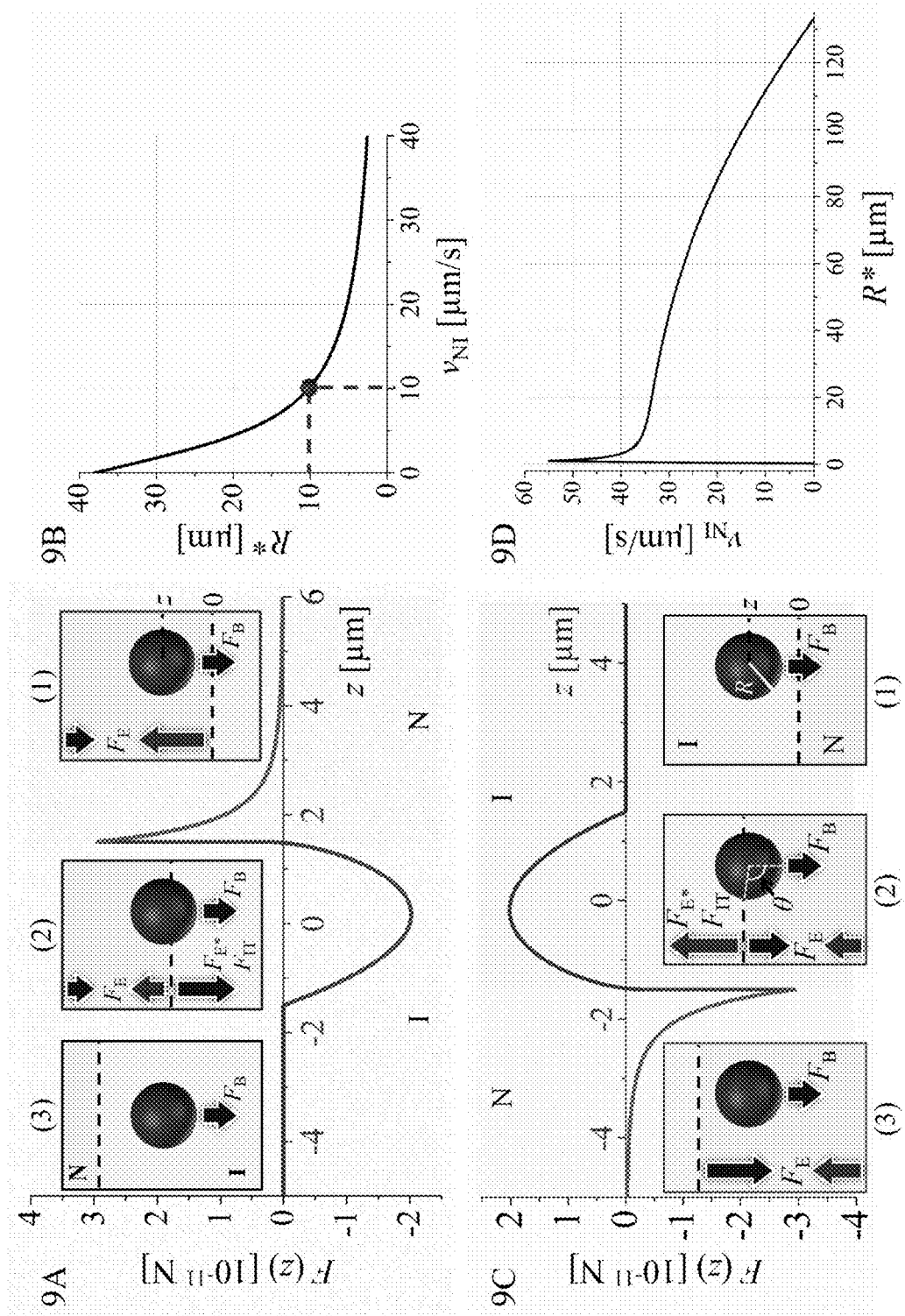
FIGS. 9A, 9B, 9C and 9D show the net force F(z) (9A and 9C) acting on a microdroplet (R=1.5 μm) in 5CB and calculated dependence of R* (9B and 9D) on $v_{NI}$ upon N-to-I (9A and 9B) and I-to-N phase transitions (9C and 9D). Insets in FIGS. 9A and 9C show illustrations of the forces at z≥R (in N for 9A and in I for 9C), −R<z<R (at N-I interface), and z≤−R (in I for 9A and in N for 9C). Red and blue arrows indicate the forces that favor and inhibit the ejection of microdroplets, respectively. Red point in FIG. 9B indicates R* at $v_{NI}$=10 μm/s, which coincides with experimental values.
Figures 10A, 10B, 10C, 10D, 10E, 10F, 10G:
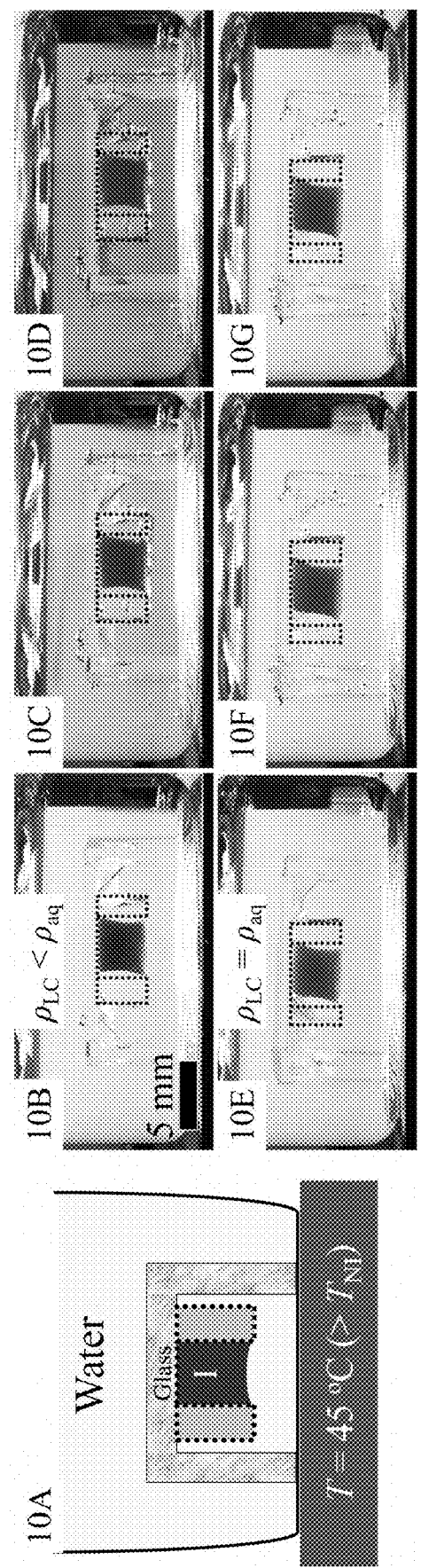
FIGS. 10A, 10B, 10C, 10D, 10E, 10F, and 10G show the role of buoyant forces in the release of microdroplets.

To provide insight into the above observations, we evaluated the net force F(z) acting on a quasi-static microdroplet as a function of the vertical position of the center of the microdroplet (z) relative to a N-I interface (z=0), FIG. 9A(1). F(z) includes contributions from the repulsive elastic interaction of the microdroplet with the LC interface ($F_E$ [30-32]), buoyant forces ($F_B$), and forces arising from interfacial and elastic energies that change when the microdroplet penetrates the N-I interface ($F_{IT}$ [34-39] and $F_{E*}$ [34, 39, 42, 43], respectively).

Therefore, net force $F^H(z)$ upon heating can be expressed as:

at $z \geq R$ (in the N phase, FIG. 9A(1))

$$F_N^H(z) = \left\{ A^2 \pi K \frac{3}{4} \left( \frac{R^4}{z^4} - \frac{R^4}{(L-z)^4} \right) \right\}_{F_E} - \left\{ \frac{4}{3} \pi R^3 g (\rho_{aq} - \rho_{LC}) \right\}_{F_B}, \quad (1)$$

at $-R < z < R$ (at the N-I interface, FIG. 9A(2))

$$F_{NI}^H(z) = \quad (2)$$
$$\left\{ A^2 \pi K \frac{3}{4} \left( 1 - \frac{1}{\left(L - \frac{z+R}{2}\right)^4} \left( \frac{z+R}{2} \right)^4 \right) \right\}_{F_E} - \left\{ \frac{4}{3} \pi R^3 g (\rho_{aq} - \rho_{LC}) \right\}_{F_B} - $$
$$\left\{ 2\pi R \sigma_{NI} \left(1 - \frac{z^2}{R^2}\right) \right\}_{F_{IT}} - \left\{ \left(1 + \frac{z}{R}\right) \left( \alpha \left[ WR + \frac{(WR)^2}{K} \right] + \beta K \right) \right\}_{F_{E*}},$$

and at $z \leq -R$ (in the I phase, FIG. 9A(3))

$$F_I^H(z) = -\left\{ \frac{4}{3} \pi R^3 g (\rho_{aq} - \rho_{LC}) \right\}_{F_B}, \quad (3)$$

where A, α, and β are numerical factors (A=0 for R<K/W or z≤-R [31, 32], α=0 for R>K/W and β=0 for R<K/W), L is the thickness of the nematic layer, g is the gravitational acceleration, and $\sigma_{NI}$ is the interfacial tension of the N-I interface. FIG. 9A shows $F^H(z)$ for a static droplet with R=1.5 µm in 5CB (see Example 11 for parameters used in the calculation). When a droplet (R>K/W, homeotropic anchoring) is in the N phase (z≥R), the net force $F_N^H(z)$ arises from $F_B$ and $F_E$ with A 2.04 [31, 32], FIG. 9A(1). As the N-I interface approaches the microdroplet positioned at z≥R (i.e., in the nematic phase, FIG. 9A(1)), $F_N^H(z)$ increases with decrease in z and becomes positive (upward-directed) at z<z* due to repulsive elastic repulsion from the approaching N-I interface (first term of $F_E$ in Eq. (1)); $F_N^H(z^*)=0$ and z*=17.0 µm for a droplet with R 1.5 µm in 5CB. This model predicts that a stationary N-I interface will elastically levitate a microdroplet at a height defined by F(z)=0 at z=z* above the N-I interface. $F_N^H(z)$ shows a maximum at z=R (red curve in FIG. 9A).

If the N-I interface contacts the microdroplet (-R<z<R, FIG. 9A(2)), two additional forces are generated from the interfacial tensions ($F_{IT}$)[34, 38] and elastic strain ($F_{E*}$)[34, 43]. These forces drive the droplets into the I phase (FIG. 9A(2)). See Example 11 for additional detail. Additionally, $F_E$ needs to be modified because the part of the droplet that protrudes into the I phase no longer strains the LC. R in Eq. (1) is the radius of the part of droplet in the N phase and we used (R+z)/2 as the radius for simplicity. One also needs to take into account the decrease in the topological strength m of the droplet [26] from 1 to θ/π where θ (0≤θ≤π) is half of the central angle of the part of droplet in a N phase, FIG. 9C(2). Since the elastic interaction is proportional to $m^2$ [25, 26], therefore, a numerical factor A at -R<z<R can be described as A=2.04·m=(2.04/π) cos$^{-1}$(-z/R). Consequently, both interfacial ($F_{IT}$) and additional elastic forces ($F_{E*}$) cause F(z) to change sign, resulting in a net downward-directed force and expulsion of the microdroplet into the I phase (blue curve in FIG. 9A).

In the I phase (z≤-R, FIG. 9A(3)), the net force $F_I^H(z)$ is comprised only of $F_B$; A=0 and thus $F_E$=0. Therefore, the microdroplet in 5CB ($\rho_{5CB}<\rho_{aq}$) sink while the droplets in E7 ($\rho_{E7}>\rho_{aq}$) rise.

Upon heating, elastic repulsion from the N-I interface promotes release of the microdroplets (first terms of $F_E$ in Eq. (1)). Therefore, the moving N-I interface can only transport droplets with R>K/W in a nematic phase ($F_E\neq 0$). The interface passes through the droplets with R<K/W due to $F_E$=0.

In our experiments, however, the N-I interface is moving, and thus a microdroplet pushed by elastic forces ahead of the moving N-I interface will also experience a downward-directed Stokes drag force, $F_S=-6\pi \eta_{LC} v_{aq} R$ where $\eta_{LC}$ is the dynamic viscosity of the LC [44]. If $F_S$ exceeds the maximum value of F(z) (FIG. 9A), the microdroplet will break through the moving N-I interface. When $(z-R)/R \ll 1$, $F_E$ is independent of R, whereas the drag force scales linearly with R. Accordingly, for each value of $v_{NI}$, our model defines a critical microdroplet radius R* above which microdroplets are not transported by a moving N-I interface (FIG. 9B).

Our model predicts R*=10.2 μm for $v_{NI}$=10 μm/s (FIG. 9B), in good agreement with our experiments (FIGS. 6 and 7; 10±1 μm). Our model also predicts that a microdroplet with R=1.5 μm pushed by a N-I interface with $v_{NI}$=10 μm/s will be able to reach within 60 nm of the interface of an overlying aqueous phase. At this separation, attractive interfacial forces such as van der Waals and electrical double layer forces (see below) mediate fusion of the microdroplets with the overlying aqueous phase (FIG. 8).

A modified version of the above-described model also explains the ejection of microdroplets by an upward-directed motion of the I-N interface during cooling. Upon cooling, net force $F^C(z)$ acting on a quasi-static droplet can be written as:

at $z \geq R$ (in the I phase, FIG. 9C(1))

$$F_I^C(z) = -\{4/3 \pi R^3 g(\rho_{aq} - \rho_{LC})\}_{F_B},\tag{4}$$

at $-R \leq z \leq R$ (at the N-I interface, FIG. 9C(2))

$$F_{NI}^C(z) = -\left\{A^2 \pi K \frac{3}{4}\left(1 - \frac{1}{\left(L - \frac{(R-z)}{2}\right)^4}\left(\frac{(R-z)}{2}\right)^4\right)\right\}_{F_E} -$$
$$\left\{\frac{4}{3}\pi R^3 g(\rho_{aq} - \rho_{LC})\right\}_{F_B} + \left\{2\pi R \sigma_{NI}\left(1 - \frac{z^2}{R^2}\right)\right\}_{F_{IT}} +$$
$$\left\{\left(1 - \frac{z}{R}\right)\left(\alpha\left[WR + \frac{(WR)^2}{K}\right] + \beta K\right)\right\}_{F_{E^*}},\tag{5}$$

and at $z \leq -R$ (in the N phase, FIG. 9C(3))

$$F_N^C(z) = -\left\{A^2 \pi K \frac{3}{4}\left(\frac{R^4}{z^4} - \frac{R^4}{(L+z)^4}\right)\right\}_{F_E} - \left\{\frac{4}{3}\pi R^3 g(\rho_{aq} - \rho_{LC})\right\}_{F_B},\tag{6}$$

where A $(2.04/\pi) \cos^{-1}(z/R)$ in Eq. (5) and A 2.04 in Eq. (6) for R>K/W but A=0 for R<K/W. In the I phase ($z \geq R$, FIG. 9C(1)), aqueous droplets in 5CB sink due to $\rho_{5CB} < \rho_{aq}$ (i.e., $F_1^C(z)$ 0). In contrast to heating, the two additional forces $F_{IT}$ and $F_{E^*}$ at $-R < z < R$ are upward-directed upon cooling, FIG. 9C(2); $F_{IT} > 0$ and $F_{E^*} > 0$. As a result, $F_{NI}^C(z)$ becomes positive and exhibits a maximum at $-R < z < R$, FIG. 9C. Importantly, upon cooling $F_{IT} > 0$ and $F_{E^*} > 0$, regardless of R. This indicates that the cooling N-I interface can transport the droplets with both R>K/W and R<K/W (FIG. 9D), whereas the interface upon heating cannot transport the droplets with R<K/W (i.e., R*($v_{NI}$)=0 for R<K/W, FIG. 9B).

At $z \leq -R$ (in a N phase, FIG. 9C(3)), the droplets with R>K/W are sequestered in a nematic bulk while the droplets with R<K/W sediment away from the N-I interface.

In FIG. 1, $v_{NI}$ upon both cooling and heating was 37±3 μm/s, at which our model predicts the dispensing of droplets with K/W (~1 m)≤R≤3 μm upon heating and 0.6 μm≤R≤6 μm upon cooling. This prediction is consistent with our observation that the amount of tracer released upon cooling was greater than upon heating (FIG. 1I).

The balance of force acting on a microdroplet in a LC (Eq. 3) indicate that after a N-to-I phase transition, the release of microdroplets can be manipulated by the buoyant force due to the absence of elastic barrier. FIGS. 10A-G shows the release of microdroplets from an isotropic phase of 5CB depending the relative density of microdroplets and LC. Inverted mini-wells were filled with 5CB containing microdroplets ($C_{aq}$=10 v %) with $\rho_{5CB} < \rho_{aq}$ (FIGS. 10B-10D) and $\rho_{5CB} = \rho_{aq}$ (FIGS. 10E-10G) and then submerged into water baths. When the baths was heated to T=45° C. (>$T_{NI}$) resulting in a N-to-I phase transition, the microdroplets with $\rho_{aq} > \rho_{5CB}$ were continuously released due to the negative buoyant force and the absence of elastic repulsion force in an isotropic phase of 5CB. However, no measurable release of the microdroplets with $\rho_{5CB} = \rho_{aq}$ were observed because F(z)=0. In the system, the motion of N-I interface did not drive the release of microdroplets because the interface propagated toward the closed end (LC-glass interface) during a phase transition.

In sum, this example demonstrates that induced phase transitions between nematic and isotropic phases can facilitate the controlled release of an immiscible or insoluble guest material that is sequestered within the nematic phase. As illustrated in the next four examples, there are other strategies that can be used to facilitate the controlled release of an immiscible or insoluble guest material that is sequestered within an nematic phase, each strategy based on the principle that release can occur if the forces favoring release are great enough to overcome the elastic repulsion forces from nematic interfaces that sequester the guest material within the nematic host.

Example 2: Controlled Release Activated by Elevated Temperature in a Nematic Phase In this example, we demonstrate a second trigger for release of an immiscible or insoluble guest material from an anisotropic phase: the elevation of temperature of nematic host without a phase transition.

LCs can be selected such that their elastic properties can be tuned continuously by using light [45, 46], temperature [46-48] and chemical additives [40, 49], all of which can lead to optical responses and, as we show here, can release dispersed microphases with dynamics that contrast to those observed in the presence of a N-I phase transition (FIG. 1H). For example, the elevation of T leads to the decrease in K that is linearly correlated with the elastic repulsion force, Eq. 1. Therefore, above a certain T, the buoyant forces can overcome the elastic repulsion forces, thereby releasing the guest droplets from nematic LCs.

To illustrate this point, we used a nematic LC called E7; $\rho_{E7} > \rho_{aq}$ and $T_{NI}^{E7}$=60° C. At 25° C., aqueous microdroplets (0.5≤R≤4 μm) were elastically sequestered in E7 because $F_E/F_B$=1194 (See Example 11). As shown in FIGS. 11A-11D, thermal tuning of the elastic properties (at T<$T_{NI}$) led to continuous release of aqueous microdroplets sequestered in the LC into the overlying aqueous phase. In contrast, when exposed to the same thermal stimulus, 5CB provided pulsatile release of microdroplets (FIGS. 1H and 1I).

Figures 11A, 11B, 11C, 11D, 11E, 11F, 11G:
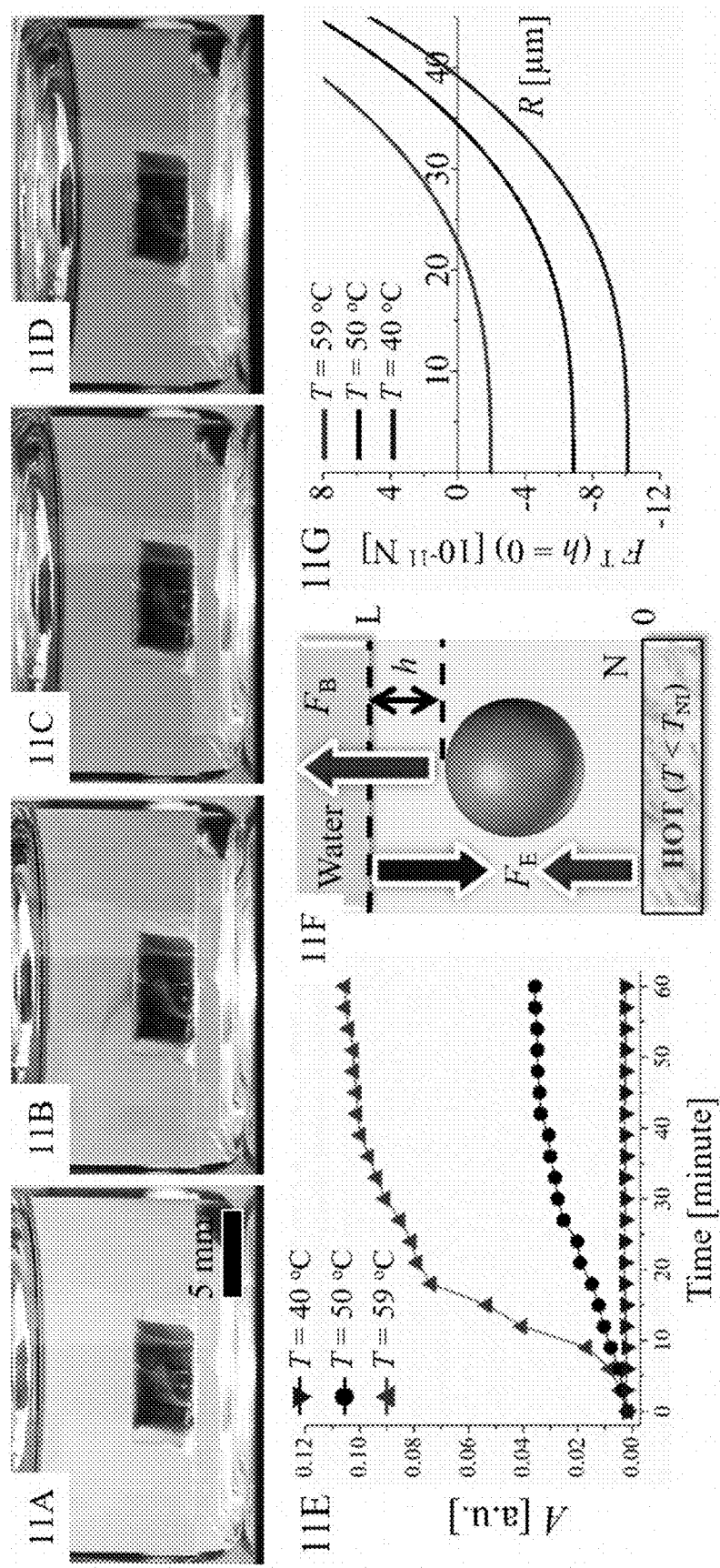
FIGS. 11A, 11B, 11C, 11D, 11E, 11F and 11G show the continuous release of microdroplets from a nematic LC E7 in response to an elevated temperature that is below $T_{NI}$.

The amount of release was quantitatively analyzed by measuring A as a function of time and T (<$T_{NI}$). As shown in FIG. 11E, A increases with time and T while there was no noticeable release at T≤40° C. In this system, the total force $F^T$ is comprised of $F_B$ and $F_E$ and can be expressed by $$F^T(z) =\tag{7}$$

Figures 12A, 12B, 12C, 12D, 12E, 12F, 12G, 12H, 12I:
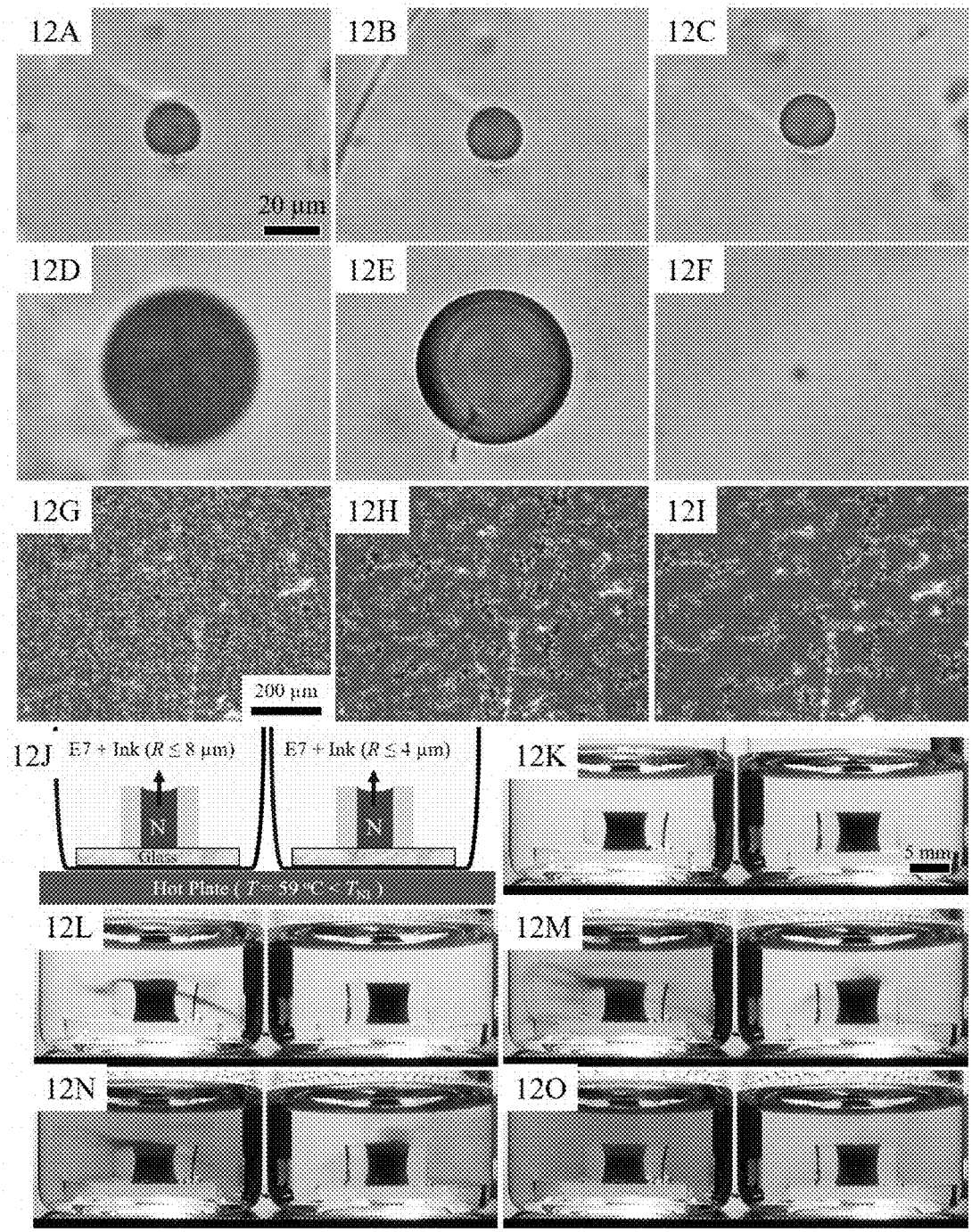

-continued $$\left\{\frac{4}{3}\pi R^3 g(\rho_{LC} - \rho_{aq})\right\}_{F_B} + \left\{A^2\pi K\frac{3}{4}\left(-\frac{R^4}{(h+R)^4} + \frac{R^4}{(L-(h+R))^4}\right)\right\}_{F_E},$$

where A=2.04 and h is the distance between the droplets and the LC-water interface (FIG. 11F). In the system, the upward-directed forces are $F_B$>0 ($\rho_{E7}$>$\rho_{aq}$) and the elastic repulsion from the LC-glass interface (second term in $F_E$). FIG. 11G represents $F^T$ as a function of R at different temperatures at h=0 (See Example 11 for used parameters). Experiment and modeling reveal that release from E7 occurred when |$F_E$| decreased below |$F_B$| (FIG. 11F), which in turn depended on R, h and T. With E7 at T=59° C., we calculated this constraint to be satisfied for R>22 μm (FIG. 11G). Consistent with this prediction, we observed individual LC droplets with R<10 μm to not be released (FIGS. 12A-12C). Large droplets with R>22 μm, or clusters of LC droplets formed through LC-mediated elastic interactions [30-32, 41, 50] with an effective radius R>22 μm, were released (FIGS. 12D-12F). Since 0.5≤R≤4 μm for the aqueous droplets dispersed in E7, for the ejection of microdroplets, it is required to form droplet clusters that are driven by elastic interactions between droplets (FIGS. 12G-12I) and creaming of droplets in our system. When the radius of droplet cluster is bigger than the critical radius above which $F^T$>0, some of droplets from the cluster penetrate the LC-water interface and be released into the overlying water. Because the elastic barrier is enhanced as T is lowered, the droplets are required to make bigger clusters (FIG. 11G). At lower T, therefore, the release would be more suppressed. This predicted behavior is clearly observed in our experiment (FIG. 11E).

The dependence of release on the radius of droplet (or cluster) predicted by our theoretical model (FIG. 11G) was also verified in the following experiment. The mini-wells were filled with E7 containing different size ranges of microdroplets (R≤8 μm for Well-1 and R≤4 μm for Well-2) and subsequently submerged into a water bath (FIG. 12J). At $T_H$=59° C.(<$T_{NI}$), we observed a continuous release of microdroplets from both wells as the positive buoyant force ($\rho_{E7}$>$\rho_{aq}$) overrides the elastic barriers (FIGS. 12J-12O). As shown in FIG. 12O, the mini-well containing the bigger droplets (left bath) exhibited more release due to the facile formation of droplet clusters with R>R* above which a net force becomes positive, consistent with the theoretical model in FIG. 11G.

In sum, this example demonstrates that controlled changes in the elastic repulsion forces at an anisotropic phase interface can be used in combination with other extant forces acting at the interface (in this case, buoyant forces) to facilitate controlled release of an immiscible or insoluble guest material that is sequestered within an anisotropic phase.

Example 3: Controlled Release Activated by a Shear Stress at LC Interfaces

In this example, we demonstrate a third trigger for release of an immiscible or insoluble guest material from an anisotropic phase: shear stresses at LC interfaces.

In addition to thermal triggers, we hypothesized that isothermal triggers (e.g., mechanical shear at LC interfaces) can lower the elastic barrier sequestering guest droplets or provide counterforces to microdroplets that are capable of overcoming elastic repulsions and thus trigger the release of microdroplets from a LC to surrounding environment.

To verify this concept, mini-wells filled with 5CB containing aqueous droplets ($C_{aq}$=20 v %, $C_{SDS}$=9 mM) were immersed into an aqueous bath. Subsequently, we generated a shear flow in the bath by stirring magnetic bar (700-800 rpm) and observed ejections of microdroplets from the mini-well.

In the absence of shear flow, no ejection of microdroplet was observed (FIG. 1G). When the shear flow was introduced in surrounding environments, however, microdroplets were continuously released from a nematic LC as evidenced by the increases in red color density in the bath (FIGS. 13A-13D).

Example 4: Controlled Release Activated by the Addition of Isotropic Solute

In this example, we demonstrate a fourth trigger for release of an immiscible or insoluble guest material from an anisotropic phase: the addition of the isotropic solute into the surrounding aqueous phase.

Figures 14A, 14B, 14C, 14D, 14E, 14F, 14G, 14H:
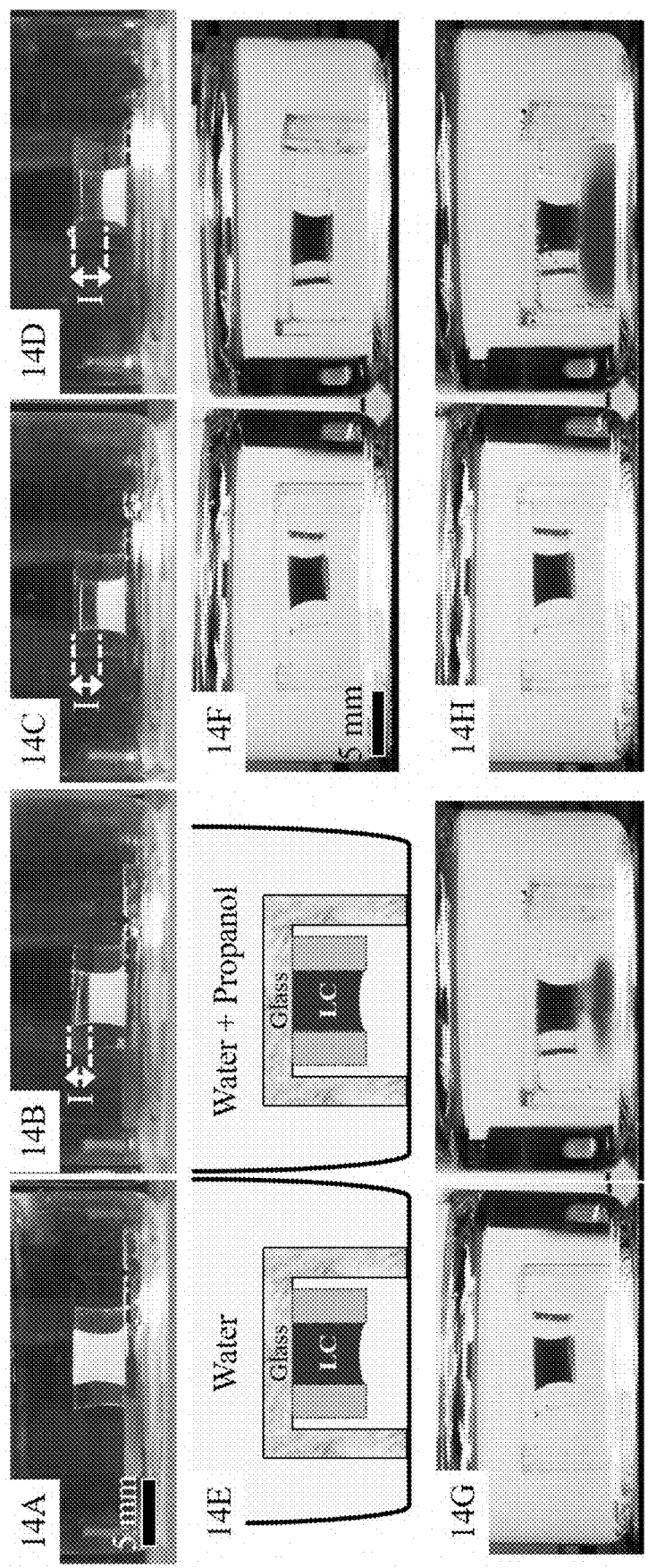
FIGS. 14A, 14B, 14C, 14D, 14E, 14F, 14G, and 14H demonstrate the isothermal release of microdroplets from a LC by a solute triggered N-to-I phase transition.

It has been demonstrated that the absorption of isotropic solute into a nematic LC can lower the N-I phase transition temperature [51]. For example, 5CB filled in a mini-well submerged in a water bath exhibits a nematic phase at 25° C. (FIG. 14A); $T_{NI}^{5CB}$=35° C. When the propanol (isotropic solute) was introduced into the bath ($C_{Propanol}$=16 v %), however, we observed the N-to-I transition occurred first at the LC-water interface and propagated into the LC bulk as the solute diffused into 5CB. As shown in FIGS. 14B-14D, transparent regions (isotropic phase of 5CB) expand with time. We utilized the solute induced N-to-I phase transition to remove the elastic barriers and thus trigger the release of microdroplets from a LC.

For the experiments, the inverted mini-wells were filled with 5CB containing aqueous droplets ($C_{aq}$=10 v %, $C_{SDS}$=9 mM) and then submerged into a water bath and a propanol-water bath ($C_{Propanol}$=16 v %), FIG. 14E. In the water bath, even though $\rho_{5CB}$<$\rho_{aq}$, the aqueous droplets were sequestered within a nematic phase of 5CB due to a strong repulsive elastic force. In the propanol-water bath, however, the ink droplets were continuously released as the solute-induced N-to-I phase transition of 5CB removed the elastic barriers (FIGS. 14F-14H).

Example 5: Controlled Release Activated by the Addition of Charged Amphiphiles, which may also be Accompanied by an Optical Response In this example, we demonstrate a fifth trigger for release of an immiscible or insoluble guest material from an anisotropic phase: the addition of the charged amphiphiles into the surrounding aqueous phase.

Figures 15A, 15B, 15C, 15D, 15E, 15F:
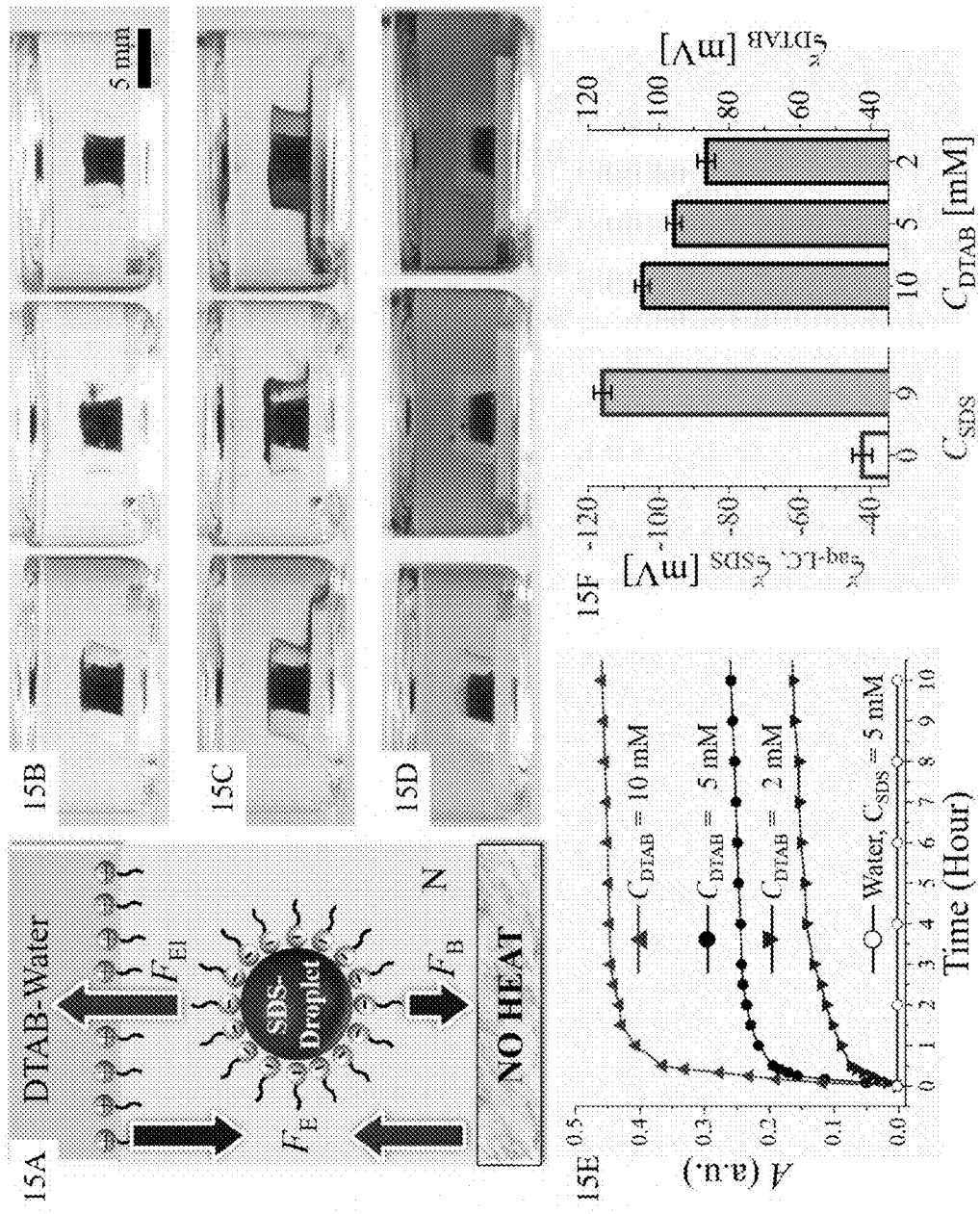
FIGS. 15A, 15B, 15C, 15D, 15E and 15F illustrate the isothermal release of negatively charged microdroplets ($C_{SDS}$=9 mM) from a nematic LC by the addition of positively charged surfactant (DTAB) into the baths.

The aqueous droplets dispersed in LCs contain amphiphiles (SDS) to prevent phase separation between the droplets and LC, and to induce a homeotropic anchoring at the LC-aqueous interface, FIG. 1A. Since SDS is negatively charged, the addition of positively charged amphiphiles to the overlying aqueous phase would induce electrostatic attraction between the aqueous phase and the guest droplets (FIG. 15A). If the introduced attraction can overcome the elastic repulsion, the droplets will be released into the bath.

In order to verify this concept, the mini-wells were filled with 5CB containing SDS (negatively charged) doped aqueous droplets ($C_{aq}$=20 v % and $C_{SDS}$=9 mM), and then submerged in water baths. We previously verified that at room temperature, microdroplets containing anionic amphiphile (SDS) were elastically trapped within a nematic LC under an aqueous phase (FIG. 1G). Addition of a cationic amphiphile (DTAB) to bulk aqueous environment, however, triggered the continuous ejection of red tracers into the overlying aqueous phase (FIGS. 15B-15D).

The amount of release was quantitatively described by measuring A as a function of time (FIG. 15E). In DTAB-water solutions, mini-wells exhibited a dramatic increase in A in first 30 minutes, followed by the gradual increment of A with time. A increases at higher $C_{DTAB}$. In contrast, addition of anionic amphiphiles (SDS) to the overlying aqueous phase did not initiate release (FIG. 15E). The rate of release of microdroplets correlated closely with the zeta potential $\xi$ of the LC-aqueous interface, as controlled by addition of SDS or DTAB (FIG. 15F), consistent with release controlled by a competition between $F_E$ and electrical double layer interactions ($F_{EI}$) (FIG. 15A).

Figures 16A, 16B, 16C, 16D, 16E, 16F, 16G, 16H, 16I, 16J, 16K:
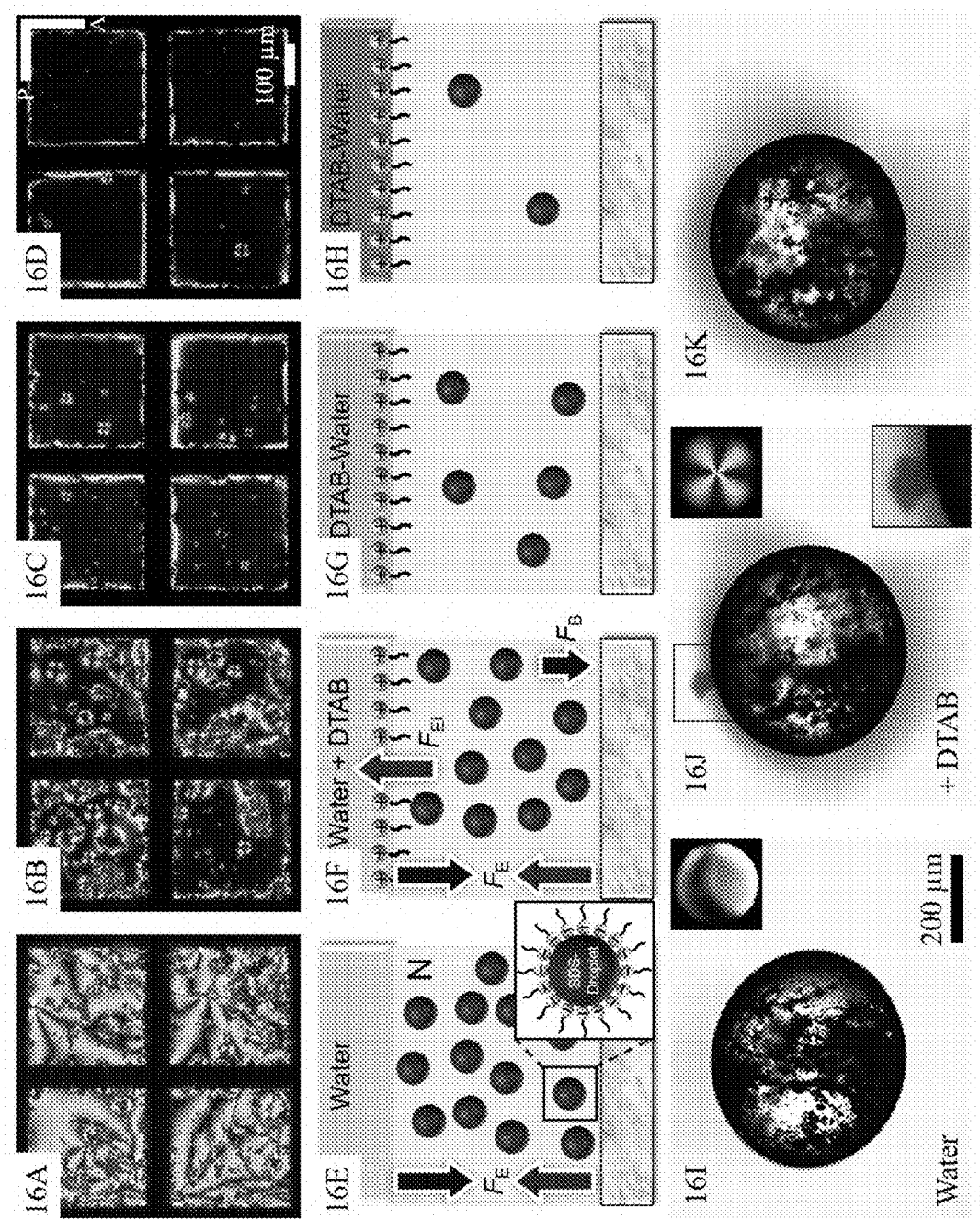
FIGS. 16A, 16B, 16C, 16D, 16E, 16F, 16G, 16H, 16I, 16J, and 16K shows the isothermal release of negatively charged microdroplets ($C_{aq}$=5 v %, $C_{SDS}$=9 mM) from a nematic LC by the addition of positively charged surfactant (DTAB) into the baths in different geometries.

In addition to the mini-wells, we demonstrated that the surfactant-triggered release can be realized in a range of geometries, such as thin LC films and LC emulsion droplets (FIG. 16). In a pure water, SDS-doped aqueous droplets were sequestered in the birefringent LC film (40 μm in thickness, FIGS. 16A and 16E). The addition of DTAB into the bath, however, triggered an optical response of the LC as well as the release of the contents of the microdroplets into the overlying aqueous phase (FIGS. 16B and 16F). The population of aqueous droplets gradually decreases with time indicating the release of droplets into the overlying aqueous phase (FIGS. 16B-16D and 16F-16H). Additionally, we also did not observe the release of aqueous droplets (negatively charged) from the LC droplet emulsified in a pure water (FIG. 16I), while the addition of DTAB initiated the release of aqueous droplets accompanied by optical reports (FIGS. 16I-16K).

The optically observable molecular reorientation is an example of another aspect of the disclosed compositions and methods. Specifically, the release trigger can be "sensed" by the LC host composition in an optically observable manner. Thus, an optical signal may be used to signal the contemporaneous release of the sequestered guest composition from the LC host composition.

FIGS. 16A and 16B and insets in FIGS. 16I and 16J show the micrographs of a LC thin film and LC droplet in an aqueous environment bath between crossed polarizers.

Liquid crystal contacting with aqueous environment exhibits a birefringent texture between crossed polarizers (FIG. 16A and inset in FIG. 16I) because LC molecules are aligned parallel to aqueous interfaces (planar anchoring). After the addition of surfactants, however, because the surfactants absorbed at LC-aqueous interfaces cause a vertical alignment of LC molecules at the aqueous interface (homeotropic anchoring), one can observe the changes in the optical appearance of LC; dark texture for thin LC films (FIG. 16B) and Malthese cross for LC droplets (Inset in FIG. 16J).

This data demonstrates that, in response to the addition of surfactants, our system can exhibit not only the release of microdroplets from liquid crystals, but also optical responses that are contemporaneous with the release.

For further confirmation on the role of surfactants, we compared the amount of release of negatively charged microdroplets from LCs in the water baths containing differently charged surfactants. As shown in FIG. 17A, the mini-wells filled with 5CB containing SDS-doped aqueous droplets ($C_{SDS}$=9 mM and $C_{aq}$=20 v %) were submerged into three baths with DTAB-water ($C_{DTAB}$=2 mM, left bath), pure water (middle bath), and SDS-water ($C_{SDS}$=2 mM, right bath).

Subsequently, we triggered the release of microdroplets by N-I phase transitions with $T_H$=50° C. and $T_C$=25° C. As shown in FIGS. 17B-17E, after the N-I phase transitions, the release of negatively charged microdroplets was observed in the baths with DTAB- and pure-water but not in the SDS-water bath. In addition, A in the DTAB-water was higher than the SDS-water. This behaviour confirm that the electrostatic interaction between droplets and overlying aqueous phase induced by the addition of charged surfactant plays a crucial role in the release of microdroplets from LCs.

Figures 18A, 18B, 18C, 18D, 18E, 18F, 18G:
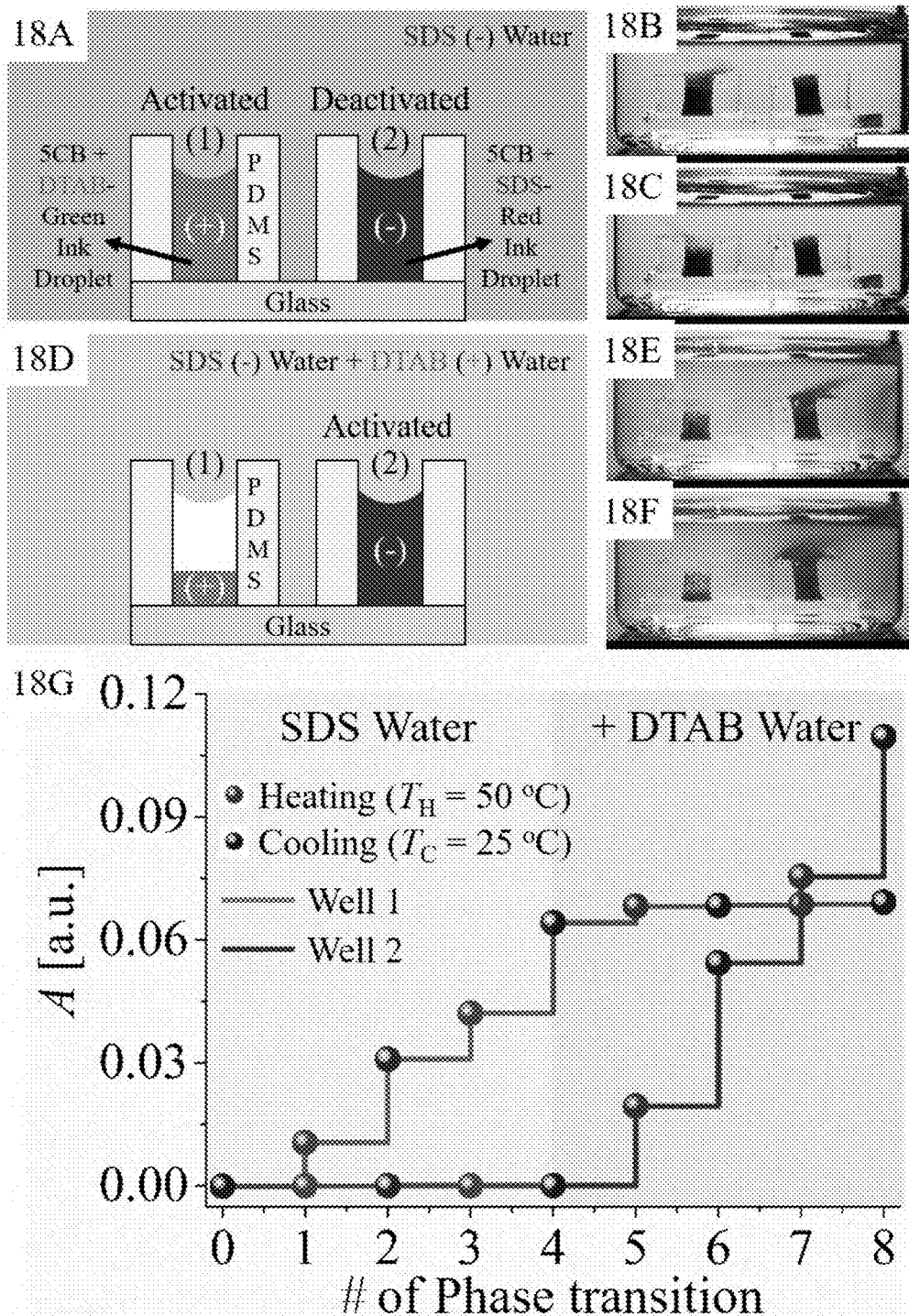
FIGS. 18A, 18B, 18C, 18D, 18E, 18F and 18G demonstrate the selective release triggered by a combination of chemical- and thermal stimuli.

Using the combination of thermal-(N-I phase transition) and chemical-stimuli (addition of charged amphiphile), we could design the system to selectively release the desired material. FIGS. 18A and 18D show schematic diagrams of the system to selectively release two different substances. Well-1 was filled with 5CB containing DTAB (+ charged) doped aqueous droplet (green tracer) and Well-2 was filled with 5CB containing SDS (− charged) doped aqueous droplets (red tracers). Subsequently, the wells were submerged into the SDS (− charged) water bath ($C_{SDS}$=2 mM) and heated and cooled repeatedly, FIG. 18A. Under these conditions, Well-1 released green tracer, whereas no detectable release was observed in Well-2 (FIGS. 18B, 18C, and 18G from $0^{th}$ to $4^{th}$ phase transition) indicating the electrostatic repulsion in Well-2 suppressed the ejection of microdroplets triggered by N-I phase transitions.

After 4 phase transitions, DTAB was introduced into the bath to reverse the surface charge, FIG. 18D. After the addition of the DTAB, release of red tracer was observed from Well-2 to accompany the phase transitions (FIGS. 18E, 18F, and 18G from $5^{th}$ to $8^{th}$ phase transitions).

Example 6: Controlled Release Activated by the Addition of Charged Polymers or Charged Biological Molecules, which May Also be Accompanied by an Optical Response In this example, we demonstrate a sixth trigger for release of an immiscible or insoluble guest material from an anisotropic phase: the addition of the charged polymers or charged biological molecules into the surrounding aqueous phase.

We have demonstrated that the addition of charged amphiphiles introduced interfacial interactions (e.g., electrostatic interaction) that can override the elastic barriers leading to the release of microdroplets from a nematic LC (FIGS. 15 and 16). Therefore, we hypothesized that the addition of charged additives such as polymers and biological molecules would also trigger the release of oppositely charged microdroplets from a nematic LC (FIG. 19A).

Figures 19A, 19B, 19C, 19D, 19E:
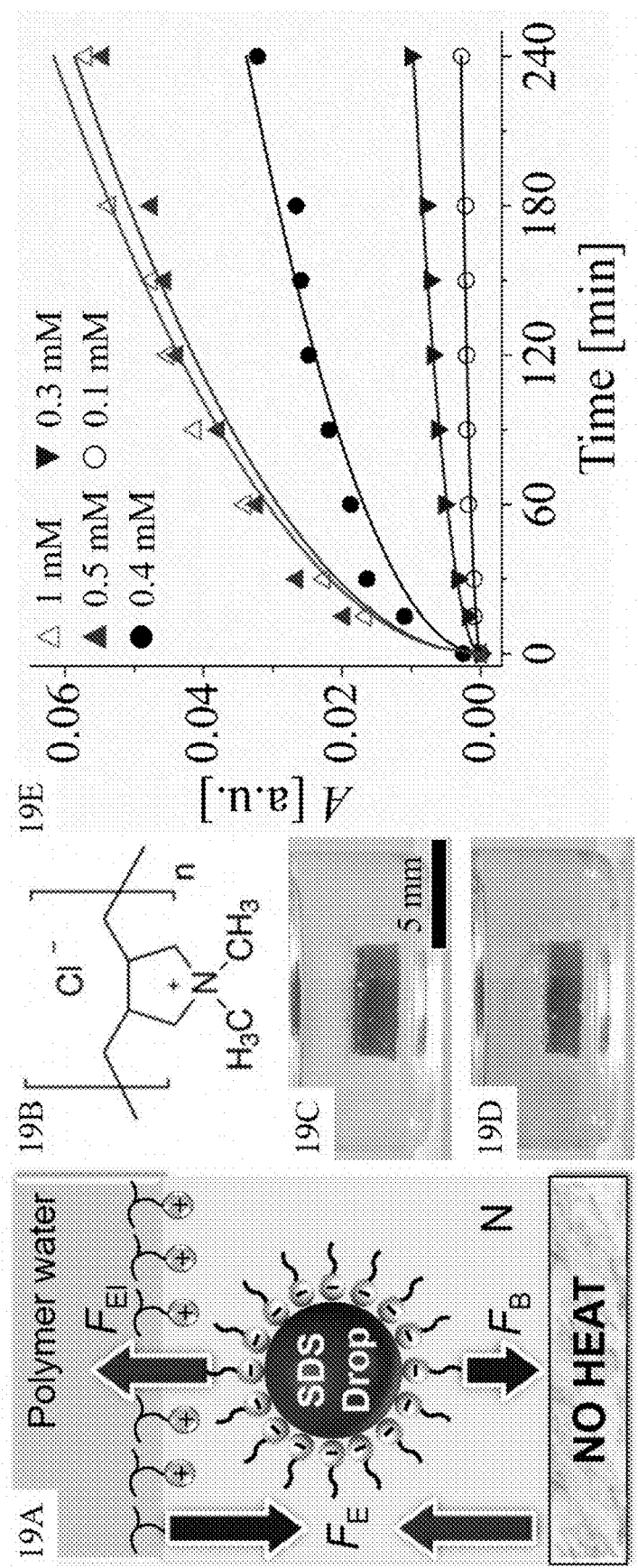
FIGS. 19A, 19B, 19C, 19D, and 19E demonstrate the release of microdroplets from a nematic LC by an addition of charged polymers.

In order to verify the concept, we used a commercially available polymer, poly(diallyldimethylammonium chloride) (PDADMAC), FIG. 19B. The measured value of Zeta potential at the LC-aqueous interface with the polymers was $\xi$=+50±5 mV. Therefore, a mini-well was filled with 5CB containing negatively charged microdroplets ($C_{SDS}$=2 mM, $C_{aq}$=30 v %). In a pure water, no measurable release of microdroplets was observed. After the addition of the polymer, however, the microdroplets were continuously released from a nematic LC even at T=25° C. (FIGS. 19C and 19D). The release rate increased with the increase in $C_{Polymer}$ and was saturated from $C_{Polymer}$~0.5 mM (FIG. 19E). In addition, we found that the absorbance curves are well fitted with a square root of time indicate the diffusion associated release of microdroplets.

In addition, we also demonstrated the triggered release of microdroplets from a LC based on interfacial charge interaction of biological molecules, lipopolysaccharides (LPS) from *Escherichia coli*. ξ at the LC-aqueous interface with LPS exhibits negative values and could be manipulated by $C_{LPS}$, FIG. 20A. In the absence of LPS, positively charged microdroplets ($C_{DTAB}$=2 mM) were sequestered in a nematic LC. However, the addition of LPS triggered not only the optical responses from a bright (FIG. 20F) to dark appearance (FIG. 20G) but also the ejection of the microdroplets continuously from the LC, as evidenced by the change in the color of overlying aqueous phases (FIGS. 20B-20E) and decrease in population of aqueous droplets within the thin LC film (40 μm in thickness, FIGS. 20F-20I). The rate of release was enhanced with increase in $C_{LPS}$ (FIGS. 20B-20E), consistent with release controlled by interfacial charge interactions (FIG. 20A).

Example 7: Controlled Release by Changing the pH of the Surrounding Environment

In this example, we demonstrate a seventh trigger for release of an immiscible or insoluble guest material from an anisotropic phase: changing the pH of the surrounding environment.

Figures 21A, 21B, 21C:
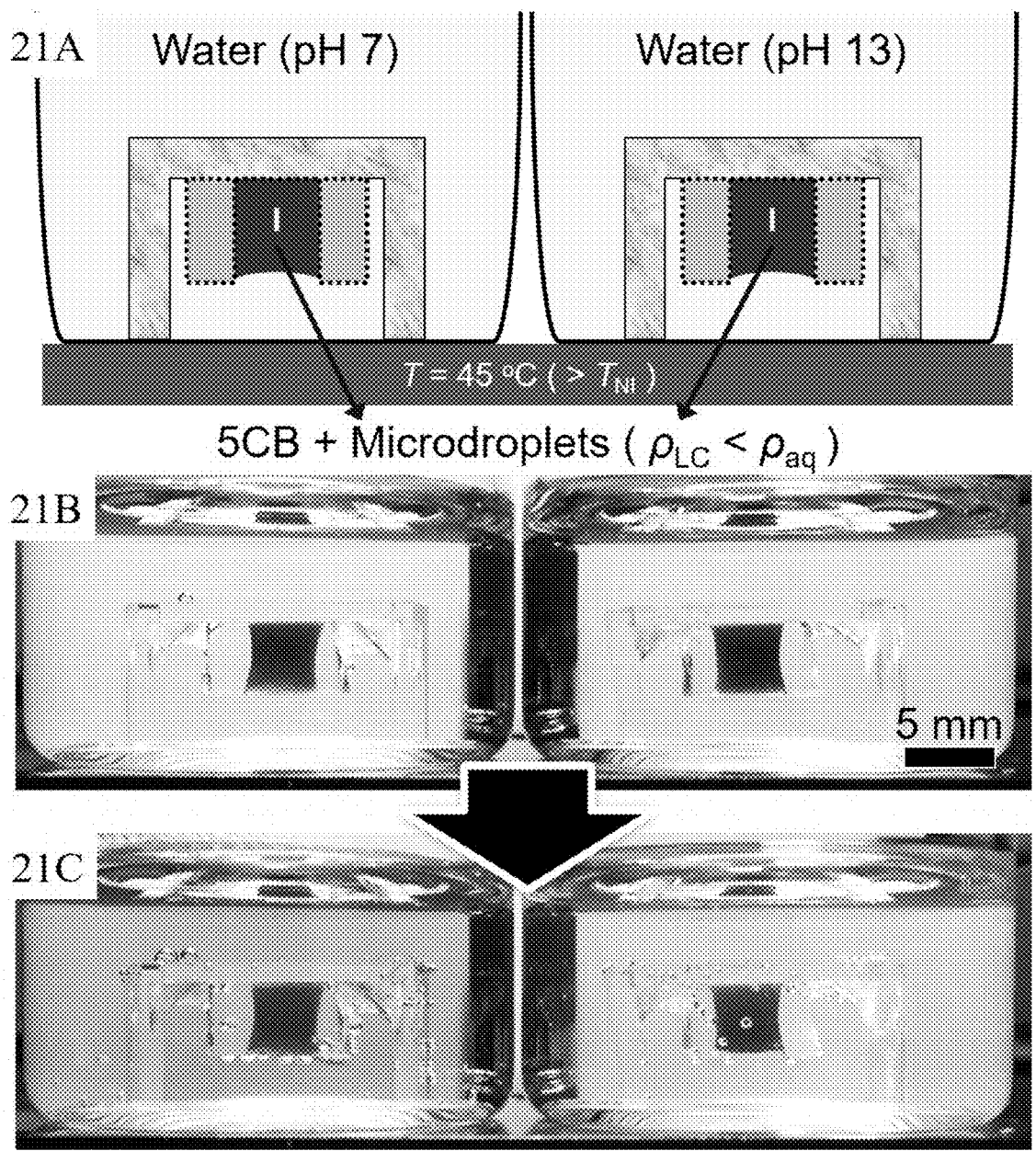
FIGS. 21A, 21B, and 21C show the role of electrostatic interfacial interactions on the release of microdroplets from LC.
Figures 24A, 24B, 24C, 24D, 24E, 24F, 24G, 24H:
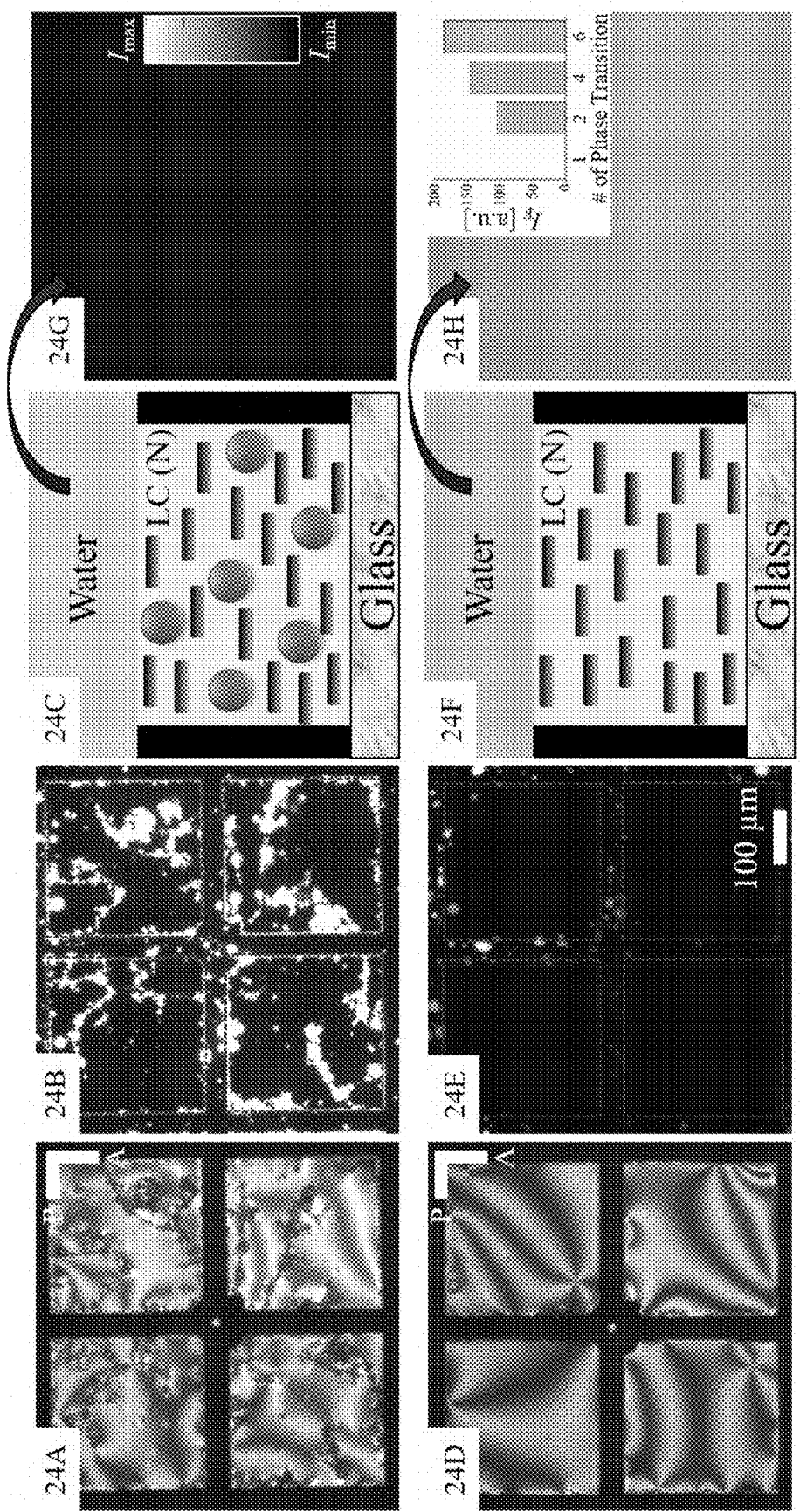
FIGS. 24A, 24B, 24C, 24D, 24E, 24F, 24G and 24H illustrate the triggered release of water-soluble solid microparticles from LC.
Figures 25A, 25B, 25C, 25D, 25E, 25F:
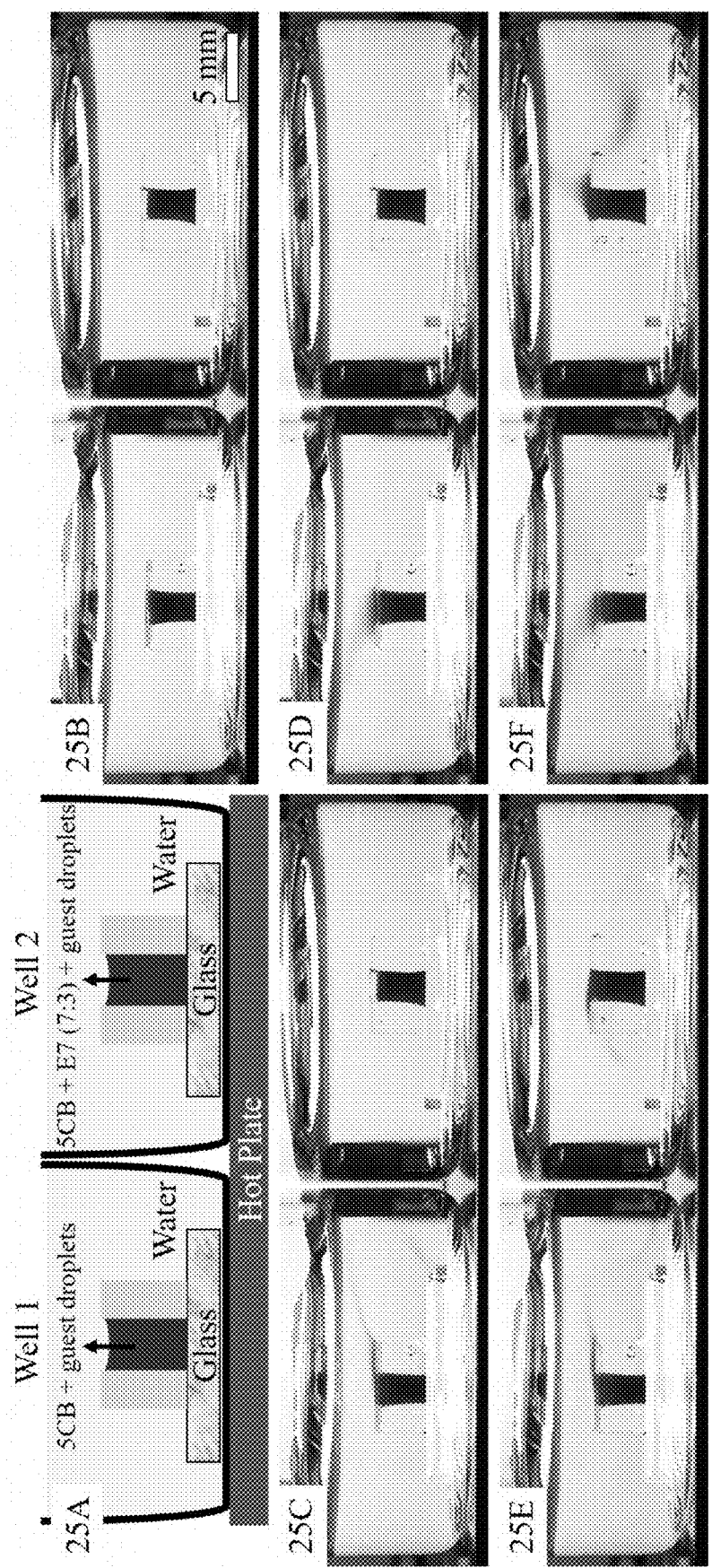
FIGS. 25A, 25B, 25C, 25D, 25E and 25F illustrate the selective release triggered by N-I phase transitions with LCs having different clearing temperature $T_{NI}$.
Figures 26A, 26B, 26C, 26D, 26E, 26F, 26G, 26H, 26I, 26J, 26K:
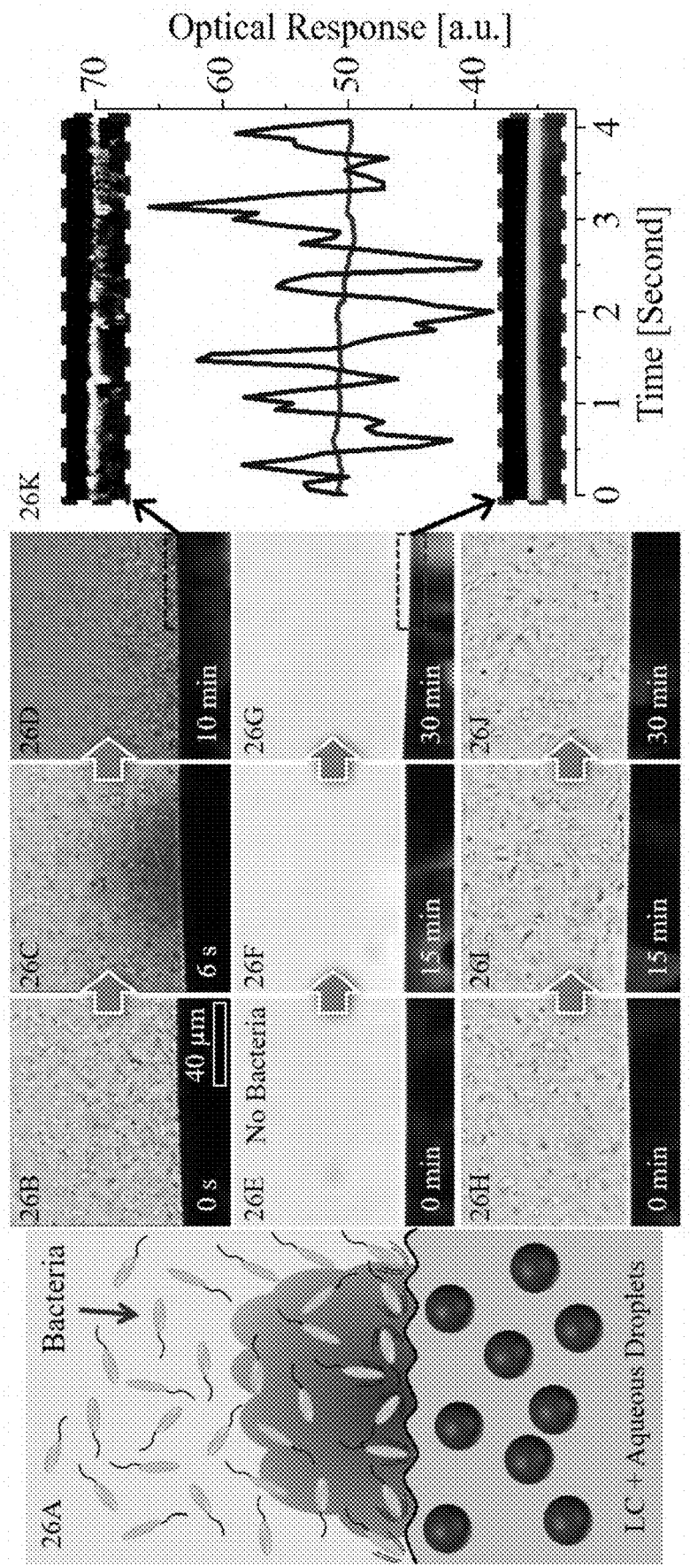
FIGS. 26A, 26B, 26C, 26D, 26E, 26F, 26G, 26H, 26I, 26J, and 26K illustrate the release of microdroplets triggered by motion of motile bacteria.

In addition to the release of microdroplets triggered by the addition of charged surfactants and polymers, we also demonstrated the release system that responded to changes in pH of surrounding environment. As shown in FIG. 21A, inverted mini-wells filled 5CB containing negatively charged microdroplets ($C_{aq}$=10 v %, $C_{SDS}$=9 mM) were placed in a pure water (pH 7, left bath) and an alkaline water (pH 13, right bath). Subsequently, the baths were heated to 45° C. (>$T_{NI}$) to cause a N-to-I phase transition. Due to the negative buoyant force ($\rho_{5CB} < \rho_{aq}$) and the absence of elastic barrier in an I phase, aqueous droplets were released from an isotropic phase of 5CB into a surrounding water (left bath in FIGS. 21B and 21C). In an alkaline water, however, the release of microdroplets was significantly suppressed due to the repulsive interaction between an LC-alkaline water interface (negative charge) and SDS doped microdroplet (negative charge).

Example 8: Controlled Release Activated by the Convection Flow in the Host Composition In this example, we demonstrate an eighth trigger for release of an immiscible or insoluble guest material from an anisotropic phase: convective flow induced by addition of amphiphiles into the surrounding aqueous phase.

We have found that material flows introduced in LCs can provide a hydrodynamic force for guest droplets to overcome the elastic repulsion and thus activate the release. In LCs, material flows can be induced by numerous ways such as thermal expansion [52, 53], unsteady temperature field [54-56], and the difference in interfacial tension (Marangoni flow) [57-62]. In addition, we found that strong convective flows can be induced in LCs contacting with surfactant-water solutions.

In order to cause the convective flow in LCs, we introduced nonionic surfactant, Triton X-100, into the surrounding aqueous phase contacting with LCs. Here, we intentionally used a nonionic surfactant to establish that the activated release occurred by the convection flow without the contribution of electrostatic interaction resulting from the use of charged surfactant.

FIGS. 22A and 22B show the micrographs of 5CB contacting with pure water and Triton X-100 water solution ($C_{Triton}$=10 mM). When 5CB is in contact with a pure water, no flow was observed, FIG. 22A, whereas a strong convective flow was generated in LC layer contacting with Triton-water solution, FIG. 22B.

To verify whether the induced flow can trigger the release of guest droplets from nematic LCs, the mini-wells filled with 5CB containing aqueous droplets ($C_{aq}$=20 v %, $C_{SDS}$=9 mM) were submerged into the water baths with $C_{Triton}$=5 (left bath), 10 (middle bath), and 100 mM (right bath). As shown in FIGS. 22C-22F, we could observe the significant release of aqueous droplets from a nematic LC. The amount of release (=red color density in the bath) gradually increases as the time and $C_{Triton}$ increase. The result demonstrate that the surfactant induced convective flow in LC can provide hydrodynamic forces for microdroplets enough to override the elastic barriers.

Example 9: Extended Applicability of Controlled Release Methods

In the previous examples, we demonstrated the disclosed controlled release methods using thermotropic nematic LC as an exemplary host material. However, various liquid crystals may be employed in the host compositions, including thermotropic, lyotropic, and polymeric LCs. In addition to nematic phase, numerous phases of LC suitable for use in the host compositions include twist-bend nematic, ferroelectric, smectic, blue phases, and cholesteric phases. The disclosed systems and methods can be also designed to be triggered at desired temperature because the N-I phase transition temperature of LC can be readily manipulated.

For example, FIGS. 23A-23D show an example of a cholesteric (chiral nematic)[63] LC system that was triggered by the touch of a human finger. The N-to-I phase transition was designed to be triggered at physiological temperature, resulting in a change in Bragg-diffracted light (as used in electronic paper[64] and LC thermometers[65]) and the release of a well-defined dose of chemical microcargo. In contrast to other thermally responsive materials that release chemical agents continuously in an amount that is determined by the duration of the thermal trigger or exhaustion of the reservoir of agent (e.g., thermally responsive hydrogels [66, 67]), the LC signals optically the release of each well-defined aliquot, thus permitting control and monitoring of dosing, reducing risks of toxicity, extending the lifetime of the material to multiple triggering events (e.g., for drug delivery, fragrance or cleaning agents from material surfaces touched by human hands or warm blooded animals).

In the previous examples, we demonstrated the disclosed controlled release methods using aqueous droplets as an exemplary guest material. However, any guest materials in any phase state (liquid, solid, or gas) can be used in the disclosed controlled release systems and methods, unless the proposed guest material is miscible or soluble in the anisotropic phase that is used.

For example, we successfully utilized the disclosed systems and methods to deliver solid microparticles from a LC to a surrounding environment. Furthermore, we were able to tune the dosage of microparticles released by varying the number of phase transitions (FIGS. 24A-24H).

The disclosed systems and methods are also not limited to guest materials that are sequestered within the specific liquid crystals used in the previous examples. Instead, a variety of anisotropic phases can be used, and controlled release can be staged in many other nematic LCs, including lyotropic LCs.

For example, on the basis of the phase transition mechanism illustrated in Example 1, we utilized LCs having different $T_{NI}$ to selectively release guest materials from one or both of two different anisotropic phases (FIGS. 25A-25F). In addition, since NLCs include edible lyotropic species, such as lyotropic chromonic liquid crystals [68], the disclosed systems and methods can be made suitable for drug delivery applications.

As the skilled, the disclosed systems and methods are not limited to the specific processes used in these examples. As a non-limiting example, the triggering heat that can be used in the disclosed systems and methods can be produced in a number of different ways, including, without limitation, using a focused laser beam or joule heating. For example, FIGS. 3A-G illustrate heat-activated release using an electric (Joule) heater.

Example 10: Simultaneous Generation of Optical Signals and Release of Microcargo from Liquid Crystals Triggered by Motility of Bacteria In this Example, we report the unexpected discovery that the swimming of motile bacterial near the surface of liquid crystal containing elastically sequestered microcargo can lead to the ejection of the microcargo from LC.

Specifically, we demonstrate that motile bacterial (*Escherichia coli*) can transmit mechanical forces to a LC interface as evidenced by changes in optical appearance (FIG. 26K) and trigger the release of microcargo containing anti-bacterial agents (DTAB), FIGS. 26A-26D. In contrast, no optical responses and ejections of microcargo were observed in the absence of bacteria (FIGS. 26E-26G) or presence of weakly motile bacteria (FIGS. 26H-26J). Difference in the optical appearances at LC interfaces with and without bacteria is shown in FIG. 26K.

In summary, the response of the LC can report optically the presence of bacteria, and also release microcargo (e.g., antibacterial agent, antibiofilm agent, chemoattractant, nutrient, etc.) to interact with the bacteria. If the microcargo is an antimicrobial agent, once killed, the bacterial cells will cease to be motile, and thus release of the antibacterial agent will cease. The LC will optically report that the bacteria have been killed.

Accordingly, anisotropic fluid such as NLCs offer the basis of a general and facile method for the release of target materials triggered by interactions with motile bacterial systems. A key advantage of this system is that it only releases an active agent in the presence of motile cells. This preserves the active agent for use only when bacteria are present. It minimizes unwanted release of agents, potentially causing toxicity to other cells types. The LC can also optically report the arrival and killing of the bacteria.

Example 11: Materials and Methods

As applicable and unless otherwise noted, the following materials and methods were used in the preceding examples.

Materials

Nematic liquid crystals, 4'pentyl-cyanobiphenyl (5CB) and E7, were purchased from HCCH (Jiangsu Hecheng Display Technology Co., LTD). Water-soluble dyes that were used as tracers were purchased from MontBlanc. Sodium dodecyl sulfate (SDS), dodecyltrimethylammonium bromide (DTAB), Triton X-100, dimethyloctadecyl[3-(trimethoxysilyl)propyl] ammonium chloride (DMOAP), lipopolysaccharides (LPS), and FITC-dextran were purchased form Sigma-Aldrich. Lysogeny broth was purchased from Becton, Dickinson and Company. Transmission electron microscopy (TEM) grids (40 µm in thickness) were purchased from Electron Microscopy Sciences. The polymeric alignment layer (PI2555) was purchased from HD Microsystems. A Sylgard 184 silicone elastomer kit for preparing polydimethylsiloxane (PDMS) was purchased from Dow Corning. Biopsy punches were obtained from Integra Miltex.

Preparation of LCs Containing Aqueous Microdroplets

To stabilize dispersions of aqueous microdroplets in the LCs, we first added either SDS or DTAB at a specified concentration to the aqueous solutions of water-soluble dyes. The aqueous solutions of dyes were emulsified into the nematic LCs (5CB and E7) by vortexing (for 1 min at 3000 rpm) and sonication (10 min). Each surfactant was present at a concentration below its critical micelle concentration [69].

Preparation of LC-Filled Mini-Wells

Mini-wells were made of PDMS. Elastomer base and curing agent from a Sylgard elastomer kit were mixed in the ratio of 10:1. The mixture was then cured at 60° C. for 2 hours. A cured PDMS disk with a diameter of 6 mm was obtained using a 6 mm biopsy punch. Subsequently, a cylindrical hole with a diameter of 3 mm was punched at the center of the 6 mm disk using a second biopsy punch. The PDMS was treated with an oxygen plasma for 20 seconds and bonded to a glass substrate to create a mini-well with a depth of 3.5 mm. After fabrication, the mini-wells were stored for at least 3 days prior to filling with 18 µL of LCs containing guest microdroplets. Subsequently, the mini-wells were submerged into glass vials filled with 2 mL of aqueous solutions. If used prior to 3 days, the PDMS surface was sufficiently hydrophilic that water spread between the LC phase and PDMS surface.

Preparation of Samples for the Microscopic Observations of Microdroplet Transport For microscopic observations in FIGS. 6, 7, 20B-20E, 22A, 22B, and 26B-26J, the experimental cells were assembled from glass plates coated with an alignment layer (PI2555) or DMOAP which cause planar and homeotropic alignment, respectively. PI2555 substrates were rubbed to achieve unidirectional alignment of n and were assembled in an anti-parallel fashion. The gaps between the plates were set by using double-sided tape at 100-300 µm. The cavity was filled with the LC containing microdroplets ($C_{aq}$=0.5-3 v %; $C_{SDS}$=9 mM) and then observed under a microscope.

Preparation of LC Films

As described in FIGS. 8, 16A-16D, 20A-20F, and 23, TEM grids (40 µm in thickness) were placed onto DMOAP-coated glass substrates and filled with LC-containing the aqueous microdroplets. Subsequently, the films were submerged into water baths. The DMOAP-coated glass was used to orient the LC perpendicular to the glass substrate and prevent penetration of the aqueous phase between the LC and glass substrate.

Preparation of Double Emulsions Shown in FIG. 16I-16K

A 0.1 µL volume of LC containing aqueous microdroplets was placed on a DMOAP-coated glass surface. Subsequently, the glass plate was submerged into a water bath (2 mL) to form a LC droplet. To initiate the release of microdroplets, 0.1 mL of DTAB-water ($C_{DTAB}$=200 mM) was introduced into the bath to achieve a final concentration of 10 mM.

Preparation of Mini-Wells Shown in FIG. 18A-18F

Mini-wells 1 and 2 were filled with 5CB containing either DTAB-doped microdroplets (green tracer) and SDS-doped microdroplets (red tracer), respectively. The wells were submerged into 3.5 mL of aqueous SDS solution ($C_{SDS}$=3 mM), FIG. 18A. After 4 phase transitions, 200 µL of aqueous DTAB ($C_{DTAB}$=50 mM) was introduced into the bath to reverse the surface charge (FIG. 18D).

Preparation of Cholesteric LC in FIGS. 23A-23D 20 weight percentage of chiral dopant (S-811) was dissolved in 5CB. The N-to-I phase transition temperature of the LC was measured to be 27° C.

Preparation of Bacterial Dispersions Used in FIG. 26

*Escherichia coli* (strain MG1655) were grown aerobically in 1 mL of lysogeny broth (LB) [1% (w/v) tryptone, 0.5% (w/v) yeast extract, and 1% (w/v) NaCl] at T=37° C. with agitation (200 rpm) for 12 hours. To achieve motile bacteria, the culture was diluted into 2 mL of fresh LB in a 1:100 ratio and the bacteria were grown again for 2 hrs (T=37° C., 200 rpm). The density of bacteria in the resulting dispersion was $10^7$-$10^8$ cells/mL.

Temperature Control

Temperature was controlled using a STC200 hot stage and controller (Instec Inc.) with 0.1° C. accuracy. Both heating and cooling were achieved by circulation of cold water. The rate of temperature change was typically ±15° C./min.

Absorbance Measurement

6 µL of aqueous solution was collected from baths contacting the LC after each N-I phase transition (FIGS. 1G-1J, 2, 5, 17E, and 18G) or every 3 minutes (FIGS. 11E, 15E and 19E). Prior to collection of a sample, the baths were gently agitated to uniformly mix the tracer released from the LC through the overlying aqueous solution. We measured the absorbance using a NanoDrop 2000 (Thermo Scientific) spectrophotometer.

Zeta Potential Measurement

5CB (0.01 v %≥$C_{5CB}$≥0.001 v %) was emulsified in aqueous solution (water or aqueous solutions of SDS or DTAB) using a homogenizer. Zeta potentials (ξ) on the aqueous side of the LC-aqueous interface were measured using a Zetasizer Nano (Malvem Instruments Ltd).

Comparison of the Magnitudes of Elastic and Thermal Energies

The elastic interaction energy $E_E$ between a droplet (R>K/W, homeotropic surface anchoring) and a nematic interface (planar surface anchoring) can be written as [30-32]:

$$E_E = A^2 \pi K \frac{3}{4} \frac{R^4}{z^3} \quad (8)$$

where A is a numerical factor (A=2.04)[32], R is the radius of the guest droplet, z is the distance between the center of the droplet and nematic interface, and K is the Frank elastic constant of the LC (K=($K_1$+$K_3$)/2 where $K_1$ and $K_3$ are elastic constants for splay and bend deformations, respectively [25]). As a droplet approaches a nematic interface, $E_E$ increases and exhibits a maximum at z=R. Because K~$10^{-12}$ N for typical thermotropic LCs [28, 29, 70], the maximum elastic interaction energy $E_E^{Max}$ for a droplet with R=1 µm is 9.8·$10^{-18}$ N. $k_B T$ is 4.1·$10^{-21}$ N at T=25° C., and thus $E_E^{Max}$=2383$k_B$T.

Comparison of the Magnitudes of Elastic Forces and Buoyant Forces

The elastic repulsive force $F_E$ between a droplet (R>K/W, homeotropic surface anchoring) and a nematic interface (planar surface anchoring) can be written as follows [31, 32]:

$$F_E = \pi K A^2 \frac{3}{4} \left(\frac{R}{z}\right)^4 . \quad (9)$$

$F_E$ is valid at z≥R and has a maximum at z=R; $F_E^{Max}$=(3/4) $\pi K A^2$. At z<R, $F_E$ needs to be modified (see below). The buoyant force $F_B$ acting on a microdroplet in LC is $F_B$=(4/3) $\pi R^3 g(\rho_{LC}-\rho_{aq})$. At 25° C., $K_{5CB}$=7.3·$10^{-12}$ N [29], $K_{E7}$=14.4·$10^{-12}$ N [70], $\rho_{5CB}$=1.010 g/cm³ [71], $\rho_{E7}$=1.057 g/cm³ [72], $\rho_{aq}$=1.018 g/cm³ for red dye and $\rho_{aq}$=1.012 g/cm³ for green dye [72]. Therefore, for a droplet (red dye) of R=3 µm in 5CB, $F_E^{Max}$=8072$F_B$ and for a droplet (green dye) of R=4 µm in E7, $F_E^{Max}$=1194 $F_B$.

Interfacial tension force $F_{IT}$

When a droplet is near an interface dividing two immiscible fluids (N and I phases in our case), $F_{IT}$ arises to minimize the surface tension energy [38]. Typically, droplets are stabilized at the interface between two immiscible fluids because interface tensions are similar in magnitude to each other. In thermotropic LCs, however, $\sigma_{NI}$ is much smaller than the surface tension ($\sigma_{aq-LC}$) at aqueous-N or -I interface. In case of 5CB, for example, at T=35° C., $\sigma_{aq-N}$≈7·$10^{-3}$ J/m², $\sigma_{aq-I}$≈6·$10^{-3}$ J/m², and $\sigma_{NI}$≈$10^{-5}$ J/m² ($\sigma_{aq-N}$>$\sigma_{aq-I}$>>$\sigma_{NI}$) [71, 73]. As a result, the aqueous droplets at the N-I interface are expelled to the I phase [38]. For simplicity, we assume that $F_{IT}$ is active only when the droplet contacts the N-I interface; $F_{IT}$=0 at |z|≥R.

Elastic Force $F_{E^*}$

When a microdroplet penetrates the N-I interface (−R<z<R), the elastic force acting on the microdroplet is modified by $F_{E^*}$ [34, 43]. Whereas $F_E$ acts to keep droplets in the nematic phase, $F_{E^*}$ expels the droplets into the isotropic phase to minimize the elastic free energy. In the weak anchoring regime (R<K/W), $F_{E^*}$ originates from the anchoring of the director at the droplet surface and the director deformation in the bulk nematic phase, and can be written as $$F_{E^*}(R < K/W) = \{WR f_1(z/R)\}_{Surface} + \left\{\frac{(WR)^2}{K} f_1(z/R)\right\}_{Bulk}, \quad (10)$$

where $f_1$(z/R) is a dimensionless function of the penetration depth of droplet into a N phase [34, 43].

In the strong anchoring regime (R>K/W), $F_{E^*}$ is given by $$F_{E^*}(R>K/W) = \{K f_2(z/R)\}_{Bulk}, \quad (11)$$

where $f_2$ (z/R) is a dimensionless function of the penetration depth of the droplet into the N phase [34, 43]. Andrienko et al [42] found that the force acting on a particle passing through a N-I interface is linearly proportional to the penetration depth z/R. In our evaluation, therefore, we simplified the dimensionless functions to $$f_1(z/R) = \alpha\left(\mp 1 - \frac{Z}{R}\right) \text{ and } f_2(z/R) = \beta\left(\mp 1 - \frac{Z}{R}\right)$$

where − and + are for N-to-I and I-to-N phase transitions, respectively.

Parameters in the Calculations

For 5CB, at T=25° C. $K_{5CB}$=7.3·$10^{-12}$ N [29], $\rho_{5CB}$=1.010 g/cm³ [71] and at T 35° C.(=$T_{NI}^{5CB}$) $K_{5CB}$=3·$10^{-12}$ N [29], $\rho_{5CB}$=1.000 g/cm³ [71], W=$10^{-6}$ J/m² [28], and $\eta_{5CB}$=0.015 kg/m·s [74]. $\sigma_{NI}$ of 5CB is 1.5·$10^{-5}$ J/m² [73]. In our calculation, however, $\sigma_{NI}$=1.5·$10^{-6}$ J/m² was used because the surfactants added to the microdroplets reduce the surface tension [75-77]. For E7, $K_{E7}$=10.25 (40° C.), 7 (50° C.), 2 pN (59° C.) [70], and $\rho_{E7}$=1.045 (40° C.), 1.037 (50° C.), 1.028 g/cm³ (59° C.) [72]. α=9.9, β=0 for R<K/W and α=0, $\beta$=4.4 for R>K/W. $\alpha$ and $\beta$ were chosen based on the experimental results. L=1 mm for FIG. 9 and L=3.5 mm for FIG. 11G.

For red dye droplets (FIG. 9), $\rho_{aq}$=1.018 g/cm$^3$ (25° C.) and 1.013 g/cm$^3$ (35° C.)$^{35}$. For green dye droplets (FIG. 11G), $\rho_{aq}$=1.004 g/cm$^3$ (40° C.), 0.996 g/cm$^3$ (50° C.), and 0.987 g/cm$^3$ (59° C.)$^{35}$.

Conclusion to the Examples

In conclusion, we demonstrate here that anisotropic fluid such as nematic LCs offer the basis of a general and facile method for the controlled-release of target materials by simply changing temperature, introducing shear stress, adding amphiphiles, and/or adding motile bacteria. The physical mechanisms of the heat-triggered controlled release were explained by a simple model that agrees well with the experiments. We also qualitatively analyzed the mechanisms of the controlled release facilitated by the introduction of amphiphiles causing electrostatic force, hydrodynamic force, or both. In all cases, release of guest material sequestered within an anisotropic phase was accomplished by changing the elastic repulsion forces preventing release and/or introducing additional forces to the system sufficient to overcome these elastic repulsion forces.

The simplicity of the proposed systems and methods (i.e., they do not require any complex instrumentation (e.g., microchips or micro-scaled pump) or chemical modification) suggest that they will find applications not only in drug delivery but also in a variety of other fields, including sensors, micro-cargo transportation, and micro- and optofluidics.

Those skilled in the art will recognize, or be able to ascertain using no more than routine experimentation, numerous equivalents to the specific materials and methods described herein. Such equivalents are considered to be within the scope of this disclosure.

REFERENCES CITED IN EXAMPLES SECTION

1 J. M. Anderson and M. S. Shive. "Biodegradation and Biocompatibility of Pla and Plga Microspheres" *Adv. Drug Deliv. Rev.* 28, 5-24 (1997).
2 G. Zhu, S. R. Mallery and S. P. Schwendeman. "Stabilization of Proteins Encapsulated in Injectable Poly (Lactide-Co-Glycolide)" *Nat. Biotechnol.* 18, 52-57 (2000).
3 J. Panyam and V. Labhasetwar. "Biodegradable Nanoparticles for Drug and Gene Delivery to Cells and Tissue" *Adv. Drug Deliv. Rev.* 55, 329-347 (2003).
4 A. Kumari, S. K. Yadav and S. C. Yadav. "Biodegradable Polymeric Nanoparticles Based Drug Delivery Systems" *Colloids Surf. B* 75, 1-18 (2010).
5 N. Kolishetti, S. Dhar, P. M. Valencia, L. Q. Lin, R. Kamik, S. J. Lippard, R. Langer and O. C. Farokhzad. "Engineering of Self-Assembled Nanoparticle Platform for Precisely Controlled Combination Drug Therapy" *PNAS* 107, 17939-17944 (2010).
6 A. M. Derfus, G. von Maltzahn, T. J. Harris, T. Duza, K. S. Vecchio, E. Ruoslahti and S. N. Bhatia. "Remotely Triggered Release from Magnetic Nanoparticles" *Adv. Mater.* 19, 3932-3939 (2007).
7 T. Hoare, J. Santamaria, G. F. Goya, S. Irusta, D. Lin, S. Lau, R. Padera, R. Langer and D. S. Kohane. "A Magnetically Triggered Composite Membrane for on-Demand Drug Delivery" *Nano Lett.* 9, 3651-3657 (2009).
8 J. Ge, E. Neofytou, T. J. Cahill, R. E. Beygui and R. N. Zare. "Drug Release from Electric-Field-Responsive Nanoparticles" *ACS Nano* 6, 227-233 (2012).
9 B. P. Timko, T. Dvir and D. S. Kohane. "Remotely Triggerable Drug Delivery Systems" *Adv. Mater.* 22, 4925-4943 (2010).
10 A. Barhoumi, Q. Liu and D. S. Kohane. "Ultraviolet Light-Mediated Drug Delivery: Principles, Applications, and Challenges" *J. Control. Release* 219, 31-42 (2015).
11 J. A. Cohen, T. T. Beaudette, J. L. Cohen, K. E. Broaders, E. M. Bachelder and J. M. J. Frechet. "Acetal-Modifi Ed Dextran Microparticles with Controlled Degradation Kinetics and Surface Functionality for Gene Delivery in Phagocytic and Non-Phagocytic Cells" *Adv. Mater.* 22, 3593-3597 (2010).
12 S. Aryal, C.-M. Jack and L. Zhang. "Polymer-Cisplatin Conjugate Nanoparticles for Acid-Responsive Drug Delivery" *ACS Nano* 4, 251-258 (2010).
13 D. C. Hyun, P. Lu, S.-I. Choi, U. Jeong and Y. Xia. "Microscale Polymer Bottles Corked with a Phase-Change Material for Temperature-Controlled Release" *Angew. Chem. Int. Ed.* 52, 10468-10471 (2013).
14 N. Garti and C. Bisperink. "Double Emulsions: Progress and Applications" *Curr. Opin. Colloid Interface Sci.* 3, 657-667 (1998).
15 D. J. McClements, E. A. Decker, Y. Park and J. Weiss. "Structural Design Principles for Delivery of Bioactive Components in Nutraceuticals and Functional Foods" *Crit. Rev. Food Sci. Nutr.* 49, 577-606 (2009).
16 W. J. Duncanson, T. Lin, A. R. Abate, S. Seiffert, R. K. Shah and D. A. Weitz. "Microfluidic Synthesis of Advanced Microparticles for Encapsulation and Controlled Release" *Lab Chip* 12, 2135-2145 (2012).
17 M. Nollet, M. Depardieu, M. Destribats, R. Backov and V. Schmitt. "Thermo-Responsive Multi-Cargo Core Shell Particles" *Par. Part. Syst. Charact.* 30, 62-66 (2013).
18 B. Herranz-Blanco, L. R. Arriaga, E. Makila, A. Correia, N. Shrestha, S. Mirza, D. A. Weitz, J. Salonen, J. Hirvonen and H. A. Santos. "Microfluidic Assembly of Multistage Porous Silicon-Lipid Vesicles for Controlled Drug Release" *Lab Chip* 14, 1083-1086 (2014).
19 J. T. Santini Jr., M. J. Cima and R. Langer. "A Controlled-Release Microchip" *Nature* 397, 335-338 (1999).
20 A. C. R. Grayson, I. S. Choi, B. M. Tyler, P. P. Wang, H. Brem, M. J. Cima and R. langer. "Multi-Pulse Drug Delivery from a Resorbable Polymeric Microchip Device" *Nat. Mater.* 2, 767-772 (2003).
21 D. A. LaVan, T. McGuire and R. Langer. "Small-Scale Systems for in Vivo Drug Delivery" *Nat. Biotechnol.* 21, 1184-1191 (2003).
22 J. H. Prescott, S. Lipka, S. Baldwin, N. F. Sheppard Jr., J. M. Maloney, J. Coppeta, B. Yomtov, M. A. Staples and J. T. Santini Jr. "Chronic, Programmed Polypeptide Delivery from an Implanted, Multireservoir Microchip Device" *Nat. Biotechnol.* 24, 437-438 (2006).
23 H.-K. A. Tsai, E. A. Moschou, S. Daunert, M. Madou and L. Kulinsky. "Integrating Biosensors and Drug Delivery: A Step Closer toward Scalable Responsive Drug-Delivery Systems" *Adv. Mater.* 21, 656-660 (2009).
24 N.-T. Nguyen, S. A. M. Shaegh, N. Kashaninejad and D.-T. Phan. "Design, Fabrication and Characterization of Drug Delivery Systems Based on Lab-on-a-Chip Technology" *Adv. Drug Deliv. Rev.* 65, 1403-1419 (2013).
25 P. G. de Gennes and J. Prost. *The Physics of Liquid Crystals* (Clarendon Press, 1993).
26 M. Kleman and O. D. Lavrentovich. *Soft Matter Physics: An Introduction* (Springer, 2003).

27 T. A. Wood, J. S. Lintuvuori, A. B. Schofield, D. Marenduzzo and W. C. K. Poon. "A Self-Quenched Defect Glass in a Colloid-Nematic Liquid Crystal Composite" *Science* 334, 79-83 (2011).

28 Y.-K. Kim, S. V. Shiyanovskii and O. D. Lavrentovich. "Morphogenesis of Defects and Tactoids During Isotropic Nematic Phase Transition in Self Assembled Lyotropic Chromonic Liquid Crystals" *J Phys.: Condens. Matter* 25, 404202 (2013).

29 A. Bogi and S. Faetti. "Elastic, Dielectric and Optical Constants of 4'-Pentyl-4-Cyanobiphenyl" *Liq. Cryst.* 28, 729-739 (2001).

30 P. Poulin, H. Stark, T. C. Lubensky and D. A. Weitz. "Novel Colloidal Interactions in Anisotropic Fluids" *Science* 275, 1770-1773 (1997).

31 O. P. Pishnyak, S. Tang, J. R. Kelly, S. V. Shiyanovskii and O. D. Lavrentovich. "Levitation, Lift, and Bidirectional Motion of Colloidal Particles in an Electrically Driven Nematic Liquid Crystal" *Phys. Rev. Lett.* 99, 127802 (2007).

32 S. B. Chernyshuk and B. I. Lev. "Theory of Elastic Interaction of Colloidal Particles in Nematic Liquid Crystals near One Wall and in the Nematic Cell" *Phys. Rev. E* 84, 011707 (2011).

34 J. L. West, A. Glushchenko, G. Liao, Y. Reznikov, D. Andrienko and M. P. Allen. "Drag on Particles in a Nematic Suspension by a Moving Nematic-Isotropic Interface" *Phys. Rev. E* 66, 012702 (2002).

35 M. Megens and J. Aizenberg. "Like-Charged Particles at Liquid Interfaces" *Nature* 424, 1014 (2003).

36 M. Oettel and S. Dietrich. "Colloidal Interactions at Fluid Interfaces" *Langmuir* 24, 1425-1441 (2008).

37 R. W. Style, C. Hyland, R. Boltyanskiy, J. S. Wettlaufer and E. R. Dufresne. "Surface Tension and Contact with Soft Elastic Solids" *Nat. Commun.* 4, 2728 (2013).

38 J. N. Israelachvili. *Intermolecular and Surface Forces* 3rd edn (Elsevier Science, 2010).

39 J. L. West, K. Zhang, A. Glushchenko, Y. Reznikov and D. Andrienko. "Drag of Micro-Particles by an Extended Nematic-Isotropic Interface" *Mol. Cryst. Liq. Cryst.* 422, 73-82 (2004).

40 I. H. Lin, D. S. Miller, P. J. Bertics, C. J. Murphy, J. J. de Pablo and N. L. Abbott. "Endotoxin-Induced Structural Transformations in Liquid Crystalline Droplets" *Science* 332, 1297-1300 (2011).

41 J.-C. Loudet, P. Barois and P. Poulin. "Colloidal Ordering from Phase Separation in a Liquid-Crystalline Continuous Phase" *Nature* 407, 611-613 (2000).

42 D. Andrienko, M. Tasinkevych, P. Patricio and M. M. T. da Gama. "Interaction of Colloids with a Nematic-Isotropic Interface" *Phys. Rev. E* 69, 021706 (2004).

43 N. Zimmermann, G. Junnemann-Held, P. J. Collings and H.-S. Kitzerow. "Self-Organized Assemblies of Colloidal Particles Obtained from an Aligned Chromonic Liquid Crystal Dispersion" *Soft Matter* 11, 1547-1553 (2015).

44 J. C. Loudet, P. Hanusse and P. Poulin. "Stokes Drag on a Sphere in a Nematic Liquid Crystal" *Science* 306, 1525-1525 (2004).

45 S. Palagi, A. G. Mark, S. Y. Reigh, K. Melde, T. Qiu, H. Zeng, C. Parmeggiani, D. Martella, A. S.-. Castillo, N. Kapernaum, F. Giesselmann, D. S. Wiersma, E. Lauga and P. Fischer. "Structured Light Enables Biomimetic Swimming and Versatile Locomotion of Photoresponsive Soft Microrobots" *Nat. Mat.* 15, 647-653 (2016).

46 T. J. White and D. J. Broer. "Programmable and Adaptive Mechanics with Liquid Crystal Polymer Networks and Elastomers" *Nat. Mat.* 14, 1087-1098 (2015).

47 V. Borshch, Y.-K. Kim, Y. Xiang, M. Gao, A. Jakli, V. P. Panov, J. K. Vij, C. T. Imrie, M. G. Tamba, G. H. Mehl and O. D. Lavrentovich. "Nematic Twist-Bend Phase with Nanoscale Modulation of Molecular Orientation" *Nat. Commun.* 4, 2635 (2013).

48 Z. Pei, Y. Yang, Q. Chen, E. M. Terentjev, Y. Wei and Y. Ji. "Mouldable Liquid-Crystalline Elastomer Actuators with Exchangeable Covalent Bonds" *Nat. Mat.* 13, 36-41 (2013).

49 E. Bukusoglu, M. B. Pantoja, P. C. Mushenheim, X. Wang and N. L. Abbott. "Design of Responsive and Active (Soft) Materials Using Liquid Crystals" *Annu. Rev. Chem. Biomol. Eng.* 7, 163-196 (2016).

50 I. Musevic, M. Skarabot, U. Tkalec, M. Ravnik and S. Zumer. "Two-Dimensional Nematic Colloidal Crystals Self-Assembled by Topological Defects" *Science* 313, 954-958 (2006).

51 P. K. Mukherjee. "The $T_{ni}$-T* Puzzle of the Nematic-Isotropic Phase Transition" *J. Phys.: Condens. Matter* 10, 9191-9205 (1998).

52 Y.-K. Kim, M. Majumdar, B. I. Senyuk, L. Tortora, J. Seltmann, M. Lehmann, A. Jkli, J. T. Gleeson, O. D. Lavrentovich and S. Sprunt. "Search for Biaxiality in a Shape-Persistent Bent-Core Nematic Liquid Crystal" *Soft Matter* 8, 8880-8890 (2012).

53 Y.-K. Kim, B. Senyuk and O. D. Lavrentovich. "Molecular Reorientation of a Nematic Liquid Crystal by Thermal Expansion" *Nat. Commun.* 3, 1133 (2012).

54 E. Yariv and H. Brenner. "Flow Animation by Unsteady Temperature Fields" *Phys. Fluids* 16, L95 (2004).

55 A. Tripathi, O. Bozkurt and A. Chauhan. "Dispersion in Microchannels with Temporal Temperature Variations" *Phys. Fluids* 17, 103607 (2005).

56 F. M. Weinert, C. B. Mast and D. Braun. "Optical Fluid and Biomolecule Transport with Thermal Fields" *Phys. Chem. Chem. Phys.* 13, 9918 (2011).

57 A. D. Rey. "Marangoni Flow in Liquid Crystal Interfaces" *J. Chem. Phys.* 110, 9769-9770 (1999).

58 A. D. Rey. "Tension Gradients and Marangoni Flows in Nematic Interfaces" *Phys. Rev. E* 60, 1077-1080 (1999).

59 M. G. Velarde and R. K. Zeytounian. *Interfacial Phenomena and the Marangoni Effect* (Springer-Verlag Wien, 2002).

60 H. Takezoe and H. Choi. "Circular Flow Formation Triggered by Marangoni Convection in Nematic Liquid Crystal Films with a Free Surface" *Soft Matter* 12, 481-485 (2016).

61 S. Herminghaus, C. C. Maass, C. Kruger, S. Thutupalli, L. Goehring and C. Bahr. "Interfacial Mechanisms in Active Emulsions" *Soft Matter* 10, 7008-7022 (2014).

62 C. C. Maass, C. Kruger, S. Herminghaus and C. Bahr. "Swimming Droplets" *Annu. Rev. Condens. Matter Phys.* 7, 171-193 (2016).

63 Z. G. Zheng, Y. N. Li, H. K. Bisoyi, L. Wang, T. J. Bunning and Q. Li. "Three-Dimensional Control of the Helical Axis of a Chiral Nematic Liquid Crystal by Light" *Nature* 531, 352-356 (2016).

64 D.-K. Yang and S.-T. Wu. *Fundamentals of Liquid Crystal Devices* (John Wiley & Sons, Ltd., 2006).

65 D. Demus, J. Goodby, G. W. Gray, H.-W. Spiess and V. Vill. *Handbook of Liquid Crystals* Vol. 2 (Wiley-VCH Verlag GmbH, 1998).

66 C. J. Kearney and D. J. Mooney. "Macroscale Delivery Systems for Molecular and Cellular Payloads" *Nat. Mater.* 12, 1004-1017 (2013).

67 X. J. Kang, Z. Y. Cheng, D. M. Yang, P. A. Ma, M. M. Shang, C. Peng, Y. L. Dai and J. Lin. "Design and Synthesis of Multifunctional Drug Carriers Based on Luminescent Rattle-Type Mesoporous Silica Microspheres with a Thermosensitive Hydrogel as a Controlled Switch" *Adv. Funct. Mater.* 22, 1470-1481 (2012).

68 J. Lydon. "Chromonic Review" *J. Mater. Chem.* 20, 10071-10099 (2010).

69 K. Peddireddy, P. Kumar, S. Thutupalli, S. Herminghaus and C. Bahr. "Solubilization of Thermotropic Liquid Crystal Compounds in Aqueous Surfactant Solutions" *Langmuir* 28, 12426-12431 (2012).

70 E. P. Raynes, R. J. A. Tough and K. A. Davies. "Voltage Dependence of the Capacitance of a Twisted Nematic Liquid Crystal Layer" *Mol. Cryst. Liq. Cryst.* 56, 63-68 (1979).

71 J.-W. Kim, H. Kim, M. Lee and J. J. Magda. "Interfacial Tension of a Nematic Liquid Crystal/Water Interface with Homeotropic Surface Alignment" *Langmuir* 20, 8110-8113 (2004).

72 "The Values Were Measured in Our Lab."

73 S. Faetti and V. Palleschi. "Measurements of the Interfacial Tension between Nematic and Isotropic Phase of Some Cyanobiphenyls" *J. Chem. Phys.* 81, 6254-6258 (1984).

74 J. Janik, A. Krol-Otwinowska, D. Sokolowska and J. K. Moscicki. "Pendulum Viscometer: A New Method for Measurement of Miesowicz Nematic Shear Viscosity Coefficients $H_1$ and $H_2$" *Rev. Sci. Instrum.* 77, 123906 (2006).

75 K. Holmberg, B. Jönsson, B. Kronberg and B. Lindman. *Surfactants and Polymer in Aqueous Solution* (John Wiley & Sons, Ltd., 2002).

76 K. Harth, L. M. Shepherd, J. Honaker and R. Stannarius. "Dynamic Interface Tension of a Smectic Liquid Crystal in Anionic Surfactant Solutions" *Phys. Chem. Chem. Phys.* 17, 26198-26206 (2015).

77 μL. H. Ong and K.-L. Yang. "Surfactant-Driven Assembly of Poly(Ethylenimine)-Coated Microparticles at the Liquid Crystal/Water Interface" *J. Phys. Chem. B* 120, 825-833 (2016).

We claim:

1. A system for the controlled release of a guest composition sequestered within a host composition, the system comprising:
   (a) a host composition comprising an anisotropic fluid, wherein the host composition does not comprise a lyotropic liquid crystal;
   (b) a guest composition sequestered within the host composition, wherein the guest composition is in a form of a plurality of liquid droplets, the guest composition is immiscible or insoluble in the host composition, and the guest composition forms an interface with the host composition upon which elastic repulsion forces act to prevent release of the guest composition from the host composition; and
   (c) a composition in fluid communication with the host composition, the composition (c) capable of changing the elastic repulsion forces, introducing one or more counter forces, or both, such that the elastic repulsion forces do not act to prevent release of the guest composition from the host composition.

2. The system of claim 1, wherein the liquid droplets of the plurality of liquid droplets are aqueous droplets.

3. The system of claim 2, wherein the aqueous droplets comprise amphiphiles positioned at the interface.

4. The system of claim 1, wherein the anisotropic fluid is a liquid crystal.

5. The system of claim 4, wherein the liquid crystal is a thermotropic liquid crystal.

6. The system of claim 1, wherein the liquid droplets of the plurality of liquid droplets are aqueous droplets comprising amphiphiles positioned at the interface and the anisotropic fluid is a thermotropic liquid crystal.

7. The system of claim 1, wherein the composition (c) is positioned adjacent to and in contact with the host composition.

8. The system of claim 1, wherein the composition (c) comprises one or more of a charged molecule, an amphiphile, a polymer, a solute that is miscible in the host composition, a pH-changing agent, motile bacteria, and a light-sensitive compound.

9. The system of claim 1, consisting of the host composition, the guest composition, and the composition (c).

10. The system of claim 9, wherein the liquid droplets of the plurality of liquid droplets are aqueous droplets comprising amphiphiles positioned at the interface, the anisotropic fluid is a thermotropic liquid crystal, and the composition (c) is positioned adjacent to and in contact with the host composition.

11. The system of claim 1, further comprising (d) a device capable of changing the elastic repulsion forces, introducing the one or more counter forces, or both, such that the elastic repulsion forces do not act to prevent release of the guest composition from the host composition.

12. The system of claim 11, wherein the device (d) is selected from a device capable of changing a temperature of the host composition, a source of an electric field or a magnetic field, and a device capable of inducing a shear stress at the interface.

13. The system of claim 12, consisting of the host composition, the guest composition, the composition (c), and the device (d).

14. The system of claim 13, wherein the liquid droplets of the plurality of liquid droplets are aqueous droplets comprising amphiphiles positioned at the interface, the anisotropic fluid is a thermotropic liquid crystal, and the composition (c) is positioned adjacent to and in contact with the host composition.

15. A method of using the system of claim 1, the method comprising changing the elastic repulsion forces, introducing the one or more counter forces, or both, by inducing the fluid communication between the composition (c) and the host composition to release the guest composition from the host composition.

16. A system for the controlled release of a guest composition sequestered within a host composition, the system comprising:
   (a) a host composition comprising an anisotropic fluid, wherein the host composition does not comprise a lyotropic liquid crystal;
   (b) a guest composition sequestered within the host composition, wherein the guest composition is in a form of a plurality of liquid droplets, the guest composition is immiscible or insoluble in the host composition, and the guest composition forms an interface with the host composition upon which elastic repulsion forces act to prevent release of the guest composition from the host composition; and
   (c) a device capable of changing the elastic repulsion forces, introducing one or more counter forces, or both, such that the elastic repulsion forces do not act to prevent release of the guest composition from the host composition.

17. The system of claim 16, wherein the device (c) is selected from a device capable of changing a temperature of the host composition, a source of an electric field or a magnetic field, and a device capable of inducing a shear stress at the interface.

18. The system of claim 17, the system consisting of the host composition, the guest composition, and the device (c).

19. The system of claim 18, wherein the liquid droplets of the plurality of liquid droplets are aqueous droplets comprising amphiphiles positioned at the interface and the anisotropic fluid is a thermotropic liquid crystal.

20. A method of using the system of claim 16, the method comprising changing the elastic repulsion forces, introducing the one or more counter forces, or both, by operating the device (c) to release the guest composition from the host composition.

\* \* \* \* \*